(12) United States Patent
Flores Hernández et al.

(10) Patent No.: US 8,084,203 B2
(45) Date of Patent: Dec. 27, 2011

(54) METHODS FOR THE DETERMINATION OF TELOMERE LENGTH IN A SEMI-AUTOMATIC MANNER OF EVERY SINGLE CELL IN A IMMOBILIZED CELL POPULATION

(75) Inventors: Ignacio Flores Hernández, Madrid (ES); Andrés Canela Rodriguez, Cold Spring Harbor, NY (US); Maria Antonia Blasco Marhuenda, Madrid (ES)

(73) Assignee: Fundacion Centro Nacional de Investigaciones Oncologicas Carlos III, Madrid (ES)

( * ) Notice: Subject to any disclaimer, the term of this patent is extended or adjusted under 35 U.S.C. 154(b) by 661 days.

(21) Appl. No.: 12/119,327

(22) Filed: May 12, 2008

(65) Prior Publication Data

US 2009/0280485 A1    Nov. 12, 2009

(51) Int. Cl.
*C12Q 1/68* (2006.01)
*C12M 1/34* (2006.01)
*C07H 21/04* (2006.01)

(52) U.S. Cl. .................. 435/6.1; 435/287.2; 536/24.31
(58) Field of Classification Search .................. None
See application file for complete search history.

(56) References Cited

U.S. PATENT DOCUMENTS 6,514,693 B1 * 2/2003 Lansdorp .................. 435/6.13

FOREIGN PATENT DOCUMENTS

| WO | 9641016 A1 | 12/1996 |
| WO | 2004/035597 A2 | 4/2004 |
| WO | 2008081451 A2 | 7/2008 |

OTHER PUBLICATIONS

Canela, A. et al. Proceedings of the National Academy of Sciences USA 104(13):5300-5305 (Mar. 27, 2007; published online Mar. 16, 2007).*
Baerlocher, G.M. et al. Nature Protocols 1(5):2365-2376 (published online Dec. 21, 2006).*
Andres Canela Rodriguez, Estudio de las nuevas funciones de la telomerasa en la tumorigenesis, Thesis Doctoral 2007, pp. 1-257 (cited in 8 parts), publically available Jan. 2008.*
Ignacio Flores, et al., The longest telomeres: a general signature of adult stem cell compartments, GENES & DEVELEPMENT, pp. 654-667, vol. 22, Mar. 1, 2008 (online Feb. 18, 2008).
Steven S.S. Poon, et al.,Telonnere Length Measurements Using Digital Fluorescence Microscopy, Cytometry, 1999 pp. 267-278, vol. 36.

(Continued)

*Primary Examiner* — Diana Johannsen
(74) *Attorney, Agent, or Firm* — Andrew D. Gerschutz; Tristan A. Fuierer; Moore & Van Allen, PLLC

(57) ABSTRACT

The invention relates to methods and reagents for the determination of telomere length in tissue sections by the single cell telomeric mapping technique based on a fluorescent in situ hybridization step using a telomere-specific probe and an interpolation step using a standard curve correlating fluorescent intensity and telomere length obtained from a collection of cell lines of known telomere length. The invention further relates to methods for the identification of stem cell niches within tissues and for the identification of compounds capable of triggering stem cell mobilization using the telomere length as criteria for the identification of stem cells and which rely on the single cell telomeric mapping technique of the invention.

12 Claims, 54 Drawing Sheets

OTHER PUBLICATIONS

Sabita N. Saldanha, et al., Assesment of telomere length and factors that contribute to its stability, Eur. J. Biochem, 2003, pp. 389-403, vol. 270.

Irene Siegl-Cachedenier, et al., Telomerase reverses epidermal hair follicle stem cell defects and loss of long-term survival associated with critically short telomeres, The Journal of Cell Biology, Oct. 2, 2007, pp. 277-290, vol. 179, No. 2.

Ignacio Flores, et al., Telomerase regulation and stem cell behaviour, Current Opinion in Cell Biology, 2006, pp. 254-260, vol. 18

English translation of Conclusion from Andes Canaela Rodriguez Doctoral Thesis, 2007, (3 pages).

Canela, A., et al., "Constitutive expression of tert in thymocytes leads to increased incidence and dissemination of T-cell lymphoma in Lck-Tert mice," Mol. Cell Biol. May 2004; 24(10):4275-93.

Canela, A., et al., "High-throughput telomere length quantification by FISH and its application to human population studies," Proc. Natl. Acad. Sci. USA Mar. 27, 2007; 104(13):5300-5.

Flores, I., "The longest telomeres: a general signature of adult stem cell compartments". 2007 Sometido, 43 page manuscript (vol./No./pp. N/A).

* cited by examiner

*b*

G1 *Terc−/−*
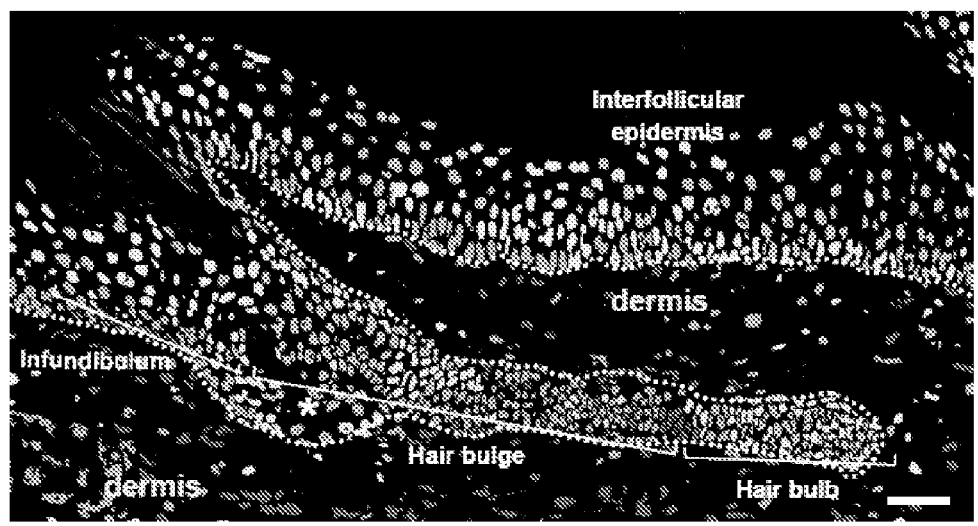
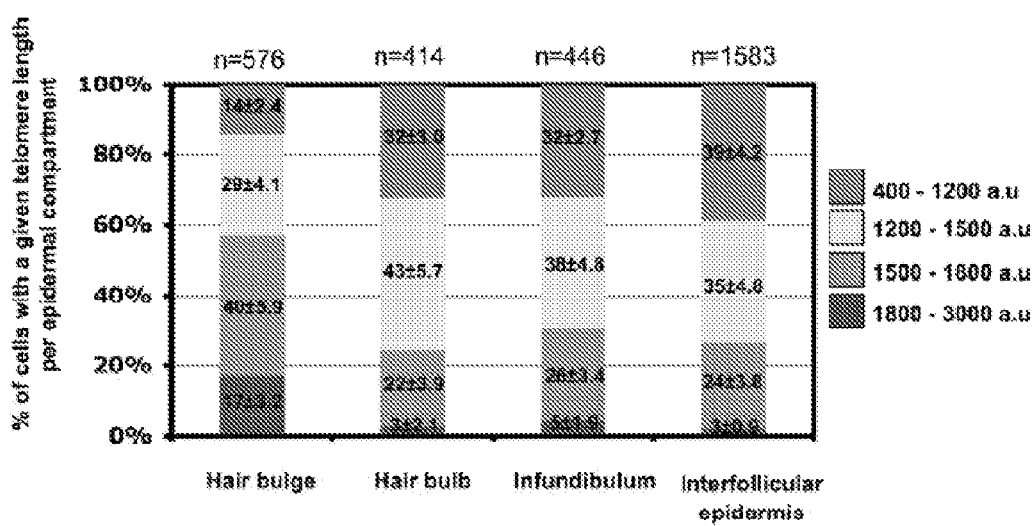
Figure 1C (continuation)

a

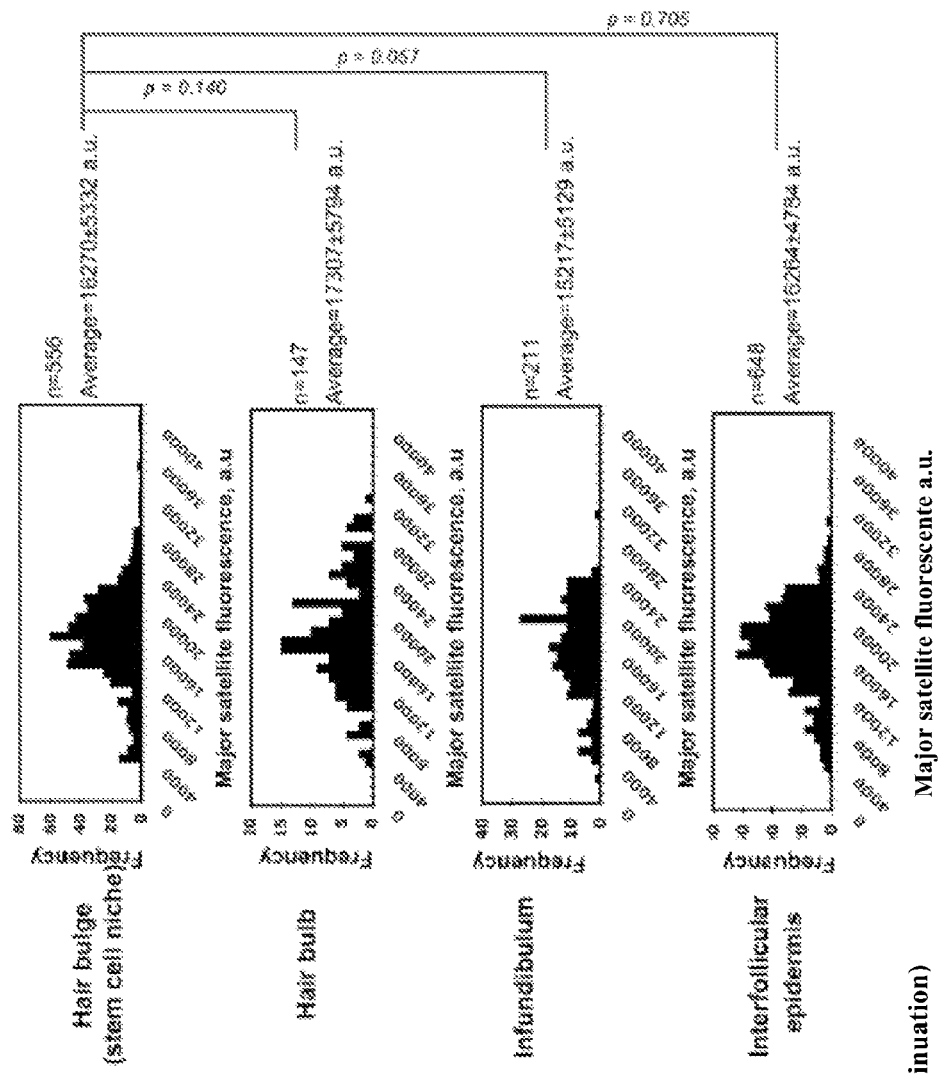
Figure 3A (continuation)

All P values correspond to comparisons between the indicated compartment with the hair bulge (stem cell niche)

*f*

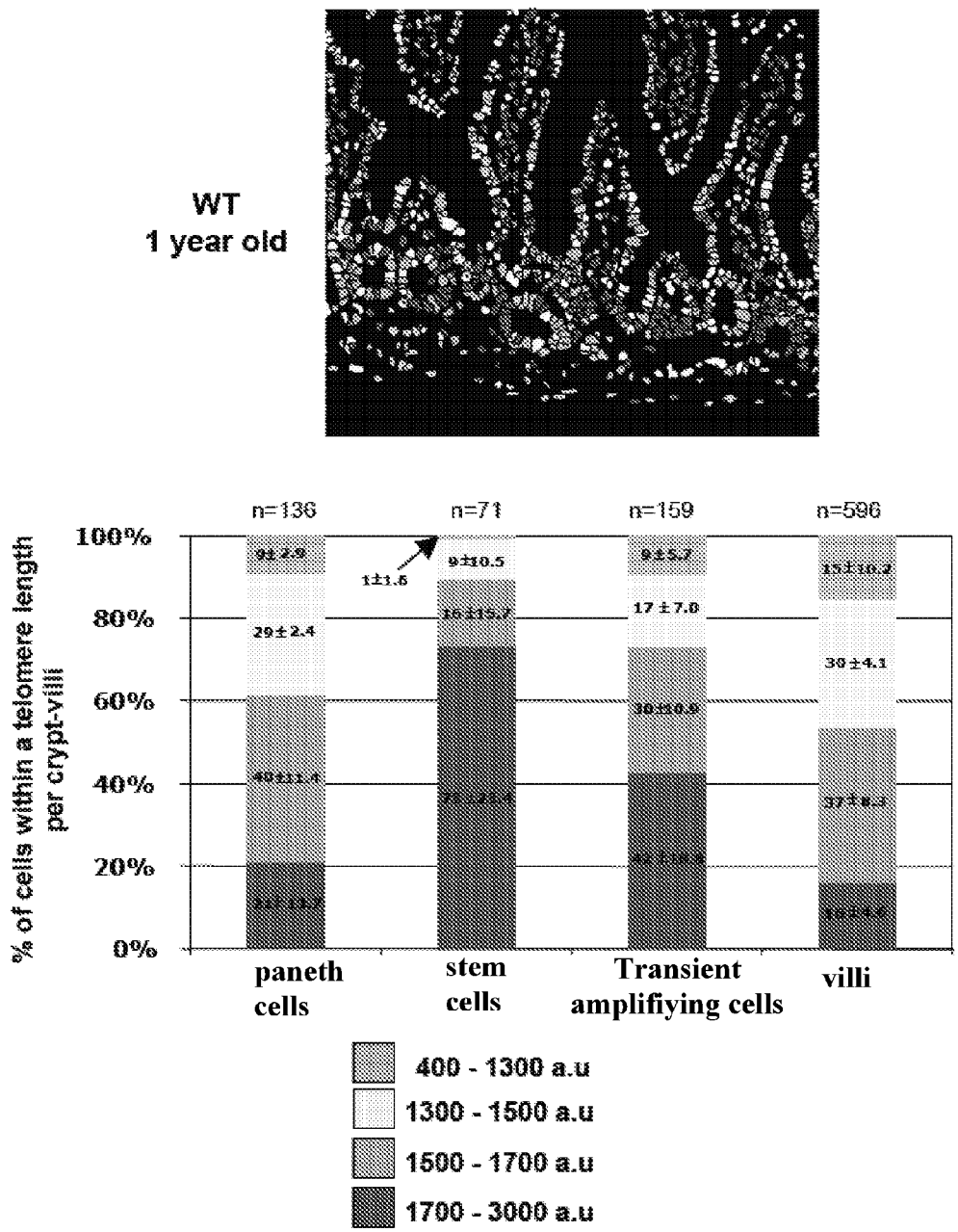
Figure 11A (continuation)

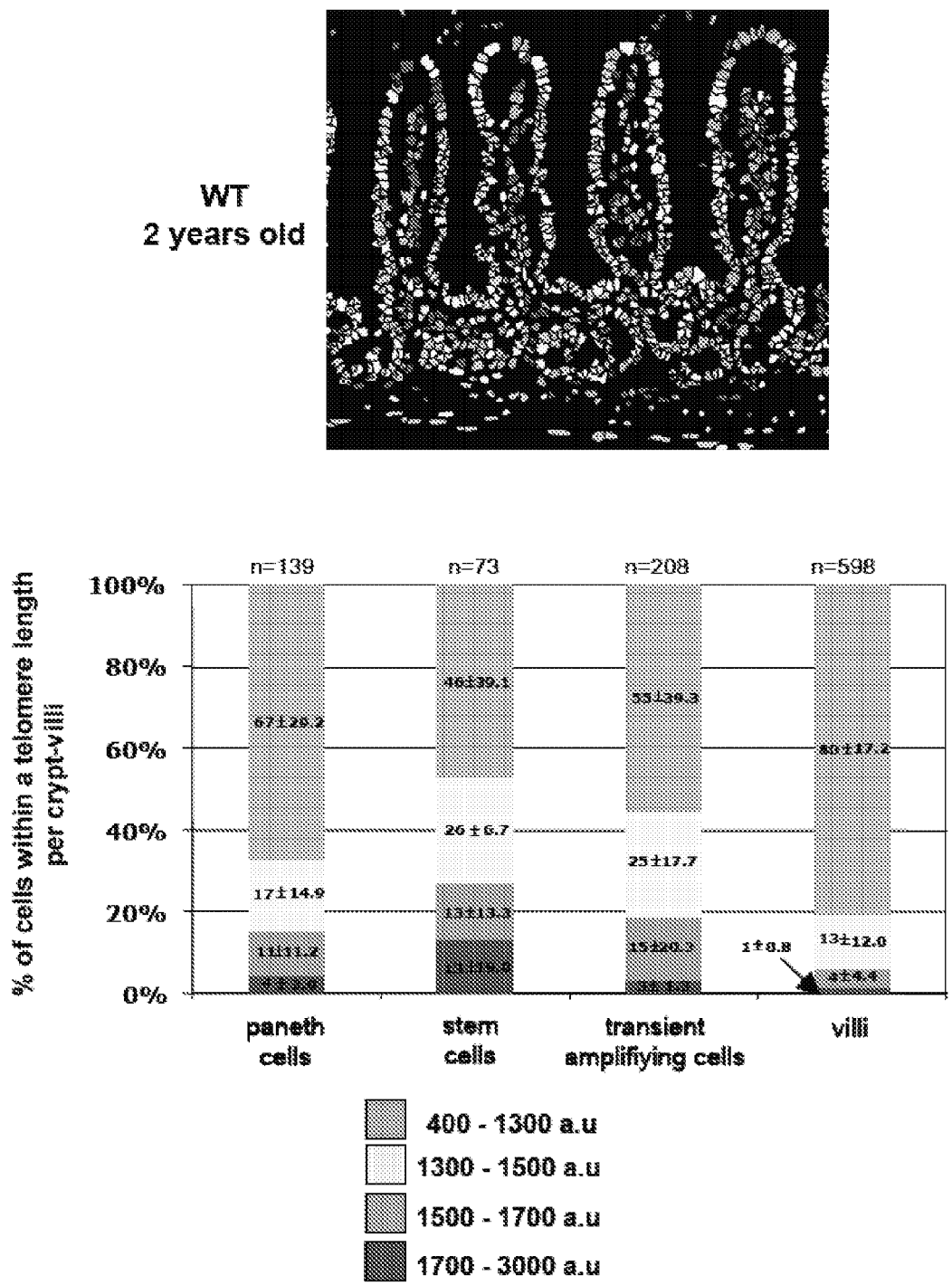
Figure 11A (continuation)

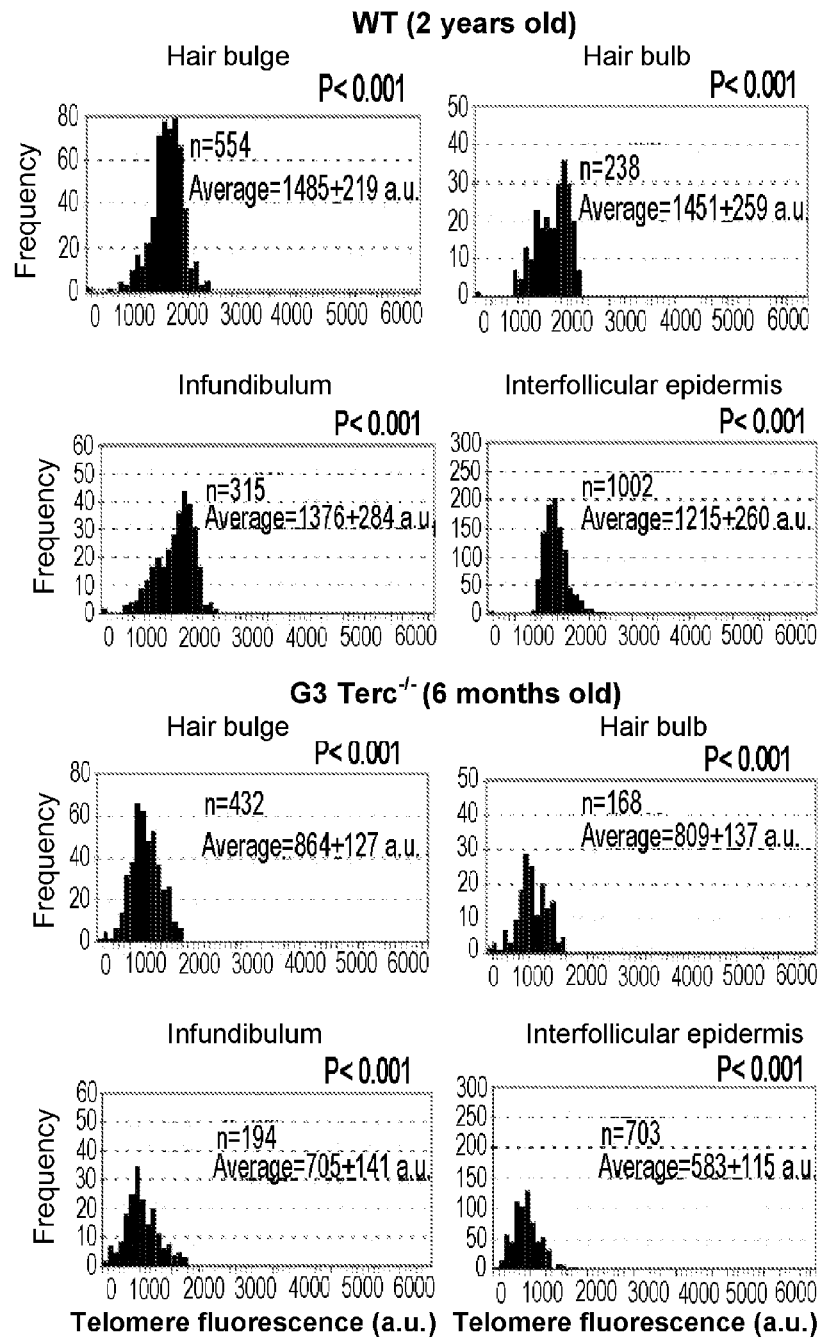
* All P values correspond to comparisons of the indicated age and genotype with the 2 month old WT animals within each skin compartment
Figure 11C (continuation)

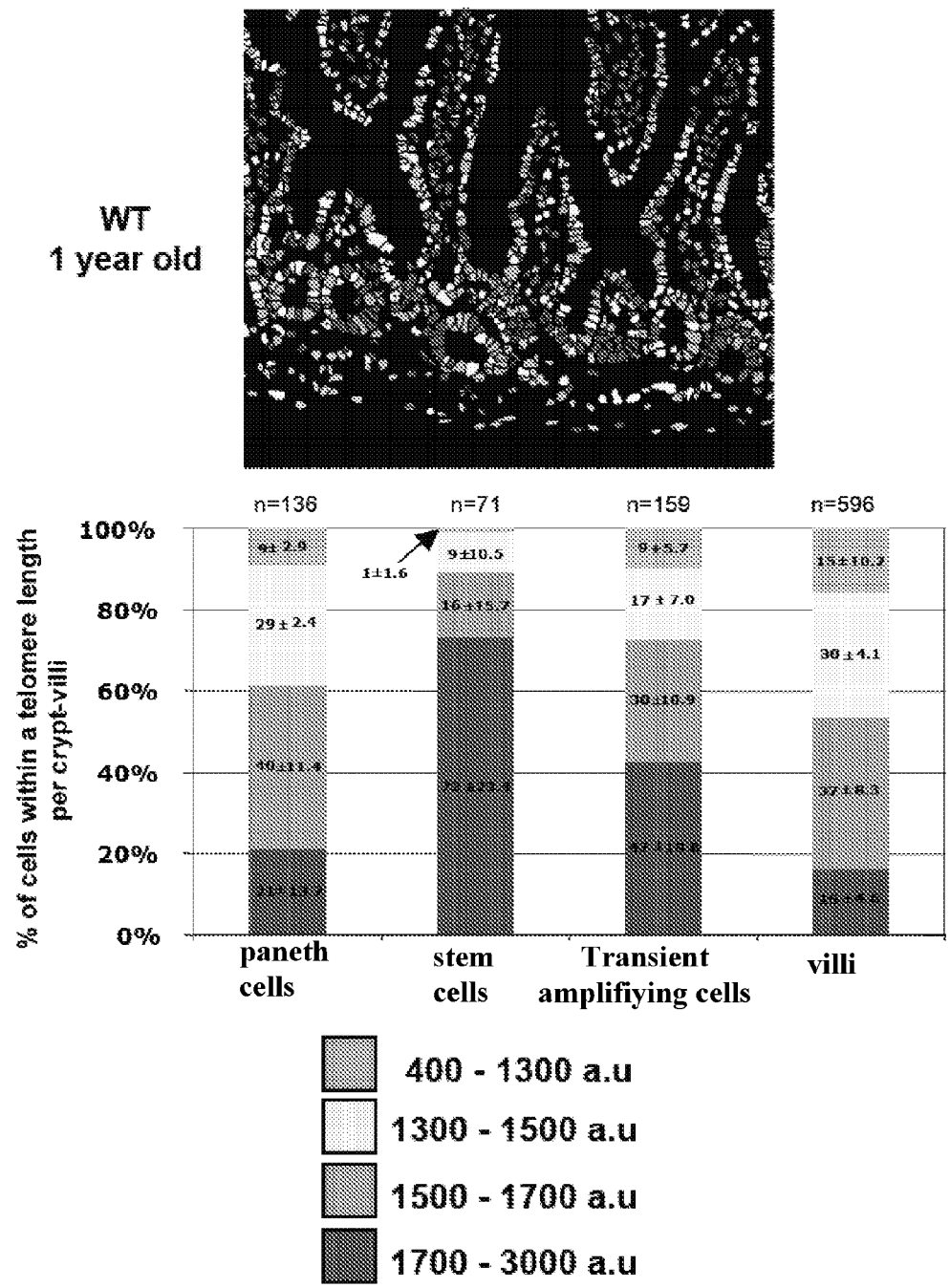
Figure 12A (continuation)

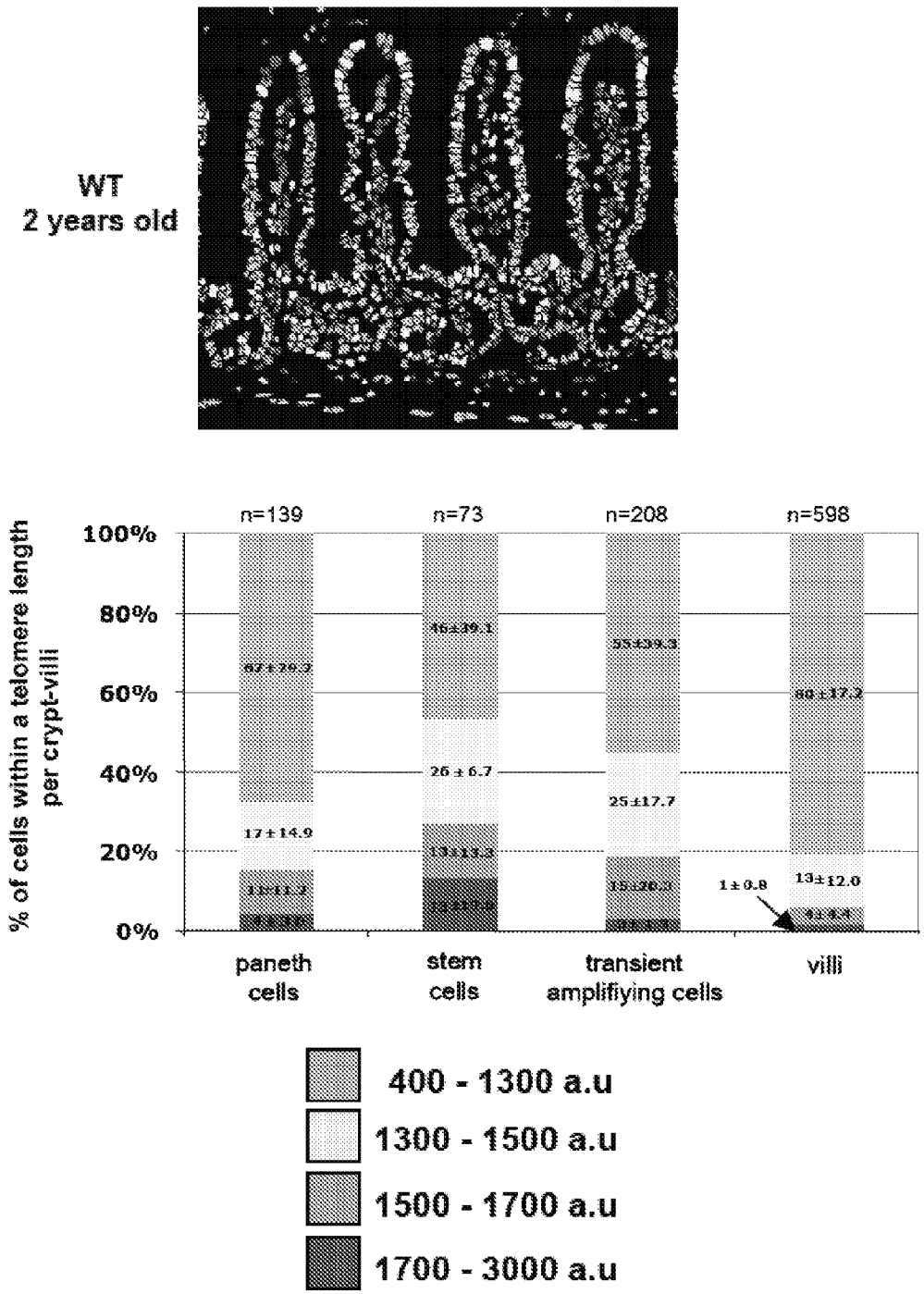
Figure 12A (continuation)

*All P values correspond to comparisons of the indicated age and genotype with the 2 month old WT animals within each SI compartment.

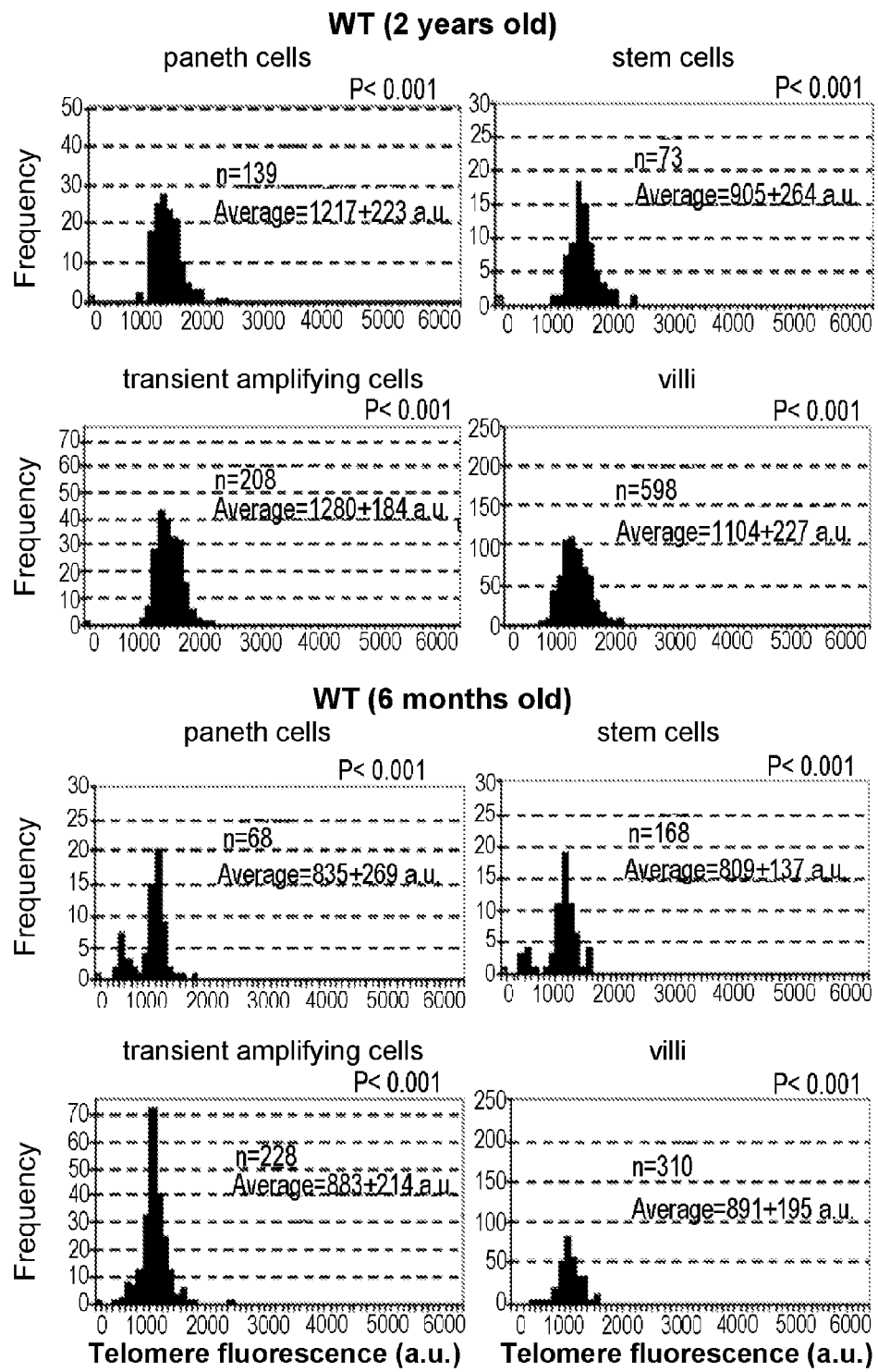
* All P values correspond to comparisons of the indicated age and genotype with the 2 month old WT animals within each SI compartment
Figure 12C (continuation)

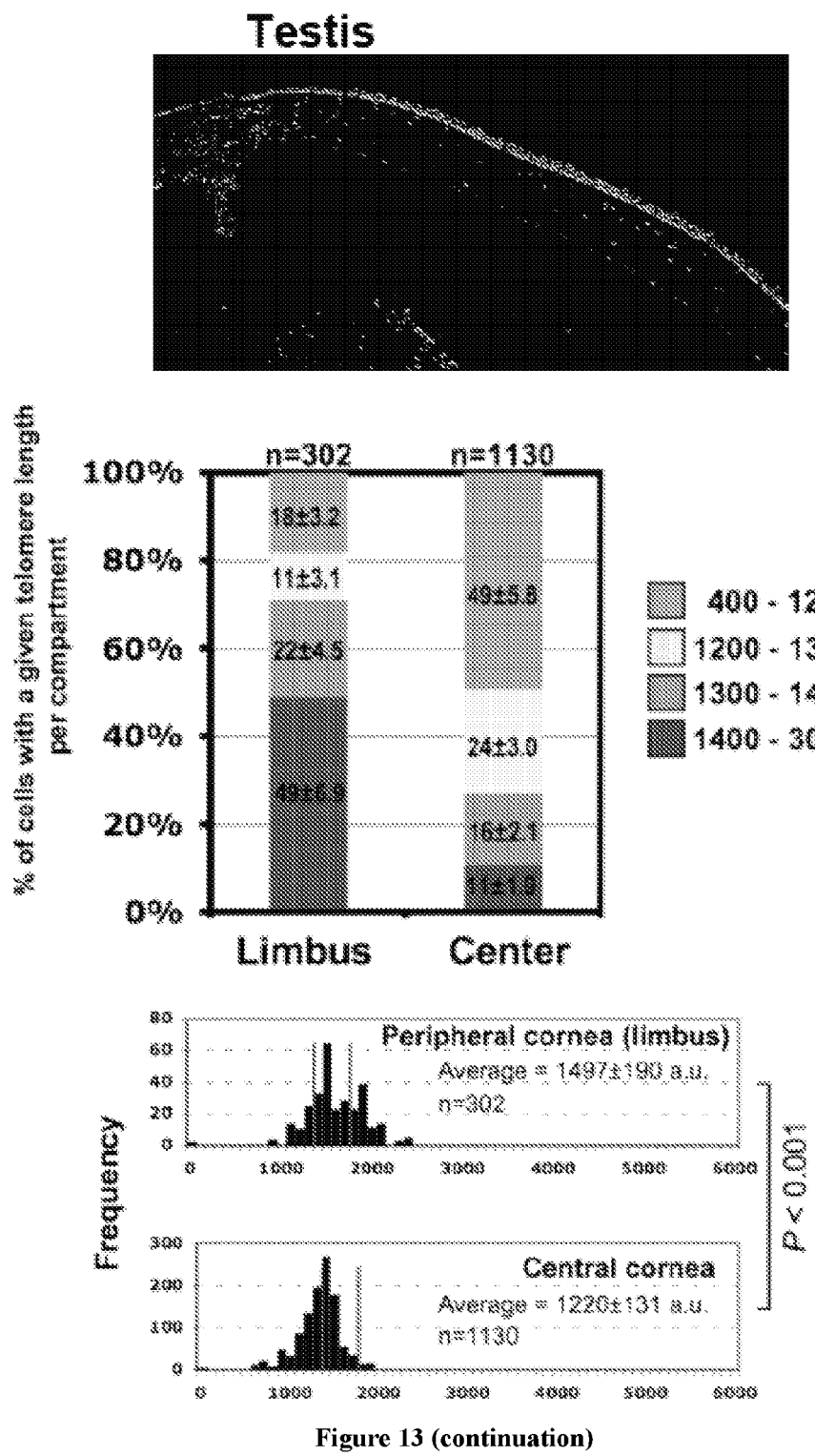
Figure 13 (continuation)

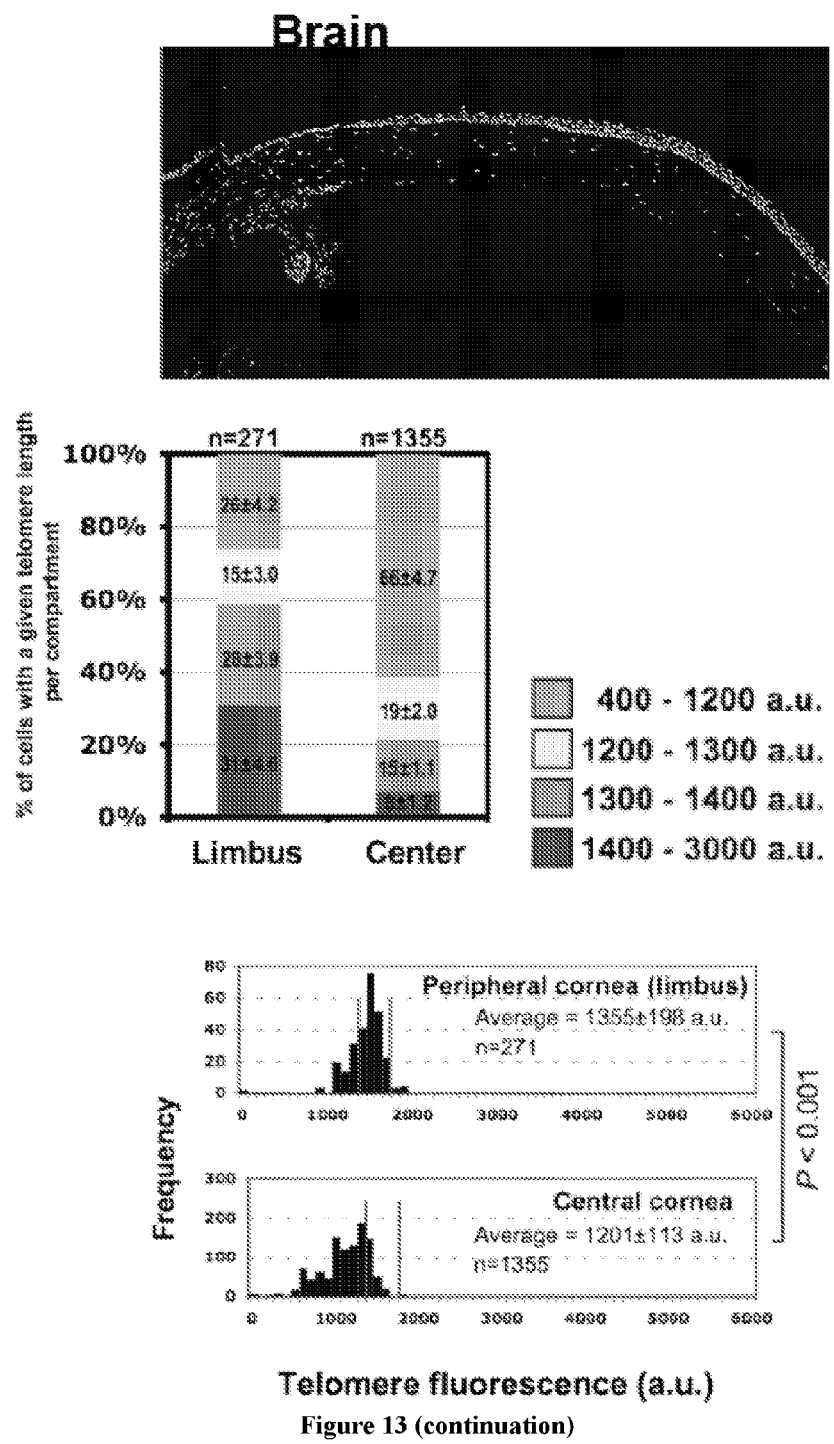
Figure 13 (continuation)

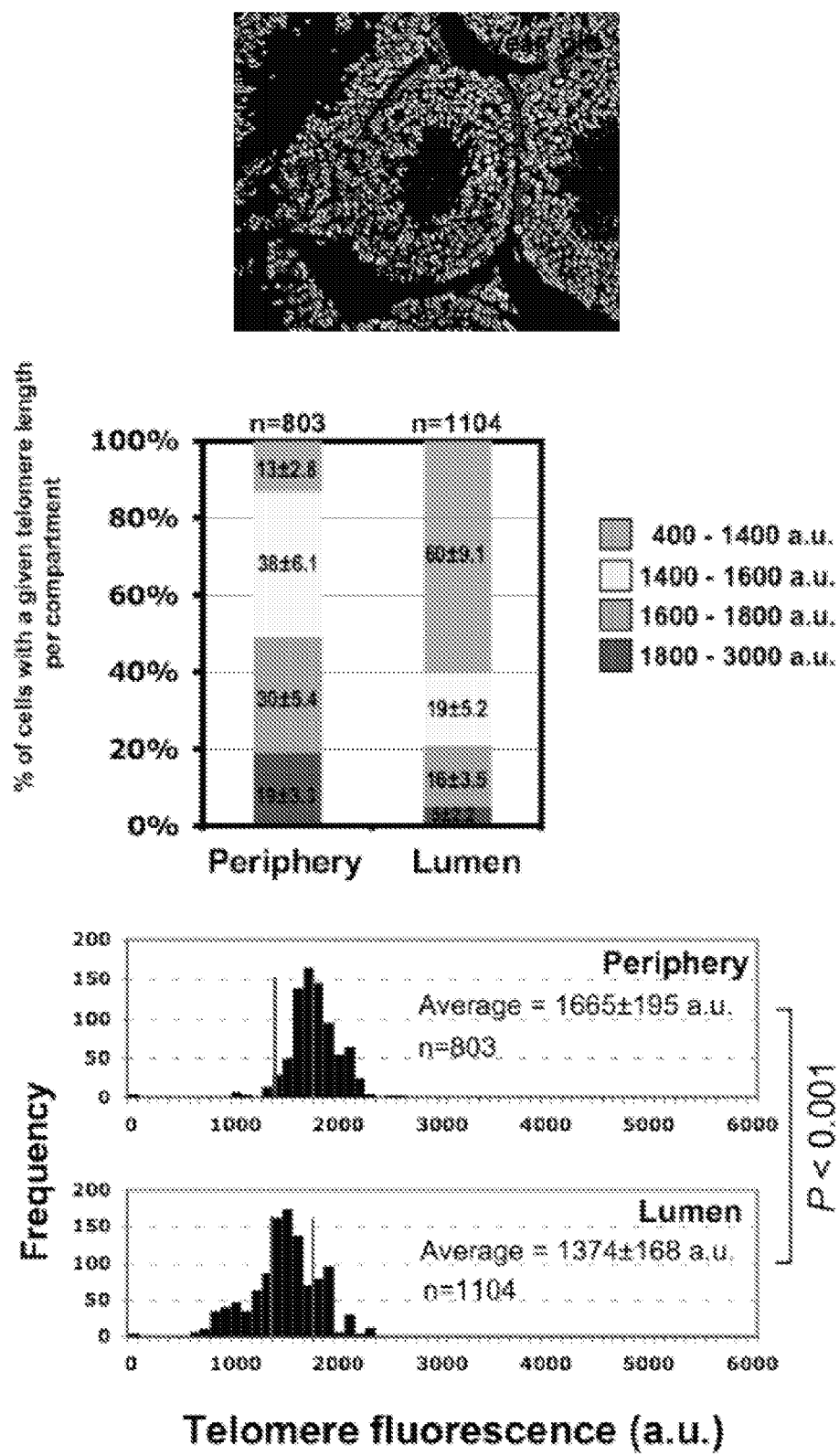
Figure 14 (continuation)

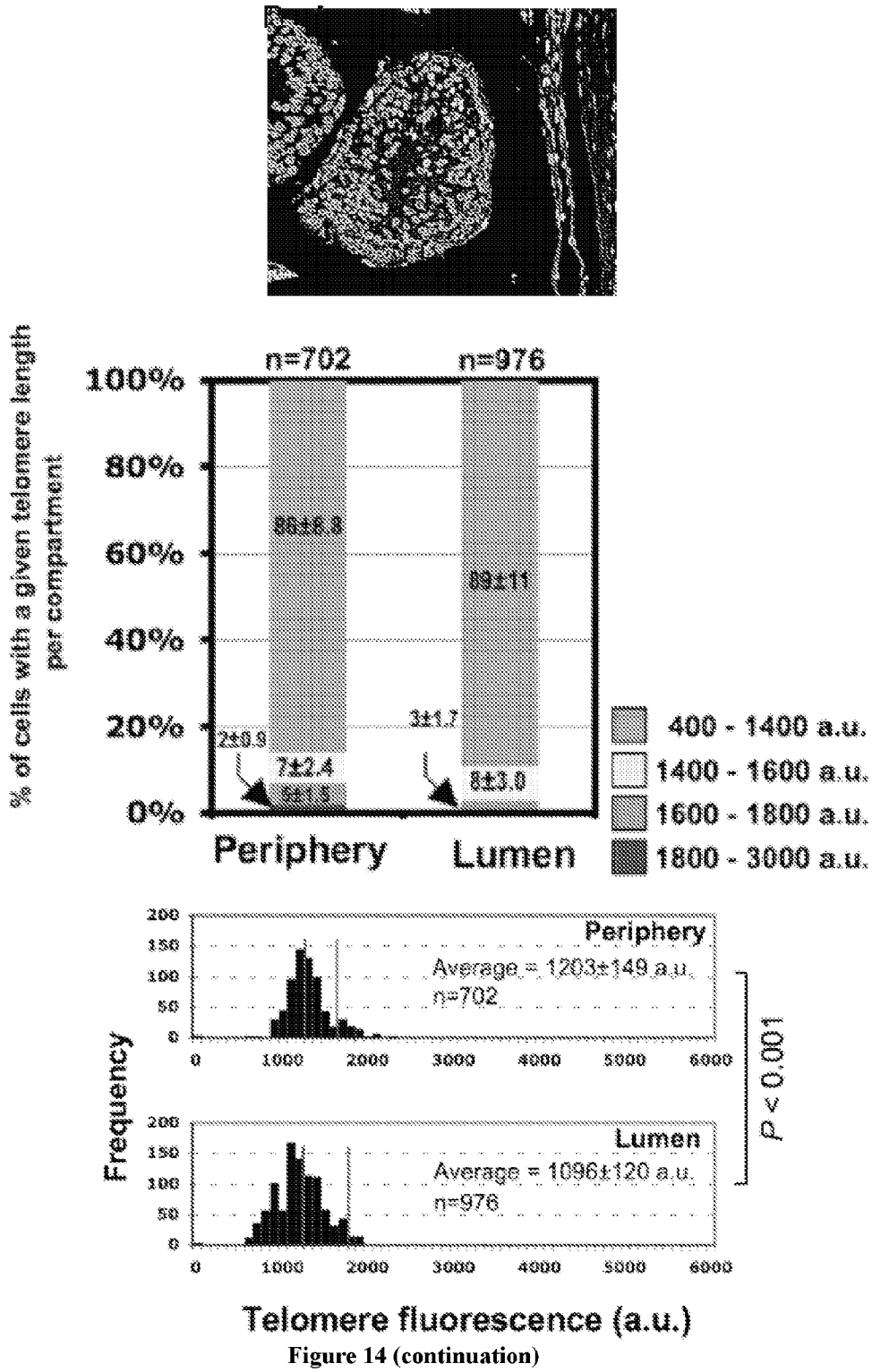
Figure 14 (continuation)

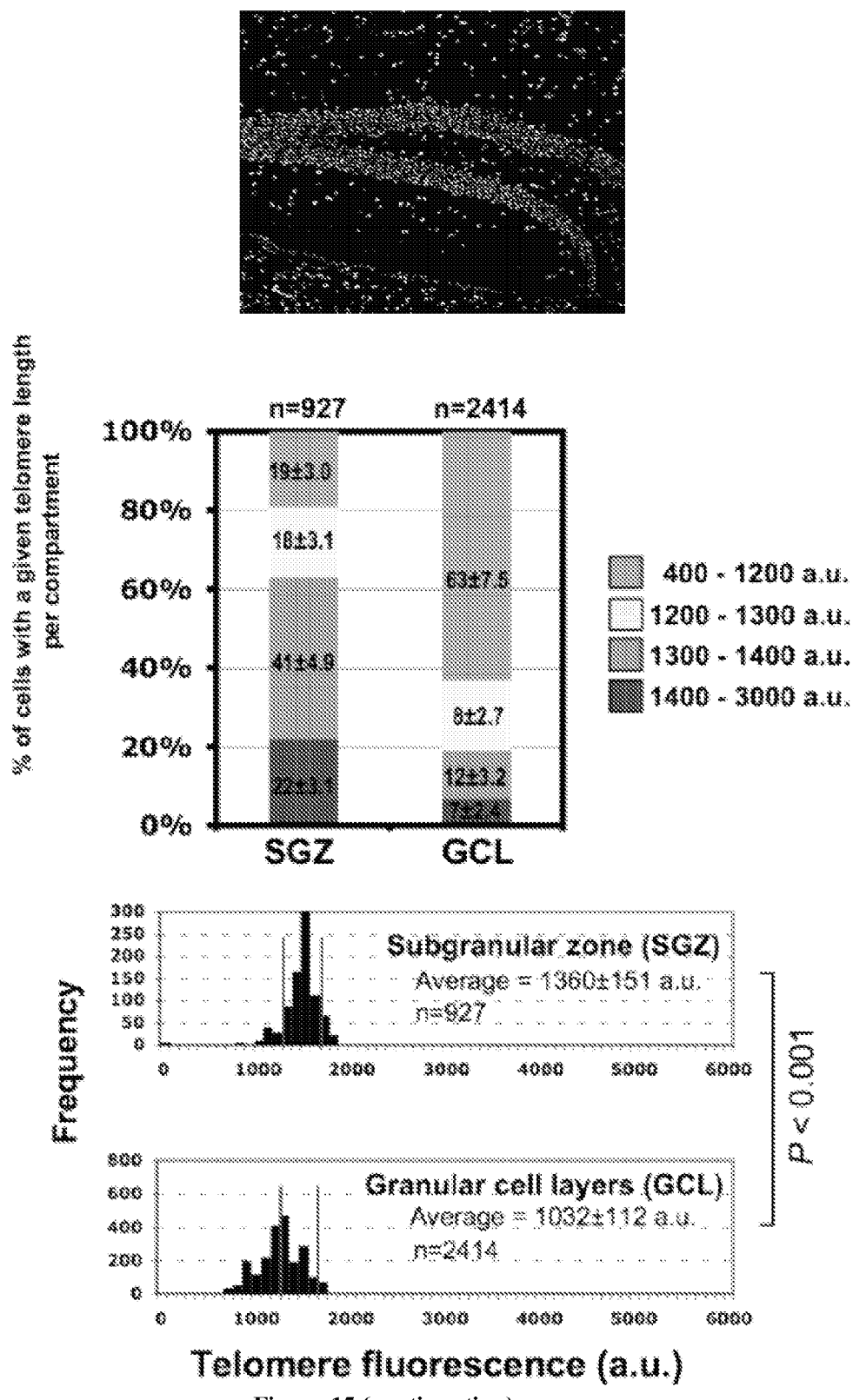
Figure 15 (continuation)

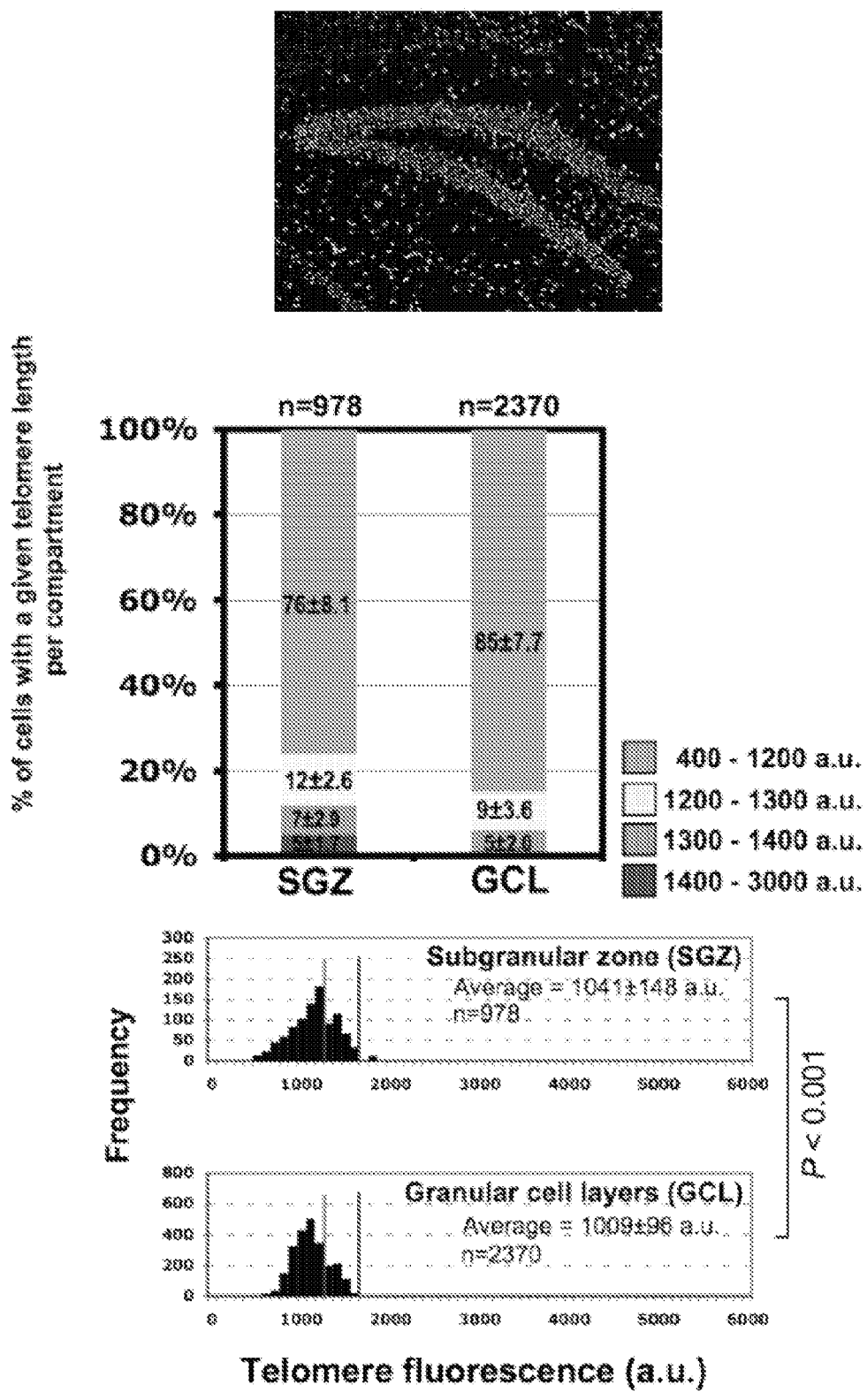
Figure 15 (continuation)

SEQUENCE LISTING

<160> NUMBER OF SEQ ID NOS: 1

<210> SEQ ID NO 1
<211> LENGTH: 17
<212> TYPE: DNA
<213> ORGANISM: Artificial
<220> FEATURE:
<223> OTHER INFORMATION: Centromeric probe

<400> SEQUENCE: 1
tcgccatatt ccaggtc                                                  17

METHODS FOR THE DETERMINATION OF TELOMERE LENGTH IN A SEMI-AUTOMATIC MANNER OF EVERY SINGLE CELL IN A IMMOBILIZED CELL POPULATION

FIELD OF THE INVENTION

The invention relates to methods for determining telomere length within the cells of an immobilized cell population as well as to methods for the identification of stem cells in a cell population based on the telomere length. Both methods rely on detecting the fluorescent emission of telomere-specific probes which have been previously contacted with the population of cells wherein the telomere length of the individual cells is to be determined or wherein the stem cells are to be identified.

BACKGROUND OF THE INVENTION

Telomere length is a parameter of interest not only with respect to the study of the telomere biology but also as a marker for aging and cancer. Regarding aging, it is known that telomere length decreases with age because telomerase activity in adult tissue is not sufficient to prevent telomere shortening, thus compromising cellular viability (Harley et al., 1990 and Blasco et al., 1997). In the case of cancer cells, telomere length is maintained due to the over-expression of telomerase or due to the activation of alternative mechanisms which promote telomerase elongation (Kim et al., 1994 and Bryan et al., 1997).

Thus, telomere length can be used both in aging studies, as a marker of biological fitness of human populations (Cawthon et al., 2003; Epel et al., 2004, and Valdes et al., 2005, Lancet, 366:662-664), in cancer and in screening methods for the identification of compounds interfering with said biological fitness.

The most widely used method for determining telomeric length is the so-called telomere restriction fragment assay (Moyzis et al., 1988). This method is based on a Southern blot hybridisation of a telomeric restriction fragments derived from genomic DNA using probes specific for the telomere repeats. However, TRF is a time-consuming technique which requires plenty of cells and only provides an average telomeric length of the cell population under study without giving an indication of telomere length in individual cells.

Another method for determining telomere length is quantitative fluorescent in situ hybridisation (FISH) based on the use of fluorescence microscopy on a preparation of metaphasic cells using a telomere-specific probe (Lansdorp et al., 1996; Zijlmans et al., 1997), (Martens et al., 1998). This technique is also cumbersome and time-consuming and requires cells in metaphase, which excludes from all those cells which can not proliferate in culture.

Another method for determining telomere length is flow fluorescent in situ hybridisation (flow-FISH) based on the determination of telomeric fluorescence in interphase cells using flow cytometry wherein the cells are labelled with a fluorescently-labelled telomere-specific probe (Rufer et al., 1998; Baerlocher et al., 2006). However, this method is only applicable to cells in suspension and the results are frequently biased due to auto-fluorescence of the cytoplasm.

The hybridization protection assay described by Nakamura et al., (Clinical Chemistry, 1999, 45:1718-1724) is based on a chemoluminescence determination of the amount of telomere-specific probe and normalized to the signal obtained with an Alu repeat-specific probe. However, this method requires a constant number of Alu repeats in the genome.

Other methods for determining fluorescence length include the hybridization assay (Freulet-Marriere et al, 2004), primed in situ labeling (PRIMS) (Therkelsen et al., 1995), PCR-based methods such as STELA (Baird, D. M., et al., 2003) and quantitative PCR (Cawthon, R. M., 2002).

The identification of adult stem cell compartments is essential for studying adult stem cell properties and regulation, as well as for their potential use in regenerative medicine.

The common approach to locate stem cell niches has been based on the different expression of a protein marker, or more usually a complex set of protein markers, in stem cell environments compared to more differentiated compartments, as well as on the general property that stem cells are long-term residents of a tissue and have a low proliferative rate (i.e. label-retaining techniques) (Fuchs et al., 2004, Cell, 116:769-778; Moore and Lemischka, 2006, Science, 311:1880-1885). These approaches are limited because each type of stem cell niche has its own specific set of markers.

Cotsarelis et al. (Cell, 1990, 61:1329-1337), Potten et al., (Int. J. Exp. Pathol., 1997, 78: 219-243) and Zhang et al. (Nature, 2003, 425:836-841) have relied on the identification of long-term retention cells (LRCs) for the identification of skin, intestinal, and hematopoietic stem cells. This assay is based in the identification, using DNA labeling, of cells in a given tissue that undergo slow cycling as measured by their ability to retain the labeled DNA for a much longer period than the rapid cycling progenitor cells. However, it is still not completely undisputed that LRCs are stem cells (Kiel et al. Nature, 2007, 449:238-42).

Doetsch et al., (Cell, 1999, 97:703-716), Ohlstein and Spradling, (Nature, 2006, 439:470-474), Palmer et al., (Mol. Cell Neurosci., 1997, 8:389-404) and Sanai et al., (Nature, 2004, 427:740-744) have used in vivo lineage tracing to search for cells that give rise to the downstream lineages to identify neural stem cells and Drosophila gut stem cells were identified.

Kim et al., (Cell, 2005, 121:823-835) have relied on the identification of multipotent cells, as revealed by their co-expression of multiple downstream lineage markers of stem cells. In this way, lung stem cells were identified as bronchio-alveolar stem cells (BASCs) based on their co-expression of two downstream Clara and Alveolar lineage markers, CCA and SP-C, and their ability to give rise to Clara and Alveolar lineages.

The ability of stem cells to express certain types of multiple drug-resistant genes and display a unique pattern in flow cytometry assay has also been used to identify the so-called side population (SP). SP has been shown to be enriched with HSCs (Goodell et al., 1997, Nature Medicine, 3:1337-1345) and stem cells in other non-hematopoietic tissues (Goodell et al., Methods Mol. Biol., 2005, 290:343-352).

Additionally, several methods for the identification of adult stem cells have been developed based on functional characteristics of stem cells such as binding to soybean agglutinin (Reisner et al., 1982, Blood 59:360-363), resistance to the treatment of either 5-fluorouracil (Gordon et al., 1985, Leukemia research 9:1017-1021 and Berardi et al., Science 1995267:104-108) or alkylating agent (Sharkis et al., 1997, Stem cells (Dayton, Ohio) 15 Suppl 1, 41-44; discussion 44-45) and density-gradient (Juopperi et al., 2007, Experimental hematology, 35:335-341).

WO07124125 describes a method for the identification of stem cells wherein a cell population is treated with a DNA damaging agent, which results in the quiescent stem cells residing on the tissue become activated in order to replenish lost cells. These cells can be detected using a marker of DNA biosynthesis.

Thus, there is a need in the art for additional methods for the determination of telomere length and for methods for the identification of stem cell compartments within adult tissues which overcome the disadvantages of the methods known in the art as well as which are generally applicable to any tissue.

SUMMARY OF THE INVENTION

In a first aspect, the invention relates to a method for the determination of the telomere length of a cell in an immobilised tridimensional test cell population comprising
(i) contacting said test cell population and at least two homogeneous immobilised control cell populations of known and stable telomere length and having different average telomere lengths with a probe that hybridises specifically to a repeat region within telomeric DNA and which is labelled with a first fluorescent dye under conditions allowing the probe to hybridise in situ to its complementary target sequences on telomeres,
(ii) determining the average fluorescence intensities in the cell of said test cell population and the average fluorescence intensity value of the cells within each control cell population in response to a radiation adequate to excite the fluorescent dye attached to said probe wherein the determination of the fluorescence signal in the cells is carried out on an image of the cells obtained by fluorescence microscopy on a section of said tissue sample or preparation of immobilised cells and
(iii) assigning to the cell within the test cell population an average telomere length value, wherein said value is the average telomere length of a cell within a control cell population showing an average cellular fluorescence intensity value substantially identical to the fluorescence intensity values of the cell within the cell population as determined by interpolation.

In a second aspect, the invention provides a method for the identification of stem cells in a cell population which comprises
(i) contacting said cell population with a probe that hybridises specifically to a repeat region within telomeric DNA and which is labelled with a first fluorescent dye under conditions allowing the probe to hybridise in situ to its complementary target sequences on telomeres,
(ii) determining the average fluorescence intensities of each cell within a representative sample of in the cells of within said cell population in response to a radiation adequate to excite the fluorescent dye attached to said probe
wherein those cells within the sample showing the highest average fluorescence intensity are identified as stem cells.

In a third aspect, the invention provides a method for the identification of stem cells in a test cell population which comprises
(i) contacting said test cell population and at least two homogeneous control cell populations of known and stable telomere length and having different average telomere lengths with a probe that hybridises specifically to a repeat region within telomeric DNA and which is labelled with a first fluorescent dye under conditions allowing the probe to hybridise in situ to its complementary target sequences on telomeres,
(ii) determining the average fluorescence intensities in each cell of a representative sample of cells within each cell of said test cell population and the average fluorescence intensity value of the cells within each control cell population in response to a radiation adequate to excite the fluorescent dye attached to said probe and
(iii) assigning to each cell within the representative sample of the test cell population an average telomere length value, wherein said value is the average telomere length of a cell within a control cell population showing an average cellular fluorescence intensity value substantially identical to the fluorescence intensity values of the cell within the cell population as determined by interpolation
wherein those cells showing the highest telomere length value are identified as stem cells.

In a fourth aspect, the invention provides a method for the identification of compounds capable of triggering mobilisation of stem cells within a tissue having a known spatial distribution of stem cells comprising the steps of
(i) contacting said tissue sample with a candidate compound under conditions adequate for promoting mobilisation of the stem cells within said tissue,
(ii) contacting a sample of said tissue with a probe that hybridises specifically to a repeat region within telomeric DNA and which is labelled with a first fluorescent dye under conditions allowing the probe to hybridise in situ to its complementary target sequences on telomeres and
(iii) determining the average fluorescence intensity of a representative sample of cells the cells present in the region of the tissue sample known to contain the stem cells
wherein a decrease in the average fluorescence intensity in the area which is known to comprise stem cells when compared to a sample which has not been treated with the candidate compound is indicative that the compound is capable of triggering mobilisation of stem cells within the tissue sample.

In a fifth aspect, the invention provides a method for the identification of compounds capable of triggering mobilisation of stem cells within a tissue having a known spatial distribution of stem cells comprising the steps of
(i) contacting said tissue with a candidate compound under conditions adequate for promoting mobilisation of the stem cells within said tissue,
(ii) contacting said tissue and at least two homogeneous control cell populations of known and stable telomere length and having different average telomere lengths with a probe that hybridises specifically to a repeat region within telomeric DNA and which is labelled with a first fluorescent dye under conditions allowing the probe to hybridise in situ to its complementary target sequences on telomeres,
(iii) determining the average fluorescence intensities of the cells a representative sample of cells present in the region of the tissue sample known to contain the stem cells and an average fluorescence intensity value of the cells within each control cell population in response to a radiation adequate to excite the fluorescent dye attached to said probe and
(iv) assigning to each cell within the representative sample of cells present the region of the tissue sample known to contain the stem cells an average telomere length value, wherein said value is the average telomere length of a cell within a control cell population showing an average cellular fluorescence intensity value identical to the fluorescence intensity values of the cell within the cell population as determined by interpolation
wherein a decrease in the average telomere length in the area in the cells within the region of the tissue known to comprise stem cells when compared to a sample which has not been treated with the candidate compound is indicative that the compound is capable of triggering mobilisation of stem cells within the cell population.

In a sixth aspect, the invention relates to an array comprising at least two immobilised three-dimensional cell populations being each cell population physically separated from the other(s) and wherein each cell population has a stable and known telomere length which is different to the average telomere length of the other cell population(s) of the array.

In a seventh aspect, the invention relates to a method for determining the telomere length of a cell within a tridimensional cell population from a collection of at least two fluorescence microscopy images obtained using a fluorescently-labeled telomere-specific probe and corresponding to different focal planes of said cell population comprising the steps of:

(i) converting the at least two fluorescence microscopy images corresponding to different focal planes into a single image by adding up the fluorescence intensities at each position within the image, (ii) determining the average fluorescence intensity of said cell within the image of the cell population obtained in step (ii) and (iii) assigning to said cell an average telomere length value, wherein said value is obtained by interpolation of the average intensity of the cell within a data set of telomere length values and corresponding fluorescence intensity values obtained from different cell populations of known and stable telomere length processed by fluorescence microscopy in parallel to the cell of the test cell population.

In a eighth and ninth aspect, the invention relates to a computer program including encoded means to carry out the steps of the methods according to the invention and a computer-readable support comprising encoded means adapted to carry out the steps of the methods according to the methods of the invention.

Other aspects of the invention may be apparent upon further reading of the specification and claims of the patent application.

BRIEF DESCRIPTION OF THE FIGURES

FIG. 1C. Upon TPA treatment, wild-type epidermal cells showing the longest telomeres localized not only to the hair follicle stem cell compartment (hair bulge) but also to the transit-amplifying (TA) compartments (hair bulb and infundibulum). In contrast, this enrichment of cell with long telomeres to the TA compartments was abolished in TPA-treated G1 Terc$^{-/}$ skin. FIG. 1D. Absolute number of cells showing an average telomere fluorescence between 1800-3000 a.u. per indicated skin compartment±standard deviation (SD). A total of 3 skin sections per mouse out of a total of 2 mice per genotype were used for quantification the number of cells per skin compartment and standard deviation. n=total number of cells of each compartment used for the analysis (6 independent hair follicle images were counted). FIG. 1E. Absolute total number of epidermal cells per skin section with telomere fluorescence between 1800-3000 a.u.±SD. Note that TPA induces a net telomere elongation in wild-type epidermis, which is abolished in the absence of telomerase activity in G1 Terc$^{-/-}$ skin. A total of 6 skin sections per genotype and condition were used for quantification purposes. n=total number of cells in the epidermis included for the analysis. Statistical significant is indicated for each comparison on top of the bars.

FIG. 2A. Representative telomere length pseudo-color images of 2 month-old wild-type tail skin from a FVB genetic background. Nuclei are coloured according to their average telomere fluorescence in arbitrary units (a.u.). The different epidermal compartments are indicated and separated from the dermis (not studied here) by a dashed line. Asterisk indicates the sebaceous glands. Scale bars correspond to 50 μM. Note the specific enrichment of cells with the longest telomeres at the hair bulge area (the known hair follicle stem cell niche) Left panel shows the percentage of cells showing a given telomere fluorescence within the indicated epidermal compartment. A total of 3 skin sections per mouse out of 2 mice were used for quantification of percentage of cells and standard deviation. n=total number of cells within the indicated compartment used for the analysis. FIG. 2B. Telomere length frequency histograms for cells located in the indicated skin compartments. n=number of nuclei per compartment analyzed for telomere FISH. Statistical significance values are indicated.

FIG. 3A. Quantification of centromere fluorescence in different skin compartments with a PNA major satellite probe. Representative major satellite Cy3 fluorescence of wild-type tail skin. The different epidermal compartments are indicated and separated from the dermis by a dashed line. Asterisk indicates the sebaceous glands. Scale bars correspond to 50 μM. Quantification of major satellite fluorescence signal in different compartments is shown in the right panel. No statistically significant differences in centromere fluorescence were detected between the different skin compartments, therefore ruling out that differences in "probe accessibility" or ploidy may explain the differences in telomere length described here. Five independent skin sections were used for the analysis. n=total number of nuclei per skin compartment used for the analysis. FIG. 3B. Nuclear size is shown for the indicated skin compartments. Note that no major differences are observed between the hair bulge (stem cell compartment) and the more differentiated interfollicular epidermis and infundibulum compartments, which cannot explain the telomere length differences described in FIG. 1A more marked decreased in nuclear size was detected in the hair bulge compartment, which did not reach statistical significance. A total of 8 independent skin sections were used for the analysis. n=total number of cells analysed for the indicated compartment. FIG. 3C. Quantification of centromere fluorescence in different testis compartments with a PNA major satellite probe. Representative major satellite Cy3 fluorescence of wild-type testis. The different testis compartments are indicated and separated by a dashed line. Scale bars correspond to 200 µM. Quantification of major satellite fluorescence signal in different compartments is shown in the right panel. No statistically significant differences in centromere fluorescence were detected between the different testis compartments, therefore ruling out that differences in "probe accessibility" or ploidy may explain the differences in telomere length described here. Five independent testis sections were used for the analysis. n=total number of nuclei per testis compartment used for the analysis.

FIG. 4A. Telomere fluorescence obtained by telomapping or conventional Q-FISH in the indicated skin compartments was represented relative to that of the hair bulge (100%). FIG. 4B. Note a very significant correlation between the telomere length values obtained with telomapping and conventional Q-FISH.

FIG. 5A. Telomere fluorescence obtained by telomapping of a paraffin-embedded array of the indicated human and mouse cell lines. In parenthesis is shown the known telomere length of these cell lines as determined by conventional Q-FISH on metaphases (Canela et al., 2007). Note that the telomapping technique is able to detect differences of telomere length of less than 1 Kb (P<0.001 when comparing HeLa to HeLa2 cell line). FIG. 5B. Calibration curve to convert telomapping arbitrary units of fluorescence into kilobases. Note the linear correlation between both techniques. FIG. 5C. Average telomere length expressed in kilobases of the different mouse skin compartments as determined by telomapping and calibrated using the calibration curve shown in part (c). Note a decrease of telomere length of all the skin compartments compared to the hair bulge (stem cell compartment). n=total number of nuclei analyzed per compartment. Statistically significant differences between compartments are also indicated. To better assess differences in telomeric signal, maximum projections of 16-bits confocal images were obtained from cell line microarray and tail skin paraffin sections.

FIG. 7A. Quantification of size and number of macroscopic colonies obtained from 1×10$^4$ GFP$^+$ and GFP$^−$ purified keratinocytes from three independent 1-year-old K5-EGFP mice and cultured for 10 days on J2-3T3 mitomycin-C-treated feeder fibroblasts. Note that GFP$^+$ cells form 3 times more colonies than GFP$^−$ cells. FIG. 7B. Quantification of size and number of macroscopic colonies obtained from total keratinocytes (unsorted) from three independent 1-year-old K5-EGFP mice and cultured for 10 days on J2-3T3 mitomycin-C-treated feeder fibroblasts. The percentage of colonies that are GFP-positive within each colony size range is indicated.

FIG. 8A. Representative DAPI and Cy3 images of GFP+ and GFP− FACS-sorted keratinocytes from K15-EGFP mice. FIG. 8B. Histograms showing telomere fluorescence frequencies on interphase nuclei as determined by Q-FISH. Average telomere fluorescence and standard deviation are indicated. Differences in telomere length between GPF+ and GFP− cells were highly significant (P<0.001). n=number of nuclei used for the Q-FISH analysis from 2 independent K15-EGFP mice. The red lines highlight the increased frequency of long telomeres in GFP-positive cells. FIG. 8C. Number of telomere spots per nuclei in sorted GFP+ and GFP− cells, indicate that there are no differences in ploidy between these two populations. FIG. 8D. Representative DAPI and Cy3-centromeric images of GFP+ and GFP− FACS-sorted keratinocytes from K15-EGFP mice. FIG. 8E. Quantification of major satellite fluorescence signal in sorted GFP+ and GFP− cells. No significant differences in centromere fluorescence were detected between both cells populations, therefore ruling out that differences in "probe accessibility" or ploidy may explain the differences in telomere length described in FIG. 2b. Two independent mice were used for the analysis. n=total number of nuclei used for the analysis. FIG. 8F. Average telomere length in kilobases of purified GFP-positive and GFP-negative cells from 0.5 and 1.5 year-old K15-EGFP mice as determined by Flow-FISH. A previous immunostaining against GFP was performed to allow identification of cells according to their GFP expression (Experimental Procedures). Bars indicate standard errors, "n" is the number of cells analyzed per condition. Statistical significance calculations are indicated and were obtained with Kolmogorov-Smirnov tests. FIG. 8G. Telomere length as determined by TRF in sorted GFP− (a population enriched in differentiated cells) and GFP+ tail skin keratinocytes (a population enriched in stem cells) from K15-EGFP mice. Note increased TRF size in GFP+ hair bulge cells compared to GFP− cells. FIG. 8H. Telomerase TRAP activity of purified GFP+ and GFP− keratinocytes from K15-EGFP mice. The protein concentration tested is indicated. Samples were pretreated (+) or not (−) with RNase. An internal control (IC) for PCR efficiency was included (Experimental Procedures). HeLa cells are shown as a positive control for telomerase activity.

FIG. 9A. Simultaneous detection of GFP and telomere fluorescence in K15-EGFP back skin. The different epidermal compartments are indicated and separated from the dermis (not studied here) by a dashed line. Right panels show confocal images corresponding to Alexa488 fluorescence (GFP immunostaining) and the combined DAPI+GFP image. Note that GFP-expressing cells localize to the bulge area of the hair follicle, the known putative stem cell niche. Left panels show topographic telomere length maps generated according to GFP status: all nuclei, GFP$^−$ nuclei, and GFP$^+$ nuclei. Nuclei are coloured according to their average telomere fluorescence in arbitrary units (a.u.). GFP-positive cells at the hair bulge showed the longest telomeres. Scale bars correspond to 50 µm. FIG. 9B. Telomere fluorescence frequency histograms according to GFP status in back and tail skin hair follicles from K15-EGFP mice. Differences in telomere length between GPF+ and GFP− cells were highly significant (P<0.001) both in the back and tail skin. Average telomere fluorescence and standard deviation are indicated. n=number of nuclei analyzed. Four-to-six skin sections of either tail or back skin from a total of 2 mice were analyzed. The red lines highlight the increased frequency of long telomeres in GFP-positive cells. FIG. 9C. Percentage of cells with the longest telomeres (red cells after telomapping) or with the shortest telomeres (green colour after telomapping) that are either GFP+ or GFP−. Note that GFP+ cells are enriched in the population of the cells with the longest telomeres.

FIG. 10A. Representative topographic telomere length map of a small intestine histological section generated from confocal telomere Q-FISH images. The different small intestine compartments are indicated. The dashed line separates the epithelial cells (ep) from other cell types not studied here: lamina propia (LP), muscularis mucosa (mm) and submucosa (subm). Scale bar corresponds to 70 μm. Nuclei are coloured according to their average telomere fluorescence in arbitrary units (a.u.). Note that nuclei with the longest telomeres localized above the Paneth cells at the known stem cell niche (positions +4 to +5), as well as in the transient amplifying (TA) compartment (positions above +5). FIG. 10B. Scheme representing the small intestine compartments of villi and Lieberkühn crypts. The crypts are further divided in (i) the Paneth cells at the bottom of the crypt between positions +1 and +3, (ii) the stem cell niche at position +4 to +5, right above the Paneth cells, and (iii) the TA compartment at positions >+5. FIG. 10C. Percentage of cells showing a given telomere fluorescence within the different compartments. The stem cell niche and the TA compartment are enriched in cells with the longest telomeres (red color), while the villi are enriched in cells with the shortest telomeres (green color). Average and standard deviation for the percentages are indicated. A total of 39 crypts and 28 villi from 3 independent mice were quantified. n=number of nuclei per compartment analyzed. Number in parenthesis indicates the cell position in the crypt. FIG. 10D. Telomere length frequency histograms for cells located in the indicated compartments. A remarkable increase in telomere length is observed in stem cells and TA cells compared to Paneth cells and the villi. Average and standard deviation are indicated. A total of 39 crypts and 28 villi from 3 independent mice were quantified. n=number of nuclei per compartment analyzed for telomere FISH. Number in parenthesis indicates the cell position in the crypt. Verticalcoloured lines indicate the different telomere fluorescence ranges. All telomere fluorescence comparisons between the stem cell compartment and the rest of the compartments are highly significant (P<0.001), except significant (P<0.05) for comparison between the stem cell compartment and the TA compartment. FIGS. 10E-10G. Right panels show representative telomere length pseudo-colour images of histological sections from cornea (e), testis (f) and brain hippocampus (g) of wild-type mice. Nuclei are coloured according to their average telomere fluorescence in arbitrary units (a.u.). Scale bars correspond to 200 μM. Magnifications are shown of cornea and brain sections for clarity purposes. Note that cells with the longest telomeres localize preferentially within the described stem cell compartment of each organ. Middle panels show the percentage of cells containing a given telomere fluorescence within each epidermal compartment. Right panels show telomere fluorescence histograms of nuclei in each compartment. Average telomere fluorescence and standard deviation are indicated. The red lines highlight the increased frequency of cells with long telomeres in the analyzed stem cell compartments. A total of 6 different images from each organ from 3 independent mice were used for quantification purposes. CB: ciliary body, L: lens, SGZ: subgranular zone, GCL: granular cell layer, H: hilius, CA: pyramidal cell layers. All telomere fluorescence comparisons between each of the stem cell compartments and the corresponding differentiated compartment are highly significant (P<0.001).

FIGS. 11A and 11B. Representative telomere length pseudo-color images of different age wild-type (a) and third generation telomerase-deficient (G3 Terc−/−) tail skin (b). Nuclei are coloured according to their average telomere fluorescence in arbitrary units (a.u.). The different epidermal compartments are indicated and separated from the dermis (not studied here) by a dashed line. Asterisk indicates the sebaceous glands. Scale bars correspond to 50 μM. Note the decrease in cells with the longest telomeres at the hair bulge area (the known hair follicle stem cell niche) in wild-type mice with increasing age, as well as in 6 month-old G3 telomerase-deficient mice. Right panels show the percentage of cells showing a given telomere fluorescence within the indicated epidermal compartment. A total of 2 skin sections per mouse out of 3 mice per genotype were used for quantification of percentage of cells and standard deviation. n=total number of cells within the indicated compartment used for the analysis. FIG. 11C. Telomere length frequency histograms for cells located in the indicated compartments in mice of the indicated age and genotype. Notice statistically significant telomere shortening in wild-type mice in all the different skin compartments when comparing 2 month old to 2 year old mice, including the hair bulge where the stem cells are located. A third generation G3 Terc-deficient mouse is shown for comparison. n=number of nuclei per compartment analyzed for telomere FISH. Statistical significance values are indicated in the Figure. FIG. 11D. Average telomere fluorescence in the indicated stem cell compartments at the indicated age. Note a faster rate of telomere loss at >1 year or age. FIG. 11E. Average telomere fluorescence in the indicated differentiated compartments of different tissues at the indicated age. Note a faster rate of telomere loss at >1 year or age.

DETAILED DESCRIPTION OF THE INVENTION

Figure 1A:
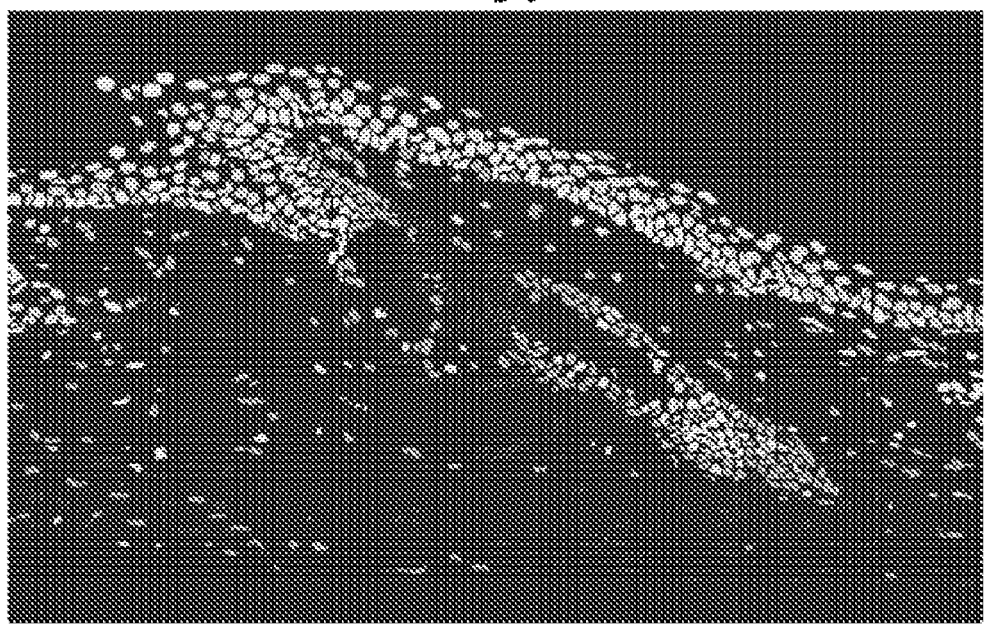
FIGS. 1A-1E. Cells with the longest telomeres are enriched at the hair follicle stem cell compartment and show stem cell behaviour upon treatment with mitogenic stimuli. Representative telomere length pseudo-color images of "resting" wild-type FIG. 1A and first generation telomerase-deficient (G1 Terc$^{-/-}$) tail skin FIG. 1B. Nuclei are coloured according to their average telomere fluorescence in arbitrary units (a.u.). The different epidermal compartments are indicated and separated from the dermis (not studied here) by a dashed line. Asterisk indicates the sebaceous glands. Scale bars correspond to 50 μM. Note the specific enrichment of cells with the longest telomeres at the hair bulge area (the known hair follicle stem cell niche) in both wild-type (telomerase-competent) and telomerase-deficient mice. Bottom panels show the percentage of cells showing a given telomere fluorescence within the indicated epidermal compartment. A total of 3 skin sections per mouse out of 2 mice per genotype were used for quantification of percentage of cells and standard deviation. n=total number of cells within the indicated compartment used for the analysis.
Figure 1A:
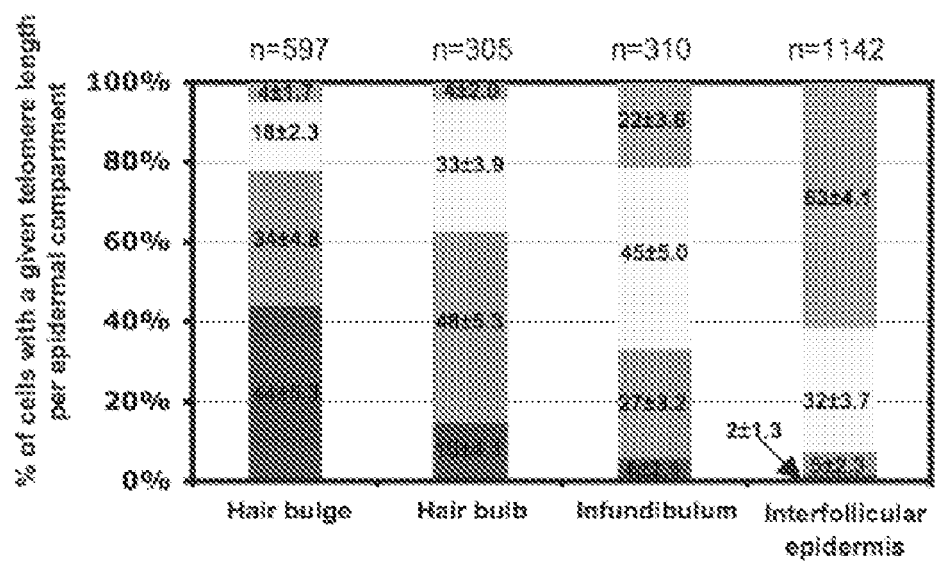

Determination of Telomere Length on Immobilised Cell Populations

The authors of the present invention have shown that, unexpectedly, it is possible to determine the telomere length of every single cell in an immobilized tridimensional cell population using fluorescence microscopy on said cell population followed by a semi-automatic image analyses. By processing in parallel the sample under study and a preparation of different cell types of known and stable telomere length which are different between them, it is possible to obtain a standard curve establishing a correspondence between arbitrary fluorescence units and telomere length. By interpolating within the standard curve the arbitrary fluorescence values of the cells of the sample under study, it is possible to obtain an average telomere length for each cell. For instance, example 1 describes the determination of telomere length in a cell population and the ability of the method developed by the inventors to detect differences of telomere length of less than 1 kb.

Thus, in a first aspect, the invention relates to a method (hereinafter, first method of the invention) for the determination of the telomere length of a cell in an immobilised tridimensional test cell population comprising (i) contacting said test cell population and at least two homogeneous immobilised control cell populations of known and stable telomere length and having different average telomere lengths with a probe that hybridises specifically to a repeat region within telomeric DNA and which is labelled with a first fluorescent dye under conditions allowing the probe to hybridise in situ to its complementary target sequences on telomeres, (ii) determining the average fluorescence intensities in a cell of said test cell population and the average fluorescence intensity value of the cells within each control cell population in response to a radiation adequate to excite the fluorescent dye attached to said probe wherein the determination of the fluorescence signal in the cells is carried out on an image of the cells obtained by fluorescence microscopy on a section of said tissue sample or preparation of immobilised cells and (iii) assigning to the cell within the cell population an average telomere length value, wherein said value is the average telomere length of a cell within a control cell population showing an average cellular fluorescence intensity value substantially identical to the fluorescence intensity values of the cell within the cell population as determined by interpolation.

The expression "tridimensional cell population", as used herein, relates to a group of cells with characteristic proportions in particular stages of both the cell cycle and the differentiation program, and having characteristics in common and which are organized so that the cell population extends substantially in all three spatial dimensions, thus excluding dissociated cells in suspension as well as cells immobilized in a two dimensional support. The characteristics include without limitation the presence and level of one, two, three or more cell-associated molecules (e.g., cell-surface antigens). It is understood that a tridimensional cell population, as used herein, includes tissues as well as cells grown in a tridimensional scaffold. In principle, any cell preparation can be analysed using the first method of the invention. In a preferred embodiment, the test cell population is a tissue sample selected from the group of skin, small intestine, testis, cornea and brain wherein said tissues can be normal non-transformed tissues or tumours, either primary or metastatic isolated from each of said tissues.

Step (i) of the first method of the invention requires contacting the test cell population and at least two homogeneous immobilised control cell populations with a probe that binds specifically to the telomere. The probes useful in the present invention are those which are complementary to, or hybridise under stringent conditions, to the DNA sequences which appear in the telomeres. As such, the probes used in the methods of the invention do not substantially cross-react with sequences founds in other regions of the chromosome, including centromeric regions. Accordingly, telomere-specific oligonucleotides may be designed using telomeric sequences that are well known in the art. For example, complete sets of telomeric probes for human chromosomes are described in NIH/IMM Collaboration, (Nature Genetics, 1996, 14:86); Knight et al., (Am. J. Hum. Genet., 2000, 67:320-332); Knight et al., (J. Med. Genet., 2000, 37:401-409) and Veltman et al., (Am. J. Hum. Genet., 2002, 70:1269-1276). Further, complete sets of telomeric probes for human chromosomes may be purchased from Vysis Inc. (Downers Grove, Ill.; as ToTelVysion and TelVysion chromosome-specific telomere probes) and from Open Biosystems (Huntsville, Ala.; as Human Chromosome Telomeric Region Probes).

Probes suitable for use in the present invention include probes specifically directed to the simple tandem repeat $(TTAGGG)_n$. Moreover, the telomeric probes suitable for use in the methods according to the present invention may further comprise a minor groove binder (MGB), a locked nucleic acid (LNA) and/or a peptide nucleic acid (PNA). A "minor groove binder" (MGB) moiety binds to the minor groove of DNA with high affinity. When this minor groove binder is conjugated to one end (the 5'-end or the 3'-end) of short oligodeoxynucleotides, the conjugates form unusually stable hybrids with complementary DNA in which the tethered MGB group resides in the minor groove. A "locked nucleic acid" (LNA) is a RNA derivative in which the ribose ring is constrained by a methylene linkage between the 2'-oxygen and the 4'-carbon. This conformation restriction increases binding affinity for complementarity sequences. A peptide nucleic acid (PNA) is an oligonucleotide analogue in which the sugar phosphate backbone is replaced by a protein like backbone. In PNA, nucleobases are attached to the uncharged polyamide backbone yielding a chimeric pseudopeptide-nucleic acid structure, which is homomorphous to nucleic acid forms. Chimeric DNA-PNA and pure PNA probes can be used to provide stronger binding of the probe. A unique property of the peptide nucleic acid (PNA) probes is their discriminatory advantage due to their increased affinity for DNA, which allows the use of short PNA probes. Moreover, the fluorescence yielded by probe staining is considered to be quantitative due to the fact that PNA binds preferentially to DNA at low ionic salt concentrations and in the presence of formamide, thus the DNA duplex may not reform once it has been melted and annealed to PNA probe, allowing the probe to saturate its target repeat sequence (as it is not displaced from the target DNA by competing anti sense DNA on the complimentary strand), thus yielding a reliable and quantifiable readout of the frequency of PNA probe target at a given chromosomal site after washing away of unbound probe.

In a preferred embodiment, the probe that specifically binds to the telomere is a probe that comprises the sequence (CCCTAA). In a more preferred embodiment, the telomeric probe is a PNA. In a still more preferred embodiment, the telomeric probe is a PNA that comprises the sequence (CCCTAA).

It will be understood that the test cell population which is to be studied according to the method of the present invention and the control cell populations used as standard for telomere length in the method of the present invention must be first permeabilized so as to render the probe accessible to the nuclei of the cells. Means for the permeabilization of cell membranes are known to the skilled person and include treatment with non-ionic detergents and treatment with hydrophobic solvents such a methanol. Preferably, permeabilization is carried out using 100% methanol. Moreover, the cell preparation may also be partially or totally fixed. Fixing can be carried out using any method known in the art such as formaldehyde, paraformaldehyde, acetic acid, acetic acid/methanol mixtures and the like. In addition, the cells may also be treated with protease in order to remove background signal resulting from non-specific binding of the probe to proteinaceous compounds. By way of example, the cells may be treated with pepsine at pH 2 at 37° C.

The hybridization probe is added to the cells into a hybridization medium. The concentration of probe used in the methods described herein may be selected by titrating increasing amounts of the probe and determining the concentrations which provide plateau hybridization. These concentrations are preferably used in the method of the invention. In a preferred embodiment of the invention for visualizing and optionally determining the length of telomere repeats in nucleic acid molecules in morphologically preserved materials, the amount of hybridization probe used is between 0.1-10 µg/ml, preferably 0.3 µg/ml. The hybridization medium and hybridization conditions are selected so as to favour hybridization of the probe with the denatured nucleic acid molecules in the preparation to be tested, and disfavour renaturation of the denatured nucleic acid molecules with their complementary single strand. Generally, a hybridization medium is selected which has a low ionic strength and typically contains a buffer, denaturing agent and blocking reagent. Suitable buffers include Tris and Hepes. Examples of suitable denaturing agents are formamide and DMSO. A blocking reagent is selected so that it substantially blocks non-specific binding of the probe. Examples of blocking reagents which may be used in the method of the invention are protein solutions such as BMP (Boehringer-Mannheim, Gmbh, FRG). In a preferred embodiment of the method of the invention for detecting and/or determining the length of multiple copies of a telomeric repeat in a nucleic acid molecule, the hybridization medium contains a buffer (e.g. 10 mM TRIS, pH=7.2), formamide 50%-100%, most preferably 70% formamide, BMP (1-5% W/V, most preferably 0.25% W/V), and the labelled probe.

The hybridization medium containing the hybridization probe may be applied to the morphologically preserved biological materials. Generally, 5 to 50 µl, preferably 30 µl of the hybridization medium is applied per cell preparation. The hybridization probe is applied and the target nucleic acid molecules are denatured simultaneously by heat or pH treatment, preferably the mixture is treated for 0.1 to 1 hours at 70 to 80° C., most preferably 3 minutes at 80° C. Hybridization is carried out for about 0.1 to 24 hours, most preferably 2 hours, at 4 to 40° C., preferably 25° C. After hybridization, the slides are washed with buffer (e.g. formamide/TBS/Tween).

In the methods of the invention for detecting and/or quantitating multiple copies of a repeat sequence in cell suspensions, about 10 to 1000 µl, preferably 200 µl of hybridization medium is added to the cells. The hybridization is carried out for about 5 min to 24 hours, preferably 8 to 18 hours at room temperature. After hybridization the cells are washed with buffer (e.g. formamide/BSA/Tween; Tris/NaCl/Tween/BSA) and resuspended in buffer (e.g. PBS and 7AAD for FACSort; DAPI for FACStar).

The telomeric probe is labelled with a fluorescent dye which allows detecting the telomere-associated fluorescence. Any fluorescent dye known in the art can be used for the purposes of the present invention as long as suitable filters to select excitation and emission wavelengths are available. By way of example, Table 1 provides a list of possible fluorescence dyes that can be coupled to telomeric-specific probes.

TABLE 1

Commonly used fluorescente dyes

| Molécula | Excitación (nm) | Emisión (nm) |
|---|---|---|
| FAM | 488 | 518 |
| HEX | 488 | 556 |
| TET | 488 | 538 |
| CY3 | 550 | 570 |
| CY5.5 | 675 | 694 |
| JOE | 527 | 548 |
| 6-ROX | 575 | 602 |
| Cascade Blue | 400 | 425 |
| Fluoresceína | 494 | 518 |
| Texas Red | 595 | 615 |
| Rodamina | 550 | 575 |
| Rodamina Green | 502 | 527 |
| Rodamina Red | 570 | 590 |
| Rodamina 6G | 525 | 555 |
| 6-TAMRA | 555 | 580 |
| 5-TMRIA | 543 | 567 |
| Alexa 430 | 430 | 545 |
| Alexa 488 | 493 | 516 |
| Alexa 594 | 588 | 612 |
| Bodipy R6G | 528 | 550 |

Step (i) of the first method of the invention involves the simultaneous contacting of the telomeric and, optionally, the centromeric probe with the test cell population and with a series of control cell populations having stable and known telomere lengths. The number of control cell populations that can be used in step (i) varies although it can be appreciated that the highest number of control cell populations that are used, the more accurate will be the correlation between arbitrary fluorescence units and telomere length. However, a minimum of two different control cell populations can be used. It will be appreciated by the person skilled in the art that any cell line which is homogenous, i.e, it consists of essentially a unique cell type, which shows stable telomere length (i.e. the telomere length does not substantially vary during proliferation cycles or in response to different culture conditions) and wherein the average telomere length is know can be used as control cell population in the second method of the invention. By way of example, the cell lines Hela 2, HeLa, MCF7, HeLa S3, 293T, L5178Y-S, MEFs BL6 G3 Terc$^{-/-}$, MEFs BL6 wild type, HeLa 1211, MEFs 129Sv/BL6 wildtype and L5178Y-R are suitable for the purposes of the method of the invention since they meet the requirements mentioned above (see Canela et al., 2007, Proc. Natl. Acad. Sci. USA, 104:5300-5305).

Thus, in a preferred embodiment, step (i) of the first method of the invention is carried out using at least two, at least three, at least four, at least five, at least six, at least seven, at least eight, at least nine, at least ten or at least eleven of the cell populations mentioned above. However, the skilled person will appreciate that the method of the invention is not limited to the use of the particular cell lines mentioned above but that any cell line can be used as long as the above requirements are met. The average telomere length of a cell line, if not previously known, can be determined using standard techniques known to the skilled person such as telomere restriction fragment assay (TRF) (Moyzis et al., 1988, Proc. Natl. Acad. Sci. USA, 85:6622-6626).

In a preferred embodiment, the control cell populations are processed in parallel with the cell population under study. Since the test cell population is a tissue or a cell preparation immobilized in a tridimensional matrix, the control cell populations are also be immobilized so as to process all samples in the same manner. Preferably, the cell populations may be fixed using formaldehyde, paraformaldehyde or acetic acid and then embedded in a proper support so as to form blocks. Media suitable to form blocks containing the control cell populations include gelatine, alginate, chitosan, PLGA, and the like. The blocks are then processed in the same manner as the tissue samples, i.e. by embedding in paraffin, sectioning and inspection by fluorescence microscopy.

Step (ii) of the first method of the invention requires determining the average fluorescence intensity in the cells of the cell population, wherein said fluorescence reflect the number of telomeric repeats and hence, the length of the telomeres. Several ways can envisaged to determine fluorescence intensity in the cells associated to the telomere-specific probe.

Since the cell population is a tissue or a preparation of immobilized cells in a tridimensional matrix (e.g., cells embedded in gelatin), the determination of the fluorescence signal is preferably carried out on an image of the cells obtained by fluorescence microscopy on a section of said tissue sample or said preparation of immobilized cells. In case the sample to be analysed is embedded in paraffin, the tissue must be first deparaffinized prior to the analysis using the methods of the invention. Typically, deparafinisation is carried out by applying sequential washes with an organic solvent (e.g. xylene) and rehydrated using ethanol/water mixtures of decreasing ethanol concentrations (100, 95 and 70%). The invention also contemplates processing in parallel a cell population which is a cell suspension or a monolayer, in which case, said cell preparation must be immobilized in a support which can then be processed as the tridimensional tissue sample. Agents suitable for immobilising cells include gelatine, alginate, agarosa, agar, inuline, carrageenan, polyacrilamide, polystirene, dextran, pectine, carboxymethylcellulose. In a preferred embodiment, the cells are embedded in gelatine. Once the cell population is immobilized in the solid support, the blocks can be processed in the same manner as the tissue sample (paraffin embedding, deparafinisation, rehydration and permeabilisation). In case the cell population is a cell monolayer grown on a support, the cells are first detached from the support and then treated as the cells in suspension. Tissues that can be analysed using the method of the invention include, without limitation, skin, small intestine, testis, cornea and brain.

Image collection is carried out using wave-length filters that allow the excitation of the image using a wave-length specific for the fluorescent dye which is attached to the telomeric probe. Whenever a normalisation probe and/or a fluorescent DNA stain must be simultaneously detected, images from the same filed are captured sequentially using different filter sets for each dye. By way of example, when the cells are labelled with a FITC (telomeric probe), Cy3 (normalization probe) and DAPI (DNA stain), the images are collected using an excitation filter 380/10 nm, dichroic: Fura/FITC and emission 435LP for DAPI visualization, excitation filter 548/20 nm, dichroic: Fura/TRITC and emission: Fura/TRITC for Cy3 detection and excitation filter: 480/10 nm, dichroic: Fura/FITC and emisión: Fura/FITC or 535/50 for FITC detection.

Preferably, when quantification of the telomere-associated fluorescence is to be determined, the images are collected using a confocal microscope. The use of a confocal microscopy allows the elimination of out-of-focus light or flare in specimens that are thicker than the focal plane by the use of a spatial pinhole. By way of a example, in a section of X μm of thickness, confocal microscopy allows collection of ten X/10 μm focal planes which are then combined in a single image adding the intensity of every focal plane.

Confocal microscopes suitable for use in the present invention include, without limitation, confocal laser scanning microscopes, spinning-disk (Nipkow disk) confocal microscopes and Programmable Array Microscopes (PAM).

In order to determine the fluorescence intensity at a single cellular level, the method requires first to define the regions within the image that correspond to cell nuclei. These regions are used then to define a mask which is applied to the fluorescence image derived from the telomere-specific probes to obtain a combined image with telomere fluorescence information for each nucleus. The average fluorescence in the nuclear area is then normalized to the nuclei area, thus providing a value of "average gray values" (total gray value/nuclei area) units (arbitrary units of fluorescence). This method allows the determination of the average fluorescence intensity for the total nuclear area, thus excluding that differences in nuclear size may influence telomere length measurements. Preferably, the regions within the image corresponding to the cell nuclei are selected by visualization with a fluorescent DNA dye. Exemplary nuclear stains include, for example, DAPI, Hoechst 33342 dye, 7-actinomycin-D, 7-Aminoactinomycin D, Chromomycin A3, propidium iodide, Nuclear fast red or LDS751. The skilled person will appreciate that the DNA dye must emit at a wavelength which allows the capturing of the telomere fluorescence without interference from the DNA fluorescence. Preferably, the telomere-specific probe is labeled with Cy3 and the DNA is labeled with DAPI.

Once the fluorescence has been determined on the immobilized cell preparation, the fluorescence signal may be influenced by changes in nuclear size and differences in ploidy. Therefore, the signal obtained using telomeric-specific probes must be normalized to an internal control signal control so as to rule out that different values are not due to differences in ploidy as well as in probe accessibility. For this purpose, the invention contemplates the labeling of the cell population with a second probe (hereinafter "the normalization probe") that binds specifically to a region in the cell nuclei which is found in a constant copy number. Preferably, the normalization probe is a probe which hybridizes specifically to the centromeric DNA and, more in particular, to a unique repetitive sequences found in the centromeric regions of primate chromosomes. For example, the centromeric oligonucleotides may correspond to "alphoid" or "alpha-satellite" DNA, which is present at the centromeric region of every chromosome of an animal cell with a sequence that is different for each chromosome (see, e.g., Lee et al., Human Genet., 1997, 100:291-304 and Jabs et al., Am. J. Hum. Genet., 1987, 41:374-90).

Probes specific for each of the centromeres of all of the human chromosomes may be purchased as "CEP Probes" from Vysis Inc. (Downers Grove, Ill.), or as "Human Chromosome-Specific Centromeric Probes", from Open Biosystems (Huntsville, Ala.). Alternatively chromosome specific centromeric oligonucleotides may be designed using known sequences. For example, the probes discussed in the following publications may be used to design suitable centromeric oligonucleotides for each of the human chromosomes: chromosome 1: Waye et al., (Genomics (1987) 1:43-51); Hardas et al., (Genomics (1994) 21:359-63); Solus et al., (Somat. Cell. Mol. Genet. (1988) 14:381-91); chromosome 2: Ostroverkhova et al., (Am J Med Genet. (1999) 87:217-20; Matera et al., (Hum Mol Genet. (1992) 1:535-9); chromosome 3: Delattre et al., Hum Hered. (1988) 38:156-67; Varella-Garcia et al., (Cancer Res. (1998) 58:4701-7); chromosome 4: Grimbacher et al., (Genet. Med. (1999) 1:213-8); chromosome 5: Matera et al., (Genomics (1993) 18:729-31); Reichenbach et al., (Am. J. Med. Genet. (1999) 85:447-51) chromosome 6: Lastowska et al., Cancer Genet. Cytogenet. (1994) 77:99-105); chromosome 7: Mark et al., (Exp Mol Pathol. (1999) 67:109-17); Zhao et al. (Ann. Clin. Lab. Sci. (1998) 28:51-6); Jenkins et al., (Cancer Res. (1998) 58:759-66); chromosome 8: Zhao et al., (Ann. Clin. Lab. Sci. (1998) 28:51-6); Macoska et al., (Urology (2000) 55:776-82); Mark et al., (Exp. Mol. Pathol. (1999) 66:157-62); chromosome 9: Rocchi et al., (Genomics (1991) 9:517-23); Gutierrez-Angulo et al., (Genet Couns. (2001) 12:359-62); chromosome 10: Wang et al., (Somat. Cell Mol. Genet. (1996) 22:241-4); Devilee et al., (Genomics (1988) 3:1-7); Howe et al., (Hum Genet. (1993) 91:199-204); chromosome 11: Voorter et al., (Int. J. Cancer (1996) 65:301-7); Kraggerud et al., (Cancer Genet. Cytogenet. (2003) 147:1-8); chromosome 12: Looijenga et al., (Cytogenet. Cell Genet. (1990) 53:216-8); Zhao et al., (Ann. Clin. Lab. Sci. (1998) 28:51-6); chromosome 13: Warren et al., (Genomics (1990) 7:110-4); chromosome 14: Earle et al., (Cytogenet Cell Genet. (1992) 61:78-80); chromosome 15: Stergianou et al., (Hereditas (1993) 119:105-10); chromosome 16: Greig et al., (Am. J. Hum. Genet. (1989) 45:862-72); chromosome 17: Fink et al., (Hum Genet. (1992) 88:569-72); chromosome 18: Verma et al., (Ann Genet. (1998) 41:154-6); chromosome 19: Hulsebos et al., (Cytogenet. Cell Genet. (1988) 47:144-8); chromosome 20: Meloni-Ehrig et al., Cancer Genet. Cytogenet. (1999) 109:81-5); chromosome 21: chromosome 21: Maratou et al., (Genomics, 1999, 57:429-32); Verma et al., (Clin. Genet. (1997) 51:91-3); X chromosome: Yang et al., (Proc. Natl. Acad. Sci. (1982) 79:6593-7); Crolla et al., (Hum. Genet. (1989) 81:269-72); and Y chromosome: Davalos et al., (Am. J. Med. Genet. (2002) 111:202-4); Rivera et al., (Ann. Genet., 1996, 39:236-9); Tho et al., (Am. J. Obstet. Gynecol. (1988) 159:1553-7). In a preferred embodiment, the centromeric probe comprises the sequence TCGCCATATTCCAGGTC (SEQ ID NO:1).

As the telomeric probe, the normalization probe may be an oligonucleotide, a locked nucleic acid (LNA) and/or a peptide nucleic acid (PNA) and may be attached to a minor groove binder (MGB). Centromeric probes suitable for use in the present invention are known in the art.

The skilled person will appreciate that the normalization probe must be labeled with a fluorescent dye so that the probes are suitable for normalization of the fluorescence emitted by the telomeric probe. It will be appreciated that dyes as described in Table 1 are suitable for labeling the centromeric probe. However, since the centromeric and the telomeric probes are to be used in the same samples, the centromeric probe must contain a label which can be detected without interfering with the fluorescence produced by the telomere probe. Suitable combinations of markers that can be applied to the centromeric and telomeric probes to allow individual detection of the fluorescence emitted by each of them include FITC and Cy3, Cy3 and rhodamine, FITC and rhodamine, AMCA and FITC, AMCA and TRICT, FITC and TRITC, FITC and R-PE, R-PE and PE-Cy5, Cy2 and PE- Texas Red, Cy2 and PE-CY5.5, PE-Texas Red and PE-CY5.5, Alexa 488 and Cy3, Alexa 488 and PE-Alexa647, Cy3 and PE-Alexa647, Cy3 and FITC, Cy3 and Cy5, FITC and Cy5, FITC and coumarine and the like.

The second labeling can be carried out at the same time, prior or after the labeling with the telomeric-specific probes.

Step (iii) according to the first method of the invention requires converting the average fluorescence intensity obtained from the cells to an average telomere length value. This step is preferably carried out by interpolation. As used herein, "interpolation" means the process of calculating a new point between two existing data points. The interpolation process comprises comparing the average fluorescence intensity in a given cell within the population under study with a data set which contains at least two pairs of fluorescence/telomere length values obtained from the control cell populations processed in parallel. The skilled person will appreciate that many methods exist for the interpolation of a given fluorescence value within a correspondence table reflecting telomere lengths as a function of fluorescence intensity. By way of example, the interpolation can be carried out using methods such as piecewise constant interpolation (also known as nearest neighbour interpolation), linear interpolation, polynomial interpolation, spline interpolation, rational interpolation, trigonometric interpolation, bilinear interpolation, bicubic interpolation and the like. As it will be appreciated, the accuracy of the interpolation method will depend on the number of values included in the standard data set, although it is possible to carry out an interpolation with only a single pair of values. Preferably, the interpolation is carried out using a data set comprising at least three, at least four, at least five, at least six, at least seven, at least eight, at least nine, at least ten, at least eleven pairs of values. The results of the interpolation applied to each cell within the cell population under study will provide an average telomere length of each cell.

Identification of Stem Cells using Telomere-Dependent Fluorescence Intensity Values Moreover, the authors of the present invention have shown that, surprisingly, telomere length can be used to identify those compartments within tissues that comprise stem cells. Without wishing to be bound by any theory, it is believed that the possibility of identifying stem cells within a cell population lies in the fact that, contrary to most somatic cells, stem cells contain certain telomerase activity but rarely divide and are found in protected microenvironments or niches. Thus, despite the fact that they suffer telomere shortening, the presence of telomerase activity results in that the telomere length decreases more slowly that the rest of somatic cells. Thus, in a given tissue, there are differences in telomere length between stem cells and the rest of somatic cells, being telomeres longer in stem cells than in somatic cells.

The assay is advantageous over the assays known to date because it is tissue-independent, i.e. telomere length can be used to identify stem cell niches in every tissue when compared to the methods known in the prior art wherein stem cell niches in each tissue had to be carried out using markers specific for the tissue (e.g. CD34 and keratin 15 in hair follicle). As shown in the experimental part (example 2), telomere length has been used to identify stem cell compartments in the hair follicle, confirming the known location of the stem cell niche in the hair follicle bulge. Moreover, the assay has been validated studying other tissues wherein the location of the stem cell niche is known. For instance, telomere length according to the assay of the invention confirms the bottom of the intestinal crypts as the location wherein the stem cell niche is found in intestine (example 4), the limbus as the location wherein the stem cell niche of the cornea is found (example 4) and the periphery of the seminiferous tubes as the location wherein the stem cell niche in testis is found (example 4).

Thus, in a second aspect, the invention relates to a method for the identification of stem cells in a cell population which comprises
(i) contacting said cell population with a probe that hybridises specifically to a repeat region within telomeric DNA and which is labelled with a first fluorescent dye under conditions allowing the probe to hybridise in situ to its complementary target sequences on telomeres,
(ii) determining the average fluorescence intensities of each cell within a representative sample of cells within said cell population in response to a radiation adequate to excite the fluorescent dye attached to said probe
wherein those cells within the sample showing the highest average fluorescence intensity are identified as stem cells.

"Stem cells", as used herein, relate to cells derived from adult tissues, i.e. they are non embryonic stem (ES) cells or non embryonal germ (EG) cells, that have extensive proliferation potential and are capable of differentiating into most specialized cell types present in the tissue wherein they are found, i.e. they are pluripotential. In contrast to ES or EG cells, which are able to differentiate into cells of the three major lineages (ectodermal, enodermal and mesodermal), adult stem cells are usually limited in their differentiation capabilities to the lineage of the tissue wherein they are found. Typical adult stem cells which can be identified using the methods of the present invention include, without limitation:

Haematopoietic stem cells, giving rise to all the types of blood cells: red blood cells, B lymphocytes, T lymphocytes, natural killer cells, neutrophils, basophils, eosinophils, monocytes, macrophages, and platelets, Bone marrow stromal cells (mesenchymal stem cells), giving rise to a variety of cell types including osteocytes, chondrocytes, adipocytes as well as other kinds of connective tissue cells such as those in tendons, Neural stem cells in the brain give rise to its three major cell types: neurons), astrocytes and oligodendrocytes, Intestine stem cells giving rise to absorptive cells, goblet cells, Paneth cells, and enteroendocrine cells and Epidermal stem cells which occur in the basal layer of the epidermis and at the base of hair follicles. The epidermal stem cells give rise to keratinocytes. The follicular stem cells can give rise to both the hair follicle and to the epidermis, Testicular stem cells,
Mammary stem cells
Cardiac stem cells
Pituitary stem cells
Cancer stem cells The expression "cell population", as used herein, relates to a group of cells with characteristic proportions in particular stages of the cell cycle and having characteristics in common. The characteristics include without limitation the presence and level of one, two, three or more cell-associated molecules (e.g., cell-surface antigens). It is understood that cell population includes tissues, cells grown in culture as well as dissociated cells which may be either in suspension in an appropriate culture medium as well as immobilized in a two dimensional support or in a tridimensional scaffold.

Step (i) according to the second method of the invention requires contacting the cell population with a probe that binds specifically to the telomere. This method is carried out essentially as described for the first method of the invention regarding the telomeric probes, fluorescent dyes, hybridization conditions, pre-treatment of the cells.

Step (ii) of the second method of the invention requires determining the average fluorescence intensity of each cell in a representative sample of the cell population, wherein said fluorescence reflect the number of subtelomeric repeats and hence, the length of the telomeres. "Representative sample", as used herein, refers to a sample of the cell population which contains a subset of the cells of the sample which is large enough to provide a statistically significant representation of all the different cell types within the cell population and which allows to obtain statistically significant information of the whole cell population. The representative sample can comprise as low as 0.001%, 0.01%, 0.1%, 1%, 2%, 3%, 4%, 5%, 6%, 7%, 8%, 9%, 10%, 20%, 30%, 40%, 50%, 60%, 70%, 80%, 90%. The representative sample may be formed by the totality of cells of the cell population.

Several ways can envisaged to determine fluorescence intensity in the cells associated to the telomere-specific probe. In case that the cell population is a tissue or a preparation of immobilized cells (e.g., cells embedded in gelatin), the determination of the fluorescence signal is preferably carried out as described in the first method of the invention regarding treatment of the cells, image collection, type of microscopy, region of the cell used for image collection.

In case that the cell population to be analyzed is a cell suspension, the measurement of the fluorescence signal may be carried out using a fluorescence-activated cell sorter, i.e. a technique known as flow-FISH. Flow-FISH, as originally described by Rufer et al (Nature Biotechnol., 16:743-747), allows the use of a conventional cell sorter to determine telomere length based on the fluorescence emission of cells previously contacted with a telomeric-specific probe. Each flow-FISH experiment begins with the acquisition of the pre-mixed calibration (MESF) beads. Several thousand events are collected, and the mean fluorescence and coefficient of variation (CV) of each of the five peaks is recorded and plotted against the MESF content provided by the manufacturer to control for the linearity of the instrument. CV is defined as the standard deviation (s) of the fluorescent intensity of a population of beads expressed as a proportion or percentage of the mean (m) intensity (CV¼s/m). The next steps are related to the selection of the optimal values for the detectors, amplifiers, fluorescence compensation setting and threshold values for analysis of flow FISH samples. Once appropriate instrument settings have been selected, these can be saved and recalled for future experiments, although minor day-to-day adjustments are typically required between experiments and between samples. The instrument settings are further adjusted to provide a good separation of the events of interest over the entire range in the selected channels. Various compensation settings are selected for the analysis of cells simultaneously labeled with fluorescein, phycoerythrin (PE), LDS751 and Cy-5. Except for the compensation setting for fluorescence 2 channel (Fl2; PE) fluorescence detected in the Fl1 (green fluorescence) channel, the setting for green fluorescence detection is typically not readjusted after the acquisition of the MESF bead data because the range of telomere fluorescence in test cells is typically known. In one embodiment, the cells population to be analyzed is mixed with a second population of cells whose average telomere length is known. The two cells populations can usually be distinguished based on forward light scatter (providing a measure of the cell size), side scatter (providing a measure of the cell complexity) and the intensity of the fluorescence due to the DNA dye since different cell populations usually uptake DNA dyes to different extents. The cell suspension to be analyzed may be permeabilized so as to ensure access of the telomeric probe to the cell nuclei. Permeabilization may be carried out using. e.g. methanol. Moreover, the cell may also be partially or totally fixed. Fixing can be carried out using any method known in the art such as formaldehyde, paraformaldehyde, acetic acid, acetic acid/methanol mixtures and the like. Moreover, the cells may also be treated with protease in order to remove background signal resulting from non-specific binding of the probe to proteinaceous compounds.

Irrespective of whether the fluorescence determination of the cells within the representative sample is carried out by fluorescence microscopy on tissue sections or by flow-FISH on cells on suspension, the fluorescence signal may be influenced by changes in nuclear size and differences in ploidy. Therefore, the signal obtained using telomeric-specific probes must be normalized to an internal control signal control so as to rule out that different values are not due to differences in ploidy as well as in probe accessibility. Normalisation of the signal is carried out essentially as described for the first method of the invention regarding the type of probe that is used and the type of dye to be used.

Once the fluorescence intensity values in each cell of the representative sample is determined and, optionally normalised to the control fluorescence levels and limited to those areas corresponding to the cell nuclei, the cells which show the highest fluorescence values are selected as candidate stem cells within the cell population. The term "highest", when referred to the fluorescence values, relates to those absolute values which are the highest among the cell population under study. The assignation of a cell as having high fluorescence value can be done using the percentile method, which reflects the value of the fluorescence intensity below which a certain percent of observations fall. Percentiles can be calculated as quartiles, wherein the fluorescence values of the whole cell population is divided in four intervals and wherein high fluorescence would correspond to those cells whose fluorescence is found in the upper quartile. Percentiles can also be calculated by dividing the fluorescence values of the whole cell population in two groups with respect to a threshold level (the median) and wherein the cells showing high fluorescence value would be those cells whose fluorescence is above said median value.

Identification of Stem Cells Based on Telomere Length

The authors of the present invention have also improved the method for the identification of the stem cells by including an additional step in the identification method wherein the arbitrary values of fluorescence intensity obtained from the images are correlated with average telomere lengths. In this way, the identification of the stem cell in a sample is carried out based on the average telomere length of the cell rather than on the fluorescence intensity. As it can be seen in the experimental section, longer telomere length values appear in cells present in compartments which were known to correspond to the stem cell niche in hair follicles (example 3), intestine (example 4), cornea (example 4) and testis (example 4). By processing in parallel the sample under study and at least two preparations of cells of known and stable telomere length and showing different telomere length, it is possible to obtain a standard curve between arbitrary fluorescence units and telomere length. By interpolating within the standard curve the arbitrary fluorescence values of individual cells of the sample under study, it is possible to obtain an average telomere length for each cell. The cells showing the largest telomere lengths are then the candidate stem cells in the tissue under study. The use of a standard curve allows the detection of small differences in telomere length (1 kb). Thus, in another aspect, the invention relates to a method (hereinafter "third method of the invention") for the identification of stem cells in a test cell population which comprises
- (i) contacting said test cell population and at least two homogeneous control cell populations of known and stable telomere length and having different average telomere lengths with a probe that hybridises specifically to a repeat region within telomeric DNA and which is labelled with a first fluorescent dye under conditions allowing the probe to hybridise in situ to its complementary target sequences on telomeres,
- (ii) determining the average fluorescence intensities in each cell of a representative sample of cells within said test cell population and the average fluorescence intensity value of the cells within each control cell population in response to a radiation adequate to excite the fluorescent dye attached to said probe and
- (iii) assigning to each cell within the representative sample of the test cell population an average telomere length value, wherein said value is the average telomere length of a cell within a control cell population showing an average cellular fluorescence intensity value substantially identical to the fluorescence intensity values of the cell within the cell population as determined by interpolation wherein those cells showing the highest telomere length value are identified as stem cells.

Step (i) of the third method of the invention is carried out essentially as described in the first method of the invention regarding the probe that hybridises specifically to a repeat region within telomeric DNA, the hybridisation conditions, the normalisation (centromeric) probes and the labelling in parallel of a series of cell populations of stable and known telomere length.

Step (ii) of the third method of the invention is carried out essentially as described in the first method of the invention regarding the conditions suitable for excitation of the fluorescent probes and for determination of the average fluorescence intensity in each cell of the representative sample.

Step (iii) requires converting the average fluorescence intensity obtained from the cells to an average telomere length value and is carried out essentially as described in the first method of the invention.

Once the telomere lengths of the different cells within the representative sample of the test cell population have been determined by the interpolation method carried out in step (iii), the cells showing the highest telomere lengths will then be considered as candidates for being the stem cells within the cell population under study. The telomere length values (expressed in kb) can then be statistically analysed using the same methodology as with the fluorescence intensity values as explained above. Preferably, the distribution of telomere lengths within the cell population is divided in quartiles and the cells whose telomere length is found in the upper quartile are then considered as candidate stem cells.

Screening Methods

The authors of the present invention have also shown that the telomere mapping methods developed in the present invention also allow to monitor the process of mobilization of stem cell from the stem cell niche into non stem cell compartments by comparing the telomere distribution before and after the application of a signal known to cause mobilization of stem cells from the stem cell niches. In particular, example 2 of the experimental part shows that animals treated with the phorbol ester TPA undergo a rearrangement of the stem cell compartment which manifests itself in a decrease in the average fluorescence and telomere lengths of the cells found in the stem cell niche. Thus, by providing a tissue with a known distribution of stem cells, it is possible to identify compounds which promote stem cell mobilization. Thus, in another aspect, the invention relates to a method (hereinafter "the first screening method of the invention") for the identification of compounds capable of triggering mobilisation of stem cells within a tissue having a known spatial distribution of stem cells comprising the steps of
- (i) contacting said tissue sample with a candidate compound under conditions adequate for promoting mobilisation of the stem cells within said tissue,
- (ii) contacting a sample of said tissue with a probe that hybridises specifically to a repeat region within telomeric DNA and which is labelled with a first fluorescent dye under conditions allowing the probe to hybridise in situ to its complementary target sequences on telomeres and
- (iii) determining the average fluorescence intensity of a representative sample of cells present in the region of the tissue sample known to contain the stem cells wherein a decrease in the average fluorescence intensity in the area which is known to comprise stem cells when compared to a sample which has not been treated with the candidate compound is indicative that the compound is capable of triggering mobilisation of stem cells within the tissue sample.

In yet another aspect, the invention relates to a method (hereinafter "the second screening method of the invention") for the identification of compounds capable of triggering mobilisation of stem cells within a tissue having a known spatial distribution of stem cells comprising the steps of
- (i) contacting said tissue with a candidate compound under conditions adequate for promoting mobilisation of the stem cells within said tissue,
- (ii) contacting said tissue and at least two homogeneous control cell populations of known and stable telomere length and having different average telomere lengths with a probe that hybridises specifically to a repeat region within telomeric DNA and which is labelled with a first fluorescent dye under conditions allowing the probe to hybridise in situ to its complementary target sequences on telomeres,
- (iii) determining the average fluorescence intensities of a representative sample of cells present in the region of the tissue sample known to contain the stem cells and an average fluorescence intensity value of the cells within each control cell population in response to a radiation adequate to excite the fluorescent dye attached to said probe and
- (iv) assigning to each cell within the representative sample of cells present the region of the tissue sample known to contain the stem cells an average telomere length value, wherein said value is the average telomere length of a cell within a control cell population showing an average cellular fluorescence intensity value identical to the fluorescence intensity values of the cell within the cell population as determined by interpolation wherein a decrease in the average telomere length of the cells within the region of the tissue known to comprise stem cells when compared to a sample which has not been treated with the candidate compound is indicative that the compound is capable of triggering mobilisation of stem cells within the cell population.

The method requires the knowledge in advance of tissues wherein the stem cell niche is known. In principle, any tissue which is known to contain a population of stem cells and whose spatial distribution is known may be used in the screening methods of the invention. By way of example, tissues that may be used in the present invention include skin, intestine, cornea, testis and central nervous system.

In the murine skin, a stem cell population is located in the hair follicle. The epidermis comprises four compartments, namely, the hair bulge, wherein the stem cells are located, the bulb, the infumdibulum, wherein the transit amplifying cells are found and the interfolicular epidermis.

In small intestine, the stem cells reside in the Lieberkuhn crypts, just above the Paneth cells and below the transit amplifying cells. The more differentiated cells are found in the epithelium forming the intestinal villi (see Gregorieff et al., 2005, Gastroenterology, 129:626-638 and Marshman et al., 2002, Bioessays 24, 91-98).

In the cornea, the stem cells are located in the limb, corresponding to the peripheral cornea, just above the ciliated body (see Lavker and Kligman, 1988, J. Invest. Dermatol., 90:325-330 and Lehrer et al., 1998, J. Cell Science, 111:2867-2875).

In testis, the stem cells are located in the peripheral region of the seminiferous tubes (Guan et al., 2006, Nature 440, 1199-1203).

In the central nervous system, stem cells can be found in the subgranular zone of the hippocampus, localised between the granular cell layer and the hilio (see Alvarez-Buylla and Lim, 2004, Neuron 41, 683-686 and Sage et al., 2000, Genes & Development 14: 3037-3050).

Once an adequate tissue has been selected for carrying out the method of the invention, the method involves in step (i) contacting a tissue with a compound whose activity as promoter of stem cell mobilization wants to be studied. It will be understood that the contacting step can be carried out in several different ways. In one embodiment, the contacting step is carried out in the living animal prior to isolating the tissue sample by administering to said animal the compound to be tested prior to removal of the tissue for telomapping studies. Any suitable means of administration of a compound to an animal is possible within the present invention as long as the compound is able to reach the stem cell niche of the target tissue. By way of example, the compound may be administered orally, intradermically, parenterally and the like. In another embodiment, the contacting step may be carried out on the isolated tissue maintained under perfusion by providing the compound to be tested to the perfusion media. In another embodiment, the tissue under study is isolated from the vasculature of the organism where it is found by using a catheter system as described e.g. in U.S. Pat. No. 6,699,231 and the compound under study is then provided directly to the vasculature of the isolated tissue.

Moreover, the invention contemplates no limitation as to the type of compound that can be tested. In case the candidate compound is a molecule with low molecular weight, it is enough to add said molecule to the culture medium. In the event that the candidate compound is a molecule with a high molecular weight (for example, biological polymers such as a nucleic acid or a protein), it is necessary to provide the means so that this molecule can access the interior of the cells forming the tissue. In the event that the candidate molecule is a nucleic acid, conventional transfection means such DNA precipitation with calcium phosphate, DEAE-dextran, polybrene, electroporation, microinjection, liposome-mediated fusion, lipofection, infection by retrovirus and biolistic transfection can be used. In the event that the candidate compound is a protein, the cells can be put in contact with the protein directly or with the nucleic acid encoding it coupled to elements allowing its transcription/translation once they are in the cell interior. To that end, any of the aforementioned methods can be used to allow its entrance in the cell interior. Alternatively, it is possible to put the cell in contact with a variant of the protein to be studied which has been modified with a peptide which can promote the translocation of the protein to the cell interior, such as the Tat peptide derived from the HIV-1 TAT protein, the third helix of the Antennapedia homeodomain protein from *D. melanogaster*, the VP22 protein of the herpes simplex virus and arginine oligomers (Lindgren, A. et al., 2000, *Trends Pharmacol. Sci,* 21:99-103, Schwarze, S. R. et al., 2000, *Trends Pharmacol. Sci.,* 21:45-48, Lundberg, M et al., 2003, *Mol. Therapy* 8:143-150 and Snyder, E. L. and Dowdy, S. F., 2004, *Pharm. Res.* 21:389-393).

Steps (ii) and (iii) of the first screening method of the invention is carried out basically as described above with respect to the second method of the invention.

Steps (ii), (iii) and (iv) of the second screening method of the invention is carried out basically as described above with respect to the third method of the invention.

In the first screening method of the invention, the fluorescence values of each cell within the representative sample obtained in step (iii) are then compared with a similar sample which has not been treated with the compound to be tested. Different approaches can be used for said purpose. In a preferred embodiment, the fluorescence values of the cells within the cell population are divided in four intervals and each cell is assigned to each interval depending on its fluorescence values so that the percentage of cells within each region of the tissue within each fluorescence interval can be determined. If the tested compound has promoted the mobilization of the stem cells from the stem cell niche, a reduction in the percentage of cells within the upper quartile within the area of the tissue known to contain the stem cells and/or an increase in the number of cells within the lower quartile in the areas of the tissue containing the transit amplifying cells or the differentiated cells in comparison with a sample which has not been treated with said compound will be observed.

In the second screening method of the invention, the telomere length values of each cell obtained in step (iv) are then compared with the telomere lengths of the cells of a similar sample which has not been treated with the compound to be tested. Different approaches can be used for said purpose. In a preferred embodiment, the telomere lengths values of the cells within the cell population are divided in four intervals and each cell is assigned to each interval depending on its telomere length so that the percentage of cells within each region of the tissue within each telomere length interval can be determined. If the tested compound has promoted the mobilization of the stem cells from the stem cell niche, this will be observed as a reduction in the percentage of cells within the upper quartile within the area of the tissue known to contain the stem cells and/or an increase in the number of cells within the lower quartile in the areas of the tissue containing the transit amplifying cells or the differentiated cells in comparison with a sample which has not been treated with said compound.

As described above, image collection of the tissue samples can be carried out using a confocal microscope. In this case, several confocal images are collected spanning the whole tissue sample depth and a final image is obtained by merging the different confocal images using the maximum projection. Moreover, in a preferred embodiment, the determination of the fluorescence values is carried out on those regions of the image corresponding to the cell nuclei. For said purpose, the sections are simultaneously stained with a DNA dye, which allows the localization of the cell nuclei. The pattern of cell nuclei is then used to construct a mask that is used to select those regions of the image wherein the telomere-associated fluorescence is captured.

Tissue Arrays

The authors of the present invention have also observed that the sensitivity in the determination of the telomere length of a cell within a test cell population can be improved by processing in parallel a plurality of samples, each containing a cell population of known and stable telomere length. The co-processing of the tissue under study and of the control cell population is most adequately carried out by using a tissue microarray comprising all the different control cell populations. This microarray can then sectioned by conventional means and processed in parallel to the tissue sample. Thus, in another aspect, the invention relates to an array comprising at least two immobilised tridimensional cell populations being each cell population physically separated from the other(s) and wherein each cell population has a stable and known telomere length which is different to the average telomere length of the other cell population(s) of the array.

The tissue arrays according to the invention contain a plurality of different cell population samples in a single receiver block. The block material can be any material that is known in the art and that allows for the preparation of tissue sample blocks that will function in the methods and compositions of the invention. Those materials include agarose, gelatin, paraffin and others that will be understood by those of skill upon reading this specification. In a preferred embodiment, the block is made of gelatine, more preferably 5% gelatine. The receiver block is sectioned in the usual manner with a microtome, and the section is applied onto a specimen slide. The specimen slide then contains a plurality of different tissue samples. Because of the large number of tissue samples on a single specimen slide, it is possible to stain or process all the samples under the same conditions. Multiple tissue samples may be taken from multiple such tissue specimens, and the multiple samples from a particular specimen are similarly placed at corresponding positions in the multiple recipient substrates. Each of the resulting substrates contains an array of tissue samples from multiple specimens, in which corresponding positions in each of the arrays represent tissue samples from the same tissue specimen. In particular examples, each substrate is then sectioned into multiple similar sections with samples from the same tissue specimen at corresponding positions of the sequential sections. The different sections may then be subjected to different reactions, such as exposure to different histological stains or molecular markers, so that the multiple "copies" of the tissue microarrays can be compared for the presence of reactants of interest. The large number of tissue samples, which are repeated in each of a potentially large number of sections of multiple substrates, can be exposed to as many different reactions as there are sections. For example, about 100.000 array sections may be obtained from a set of 1000 tissue specimens measuring 15×15×3 mm. This approach provides a high-throughput technique for rapid parallel analysis of many different tissue specimens. In a particular embodiment of the method, the specimens are embedded in embedding medium to form tissue donor blocks, which are stored at identifiable locations in a donor array. The donor blocks are retrieved from the donor array, coordinates of particular areas in each of the tissue specimens in the donor blocks are determined, and tissue samples from the donor blocks (such as elongated punches) are retrieved and inserted into receptacles of corresponding size (such as punched holes) in different recipient tissue microarray blocks. After repeating this process with multiple donor blocks, to form a three-dimensional array of substantially parallel elongated samples from a variety of different specimens, the recipient tissue microarray blocks are then sectioned to make multiple similar tissue microarray sections that include samples of many different specimens. Each of these sections can then be subjected to treatment with multiple reagents, and subsequently analyzed for the presence of biological markers.

Preferably, the different samples of the array are formed by cells derived from stable cell lines. In a more preferred embodiment, the cell lines of the tissue microarray are selected from the group of Hela 2, HeLa, MCF7, HeLa S3, 293T, L5178Y-S, MEFs BL6 G3 Terc$^{-/-}$, MEFs BL6 wild type, HeLa 1211, MEFs 129Sv/BL6 wild-type and L5178Y-R.

Methods for Determining Telomere Length using Image Processing

In yet another aspect, the inventors have developed a method which allows the determination of the telomere length in individual cells within images of three-dimensional cell populations labelled with a telomere-specific fluorescent probe. Thus, in another aspect, the invention relates to a method for determining the telomere length of a cell within a tridimensional cell population from a collection of at least two fluorescence microscopy images obtained using a fluorescently-labeled telomere-specific probe and corresponding to different focal planes of said cell population comprising the steps of:

(i) converting the at least two fluorescence microscopy images corresponding to different focal planes into a single image by adding up the fluorescence intensities at each position within the image, (ii) determining the average fluorescence intensity of said cell within the image of the cell population obtained in step (ii) and (iii) assigning to said cell an average telomere length value, wherein said value is obtained by interpolation of the average intensity of the cell within a data set of telomere length values and corresponding fluorescence intensity values obtained from different cell populations of known and stable telomere length processed by fluorescence microscopy in parallel to the cell of the test cell population.

Step (i) comprises the merging or flattering of the different confocal images of the cell population so as to obtain a single image wherein each pixel contains the addition of the intensities of the corresponding pixels at the same positions from each confocal image. The image is usually obtained by fluoresence microscopy analysis of said cell population. For this purpose, a cell population has been previously contacted with a fluorescently-labelled telomere-specific probe. Using appropriate optical filters to allow excitation of the cells with the appropriate wave-length and capturing only the emission wave-length, it is possible to capture an image wherein the optical density of the stained cells will be proportional to the amount of the probe bound to the telomeric regions and, indirectly, to the length of the telomere in the cell. When using a confocal microscope, the microscope can be programmed so as to obtain the different focal images at given focal lengths (preferably 1 μm).

The microscope is attached to an adequate image capture device having digitalisation means so that a digital image is obtained. A digital image, as used herein, is a two-dimensional array of pixels. Each pixel value relates to the amount of light received by the imaging capture device corresponding to the physical region of pixel. Preferably, image collection is carried out using a microscope, preferably a confocal microscope, attached to appropriate detectors (for instance, a CCD camera). For colour imaging applications, a digital image will often consist of red, green, and blue digital image channels. Those skilled in the art will recognize that the present invention can be applied to, but is not limited to, a digital image channel for any of the herein-mentioned applications. Although a digital image channel is described as a two dimensional array of pixel values arranged by rows and columns, those skilled in the art will recognize that the present invention can be applied to non-rectilinear arrays with equal effect. The image file format can be any format used for digital images, including for example, a JPG format, a JPG2 format, a RAW format, a TIFF format, a PNG format, a GIF format, or a BMP format. Depending on the size and the resolution of the image, the digital image can be stored in storage media readable in a computer, such as, a CD, a DVD, a web-hard disk, a memory card, etc., and then provided to users.

Step (ii) of the method of the invention comprises the determination of the intensity of the telomere-specific fluorescent emission within a given target cell of the cell population in the flattened image obtained in step (i). This step comprises determining, in first instance, the region of interest (ROI) within the wherein fluorescent emission is to be determined. The ROI may be a region corresponding to the whole cell under study which can be determined, by way of example, by overlying a bright filed image of the same cell population. Preferably, the ROI may be the region corresponding to the nucleus of the cell under study, which is identified by overlying a fluorescent image captured of the same cell population labelled with a DNA-specific fluorescent probe with the image under study. Once the ROI is identified, the determination of the intensity level of each pixel within the ROI is usually carried out using a personal computer, a workstation, a network computer or a personal digital assistant which can determine the intensity level of each pixel in the cell under study. The intensity of the telomere-associated fluorescence can be measured as "average grey value" and is usually calculated by dividing the summation of the intensities of all pixels of the ROI under study by the number of pixels. These values are thus the average fluorescence intensity over the whole ROI and not the average of the intensities in those pixels corresponding to the individual telomeres.

It will be appreciated that background noise may interfere with the determination of the of pixel intensity. In order to avoid this problem, digital thresholding is usually applied to distinguish desired intracellular fluorescence from unwanted background fluorescence. Because background fluorescence (including cell autofluorescence as well as non-specific fluorescence due to non-specific binding of the telomere-specific probe to non-telomeric structures) is more diffuse and is less intense than telomere-specific fluorescence, contribution to the total fluorescence measurement from background fluorescence is reduced by ignoring light intensities which are below a specified value. In a preferred embodiment, the correction of probe accessibility and cell ploidy is carried out by normalising the fluorescence values of the cell within the image obtained in step (i) using the fluorescence values of the same cell within a corresponding image obtained using a fluorescently-labeled centromeric.

The skilled person will appreciate that other corrections algorithms may be applied to the image to remove any artifacts introduced by the image capture system. For example, "quality control algorithms" may be employed to discard image data based on, for example, poor exposure, focus failures, foreign objects, and other imaging failures. Generally, problem images can be identified by abnormal intensities and/or spatial statistics.

Step (iii) of the method of the invention is carried out once the average gray values for each cell are determined. Step (iii) comprises assigning to said cell an average telomere length value, wherein said value is obtained by interpolation of the average intensity of the cell within a data set of telomere length values and corresponding fluorescence intensity values obtained from different cell populations processed by fluorescence microscopy in parallel to the cell of the test cell population.

The skilled person will appreciate that the data set used for determining the telomere length values of selected cells within the test image can be obtained from images of reference cell lines wherein said images have been captured immediately before obtaining the images of the test cell population, in which case, the average fluorescence intensities and the telomere lengths in each cell type are stored as a dynamic data base until the fluorescence values of the cell or cells under study are available for interpolation. In a preferred embodiment, the images of the test cell population and the images of the different control cell populations are collected sequentially in an automated fashion by using a microscopy with a motorised stage.

In a preferred embodiment, the determination of the image density of the cells under study is carried out not on the whole cell surface but on those areas of the image which correspond to the cell nuclei. In order to identify the cell nuclei, the same cell population which is under study is also stained with a fluorescent DNA dye and an image is captured using adequate filters to detect fluorescence emission by said DNA dye. The resulting image comprises spatial information of the location the cell nuclei within the cell image and is then used as mask to select those areas of the image derived from the telomere-specific fluorescence which correspond to cell nuclei. Thus, in a preferred embodiment, the method of the invention comprises, previous to step (i), the selection of those regions of the cells within the cell image corresponding to cell nuclei using a mask obtained by fluorescence microscopy analysis of the cell population using a DNA-specific fluorescent dye and the determination of the average fluorescence intensity in step (i) is carried out on the regions of the image which have not been masked.

In yet another embodiment, the invention relates to a computer program including encoded means to carry out the steps of the methods according to the invention. The computer program is provided on a computer-readable media. Thus, in another aspect, the invention relates to a computer-readable support comprising encoded means adapted to carry out the steps of the methods of the invention. Any method or technology suitable for storing information can be used for storing the program of the invention. By way of example, the invention comprises any readable medium such as RAM, ROM, EEPORM, flash memories or other types of memory, CD-ROM, DVD or other types of optic storage media as well as magnetic tapes, hard drives and other types of devices for magnetic storage. Alternatively, the program may be hosted in a remote storage device. In this case, the instructions encoded in the program are delivered by a telematic communication system such as wireless network, internet, local area networks, wide band networks, direct connections via a USB serial port or via model, (ISDN) or digital subscriber lines (DSL); satellite links as well as any other communication types known to the skilled person.

Having now generally described this invention, the same will be better understood by reference to certain specific examples which are included herein for purposes of illustration only and are not intended to be limiting of the invention or any embodiment thereof, unless so specified.

EXAMPLES

Example 1

Experimental Procedures

Mice, Treatment Regimens, and Mouse Sample Collection

Unless otherwise specified, all mice used in this study were males of approximately 2 months of age and from a C57BL6 genetic background. Mice of a FVB genetic background (2 months-old) were also used in Supplementary FIG. S1. Generation and characteristics of the Terc−/− and the K15-EGFP mice were previously described (Morris et al., 2004; Blasco et al., 1997).

To induce epidermal stem cell "mobilization" (activation, migration and proliferation), tail skin in the telogen (resting) phase of the hair cycle was topically treated every 48 h with TPA (20 nmol in acetone) for a total of four doses. Control mice of each genotype were treated with acetone alone. 24-hours after the last TPA treatment, mice were sacrificed and the tail skin analysed.

For telomere length analyses, samples from mouse tail and back skin, small intestine, cornea, testis and brain were harvested and fixed o/n in neutralbuffered formalin at 4° C., dehydrated through graded alcohols and xylene, and embedded in paraffin. Prior to embedding, dissected skin was cut parallel to the spine in order to obtain longitudinal hair follicle sections. The intestinal tract was flushed with PBS and rolled up in a compact circle using longitudinally oriented jejunal sections for analysis. For cornea and testis analyses, whole eyes and testis were cut in half prior to dehydration. Finally, brain was coronal-dissected to harvest the rostral hippocampus. In all cases, 5" M sections were used for QFISH and immunostaining analyses.

Telomerase Assay

Telomerase activity was measured with a modified telomere repeat amplification protocol (TRAP) as described (Blasco et al., 1997). An internal control for PCR efficiency was included (TRAPeze kit Oncor, Gaithersburg, Md.). Hela cells were included as a positive control for telomerase activity.

Confocal Quantitative Telomere Fluorescence In Situ Hybridization (Confocal Q-FISH) on Histological Sections For Q-FISH, paraffin-embedded tissue sections were hybridized with a PNA-tel Cy3-labelled probe and telomere length was determined as described (González-Suárez et al., 2000; Muñoz et al., 2005; Zijlmans et al., 1997). Slides were deparaffinized in three xylene washes (3 m each), then treated for 3 m with a 100, 95 and 70% ethanol series, followed by telomere Q-FISH protocol performed as described (Samper et al., 2000). DAPI, Cy3 signals were acquired simultaneously into separate channels using a confocal ultraspectral microscope (Leica TCS-SP2-A-OBS-UV) using a PL APO 20×/0.70 PH2 as lens with Leica LCS software and maximum projections from image stacks (10 sections at steps 1.0 µm) were generated for image quantification. The DPSS-561 laser (Cy3 laser) was hold at a constant intensity to capture all the mouse tissues images.

Generation of Topographic Telomere Length Maps on Histological Sections or "Telomapping"

High throughput quantitative image analysis was performed on confocal images using the Metamorph platform (version 6.3r6; Molecular Devices, Union City, Calif.). The DAPI image was used to define the nuclear area and the Cy3 image to quantify of telomere fluorescence. In all cases, background noise was subtracted from each image prior to making qualitative measurements. The DAPI images were signal-intensity thresholded, segmented and converted to 1-bit binary image. The binary DAPI mask was applied to the matching Cy3 to obtain a combined image with telomere fluorescence information for each nucleus. Cy3 fluorescence intensity (telomere fluorescence) was measured as "average gray values" (total gray value/nuclei area) units (arbitrary units of fluorescence). These "average telomere fluorescence" values always represent the average Cy3 pixel intensity for the total nuclear area, and not the average value of individual telomere spot intensities, therefore ruling out that differences in nuclear size may influence telomere length measurements. A code of four colours was used to classify the nuclei according to their average telomere fluorescence. Telomere fluorescence ranges were initially set up to allocate in each range roughly ¼ of the total cells of a given tissue in wild type mice of 2 months of age. Subsequently, telomere fluorescence ranges were fine adjusted to better delineate the location of stem cell compartments in different tissues. Telomere fluorescence ranges of a given tissue obtained in this manner were then maintained constant between genotypes, treatment and ages to facilitate comparisons. Finally, telomere fluorescence values for each histological region (i.e. skin sections were subdivided in hair follicle bulge, hair follicle bulb, hair follicle infundibulum, and interfollicular epidermis) were exported to Excel and the frequency histograms were generated. A macro created using the Metamorph platform allowed the automated and user-controlled processing of the DAPI and Cy3 images to obtain the telomap images (available upon request).

To avoid differences due to variation in section thickness, we used paraffin slices of the same thickness (5 µM) in all the tissues analyzed. Additionally, to avoid possible variations due to different roughness of the paraffin on the slices, confocal capture conditions were set to cover the entire fluorescence signal (maximum projections of 10 sections at steps of 1.0 µM). To avoid differences in day-to-day staining efficiency variation, Q-FISH and immuno-Q-FISH staining, as well as image capture were performed for each given tissue in the same day.

Finally, to control for differences in ploidy as well as probe accessibility, we used a Cy3-labelled PNA probe directed against mouse major satellite repeats (5'-TCG-CCA-TAT-TCC-AGG-TC-3') (SEQ ID NO: 1). As shown in Supplementary FIGS. S2ac, no significantly differences in centromeric fluorescence were detected between different skin and testis compartments, again ruling out that differences in "probe accessibility" or ploidy account for the observed differences in telomere length in the skin or the testis. Furthermore, we ruled out that differences in nuclear size between different compartments (ie, skin) could account for the observed differences in telomere length (Supplementary FIG. 2b). Similarly, as shown in FIGS. 2d,e, no significant differences in centromeric fluorescence were detected between GFP+ and GFP− sorted cells from the K15-EGFP mouse model, again ruling out that differences in "probe accessibility" or ploidy account for the observed differences in telomere length between between GFP+ and GFP− cells. To better assess differences in centromeric signal, maximum projections of 16-bits confocal images were obtained form paraffin sections. Finally, to verify whether image analyses by conventional Q-FISH and telomapping give similar results, the same confocal image of tail skin was quantified using the TFL-TELO program (gift from Dr. Lansdorp, Vancouver) and the Metamorph platform (version 6.3r6; Molecular Devices, Union City, Calif.) (see Supplementary FIG. S3).

Immunohistochemistry

Skin (5" M) sections were used for immunohistochemistry (IHC). Prior to IHC, slides were de-paraffinized, re-hydrated, immersed in 10 mM citrate solution and epitopes retrieved by three high-power, 5 min microwave pulses. Slides were washed in water, blocked in 1:10 dilution of normal goat serum (Vector Labs) and incubated with primary antibodies: CD34 at 1:200 (RAM34, BD Biosciences), and keratin 15 at 1:500 (LHK15, NeoMarkers). Slides were then incubated with secondary biotinylated antibodies from Vector labs (goat anti-rabbit at 1:200 or goat anti-mouse at 1:200), followed by signal development with an immunoperoxidase reagent (ABC-HRP, Vector Labs) and DAB (Sigma) as the substrate. Sections were lightly counterstained with hematoxylin and analyzed by light microscopy.

Cell Sorting and Telomere Length Measurements in K15-EGFP Mice

Eight week-old K15-EGFP mice were sacrificed and back skin and tail skin were harvested, fixed o/n in neutral-buffered formalin at 4° C., dehydrated through graded alcohols and xylene, and embedded in paraffin. Simultaneously, part of the tail skin was collected and soaked in Betadine for 5 m, in a PBS antibiotics solution for 5 m, in 70% ethanol for 5 m, and in PBS-antibiotics solution for 5 m. Tail skin was peeled off using forceps and floated on the surface of 1× trypsin (Sigma) solution (4 ml on 60 mm cell culture plate) for 3 h at 37° C. Tail skin was then transferred to a sterile surface and the epidermis separated from the dermis using forceps, and minced and stirred at RT for 30 m in serum-free Cnt-02 medium (CELLnTEC Advanced Cell Systems AG, Bern, Switzerland). The cell suspension was filtered through a sterile teflon mesh (Cell Strainer 0.7 m, Falcon) to remove cornified sheets. Keratinocytes were then collected by centrifugation (160 g) and counted. Freshly isolated keratinocyte suspensions from K15-EGFP mice were then sorted with a fluorescence-activated cell sorter (FACS) using a MoFlo (DakoCytomation, Glostrup, Denmark). Cells were excited with a 488-nm laser and GFP signals collected via the FL1 channel (510 to 550 nm), sorting them in an "enrichment" mode into GFP-positive and GFP-negative cells. The sorted cell suspensions were centrifuged onto microscope slides using a cytospin (Cytospin 3; Thermo Shandon, Pittsburgh, Pa.). After air-drying, cells on slides were fixed in methanol/acetic acid (3:1) during 1 h and dried o/n. Telomere FISH was performed as described calculating the telomere fluorescence of the whole nuclei (Muñoz et al., 2005; Samper et al., 2000). For telomere length quantification on interphase nuclei, Cy3 and DAPI images were captured at 100× magnification using a COHU CCD camera on a Leica Leitz DMRA (Leica, Heidelberg, Germany) microscope, and the telomere fluorescence was integrated and quantified using spot IOD analysis in the TFL-TELO program (Zijlmans et al., 1997) (gift from Dr P. Lansdorp, Vancouver). The telomere fluorescence of individual nuclei was represented by frequency histograms. In parallel, combined GFP-immunostaning/telomere-QFISH was performed in paraffin-embedded sections of back and tail skin from K15-EGFP mice to quantify telomere length in GFP positive and negative cells. Slides were deparaffinized, re-hydrated, immersed in 10 mM citrate solution and epitope retrieved by three high-power, 5 m microwave pulses. Slides were then rinsed in water, permeabilized in 0.25% Triton X-100/PBS, blocked in BSA 10%/PBS for 30' at RT and incubated with BD Living Colours AV Monoclonal Antibody JL-8 (Becton Dickinson, San Jose, Calif.) at a 1:250 dilution for 30 m at RT. After three rinses with Tween20-PBS, slides were blocked in BSA 10%/PBS for 30 m at RT and incubated with goat antibody to mouse conjugated with Alexa 488 (1:500; Molecular Probes, Invitrogen) 30 m at RT. After three rinses with Tween20-PBS slides were fixed in methanol/acetic acid (3:1) for 1 h and dried o/n in the dark. Telomere Q-FISH was performed as described (Gonzalez-Suarez et al., 2000; Muñoz et al., 2005) with minor modifications to preserve GFP-immunostaining. DAPI, Cy3 and Alexa488 signals were acquired simultaneously into separate channels using a confocal ultraspectral microscope (Leica TCS-SP5-A-OBS-UV) using a PL APO 20×/0.70 PH2 as lens with Leica LAS AF software and maximum projection from image stacks (10 sections at steps 1.0 μm) were generated for image quantification.

Flow-FISH Telomere Length Measurements in K15-EGFP Mice

Freshly isolated keratinocyte suspensions (EGFP+ and EGFP−) from K15-EGFP mice were fixed in methanol/acetic acid (3:1), permeabilized with methanol 100% and washed in PBS. Cells were blocked in BSA 10% PBS for 15 m at RT and incubated with BD Living Colours AV Monoclonal Antibody JL-8 (Becton Dickinson, San Jose, Calif.) at 1:250 dilution for 30 min at RT. After two washes in Tween20-PBS cells were blocked in BSA 10% PBS for 15 m at RT and incubated with goat antibody to mouse conjugated with Alexa 647 at 1:500 dilution (Molecular Probes, Invitrogen) 30 m at RT. After two washes in Tween20-PBS cells were fixed in formaldehyde 0.5% PBS for 5 m and washed twice in PBS. Then telomere flow-FISH was performed as described (Rufer et al., 1998) using a FITC labeled PNA-tel probe and Propidium Iodide (PI, Sigma) to counterstain DNA, and analyzed in a FACScanto cytometer (BD Biosciences). Cells with adequate size and complexity as determined by forward scatter and side scatter channels, were gated for G0/G1 phase using the PI signal acquired in FL2 channel. Their labeling for Alexa 467 was acquired in FL4 channel and was used to identify GFP positive and negative cell populations. The telomere fluorescence as FITC signal was acquired in FL1 for both cell populations. To compensate for the contribution of cellular autofluorescence, fluorescence values of negative control cells (i.e. cells hybridized in the absence of the FITC PNA-tel probe) were subtracted from every sample. L5178Y-R and L5178Y-S cell lines with known telomere length of 10.2 and 79.7 kb (McIlracth et al., 2001), respectively, were processed in parallel and used to convert fluorescence values into kb. Negative controls for each fluorochrome and acquisition settings were established with unstained or single stained cell populations.

Telomapping of a Paraffin-Embedded Array of Human and Mouse Cell Lines

The cell line array was developed using a range of different cell lines with known telomere length (Canela et al., 2007). Cell lines were cultured and 4×106 cells from each one were used, washed in PBS, fixed in formaldehyde 4% PBS during 5 m at RT, washed twice in PBS and mixed with melted gelatine (Sigma) 5% PBS to generate gelatine blocks after polymerization at 4° C. overnight. Gelatine blocks were embedded in paraffin blocks as a classical fixed tissue, previously, every gelatin block was stained with blue metilene to allow its identification in the paraffin block. A small cylindrical cell-containing core of 1 mm diameter was performed in every paraffin block using a Manual Tissue Microarrayer MTA (Beecher, Sun Prairie, Wis., USA) and inserted in a receptor paraffin block separated from each other 1.5 mm. A 4" m section of one of these paraffin block containing every cell line was placed together with skin sections on the same slide and confocal Q-FISH was performed. Telomapping analysis were carried on images from skin follicles and interphase nuclei of every cell line, and telomere fluorescence values of the skin follicle compartments were converted in kb using these cell lines as calibration standard with stable and known telomere length (Canela et al., 2007).

TRF-Based Telomere Length Analysis of K15-EGFP Adult Keratinocytes

Isolated GFP+ and GFP− adult epidermal keratinocytes from K15-EGFP mice were sorted as indicated above. A fraction of enriched GFP-negative cells and GFP-positive cells were included in agarose plugs following instructions provided by the manufacturer (Bio-Rad), and TRF analysis was performed as previously described (Blasco et al., 1997).

Quantitative Telomere Length Analyses on K15-EGFP Skin Sections

Quantitative image analysis was performed on confocal images using Metamorph (version 6.3r6; Molecular Devices, Union City, Calif.). The DAPI image was used to define the nuclear area, the Cy3 image for telomere fluorescence determinations, and the Alexa488 image to identify the GFP-expressing cells. In all cases, background noise was subtracted from each image prior to qualitative measurements. The DAPI images were signal intensity thresholded, segmented and converted to 1-bit binary image. The binary DAPI mask was applied to both Cy3 and Alexa488 images obtaining topographic maps showing telomere fluorescence and GFP staining for each nucleus or object. Specific nuclear masks for GFP-positive and GFP-negative cells were generated to allow quantification of telomere fluorescence in the two populations. The nuclear mask of GFP-positive cells was created by converting the combined image from DAPI mask and Alexa488 to 1-bit image, showing only those nuclei that had an Alexa488-fluorescence above a minimum threshold. The nuclear mask for GFP-negative cells was created subtracting the GFP-positive mask from the DAPI mask. The three masks generated, DAPI, GFP-positive and GFP-negative, were applied to the Cy3 image obtaining the combined images with telomere fluorescence information for all nuclei, GFP-positive or negative nuclei, respectively. The combined images were then analyzed as indicated above.

Isolation of Newborn Keratinocytes

Two days old mice were sacrificed, soaked in Betadine (5 min), in a PBS antibiotics solution (5 min), in 70% ethanol (5 min), and in a PBS antibiotics solution (5 min). Limbs and tail were amputated, and the skin peeled off using forceps. Skins were then soaked in PBS (2 min), PBS antibiotics solution (2 min), 70% ethanol (1 min) and in PBS antibiotics solution (2 min). Using forceps, each skin was floated on the surface of 1×trypsin (Sigma) solution (4 ml on 60 mm cell culture plate) for 16 h at 4° C. Skins were transferred to a sterile surface, and the epidermis separated from the dermis using forceps, minced and stirred at 37° C. for 30 min in serum-free Cnt-02 medium (CELLnTEC Advanced Cell Systems AG, Bern, Switzerland). The cell suspension was filtered through a sterile teflon mesh (Cell Strainer 0.7 m, Falcon) to remove cornified sheets. Keratinocytes were then collected by centrifugation (160 g) for 10 min and counted.

Isolation of Adult Keratinocytes 2-months old and 27-31 months old mice were sacrificed and tail skin was collected and soaked in Betadine for 5 m, in a PBS antibiotics solution for 5 m, in 70% ethanol for 5 m, and in PBS-antibiotics solution for 5 m. Tail skin was peeled off using forceps and floated on the surface of 1×trypsin (Sigma) solution (4 ml on 60 mm cell culture plate) for 3 h at 37° C. Tail skin was then transferred to a sterile surface and the epidermis separated from the dermis using forceps, and minced and stirred at RT for 30 m in serum-free Cnt-02 medium (CELLnTEC Advanced Cell Systems AG, Bern, Switzerland). The cell suspension was filtered through a sterile teflon mesh (Cell Strainer 0.7 m, Falcon) to remove cornified sheets. Keratinocytes were then collected by centrifugation (160 g) and counted.

Clonogenic Assays 103 mouse keratinocytes obtained from 2-days-old mice and 104 mouse keratinocytes from 2-months-old and 27-31-months-old mice were seeded onto mitomycin C (10" g/ml, 2 hours) treated J2-3T3 fibroblast (105 per well, 6 well dishes) and grown at 37° C./5% $CO_2$ in Cnt-02 medium (CELLnTEC Advanced Cell Systems AG, Bern, Switzerland). After ten days of cultivation, dishes were rinsed twice with PBS, fixed in 10% formaldehyde and then stained with 1% Rhodamine B to visualizy colony formation. Colony size and number were measured using three dishes per experiment.

Statistical Analysis

A Wilcoxon's ram sum test was used to calculate the statistical significance of the observed differences in the different assays. Microsoft Excel v.2001 and Graphpad Instat v3.05 were used for the calculations. In all cases, differences are significant for $P<0.05$; very significant for $P<0.01$; and highly significant for $P<0.001$.

Example 2

Cells with the Longest Telomeres are Enriched at the Hair Follicle Stem Cell Compartment and Show Stem Cell Behaviour upon Treatment with Mitogenic Stimuli.

Figure 2A:
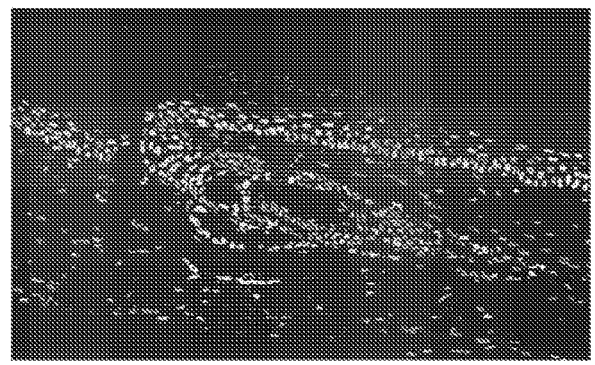
FIGS. 2A and 2B. Cells with the longest telomeres are enriched at the hair follicle stem cell compartment in mice from a FVB genetic background.
Figure 2A:
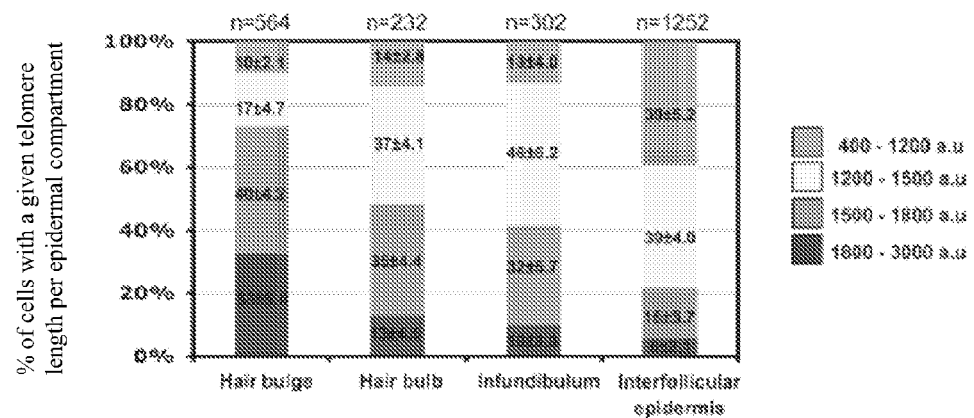
Figure 2B:
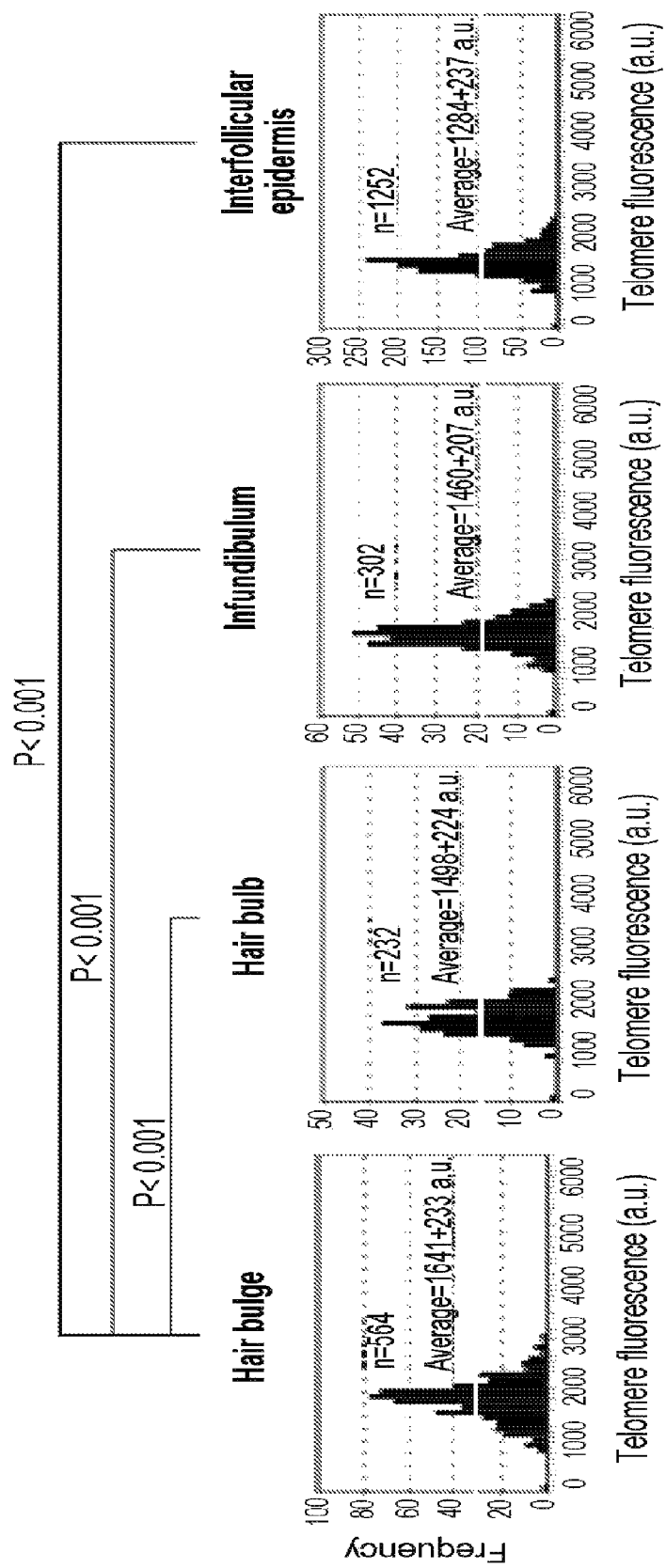
Figure 3A:
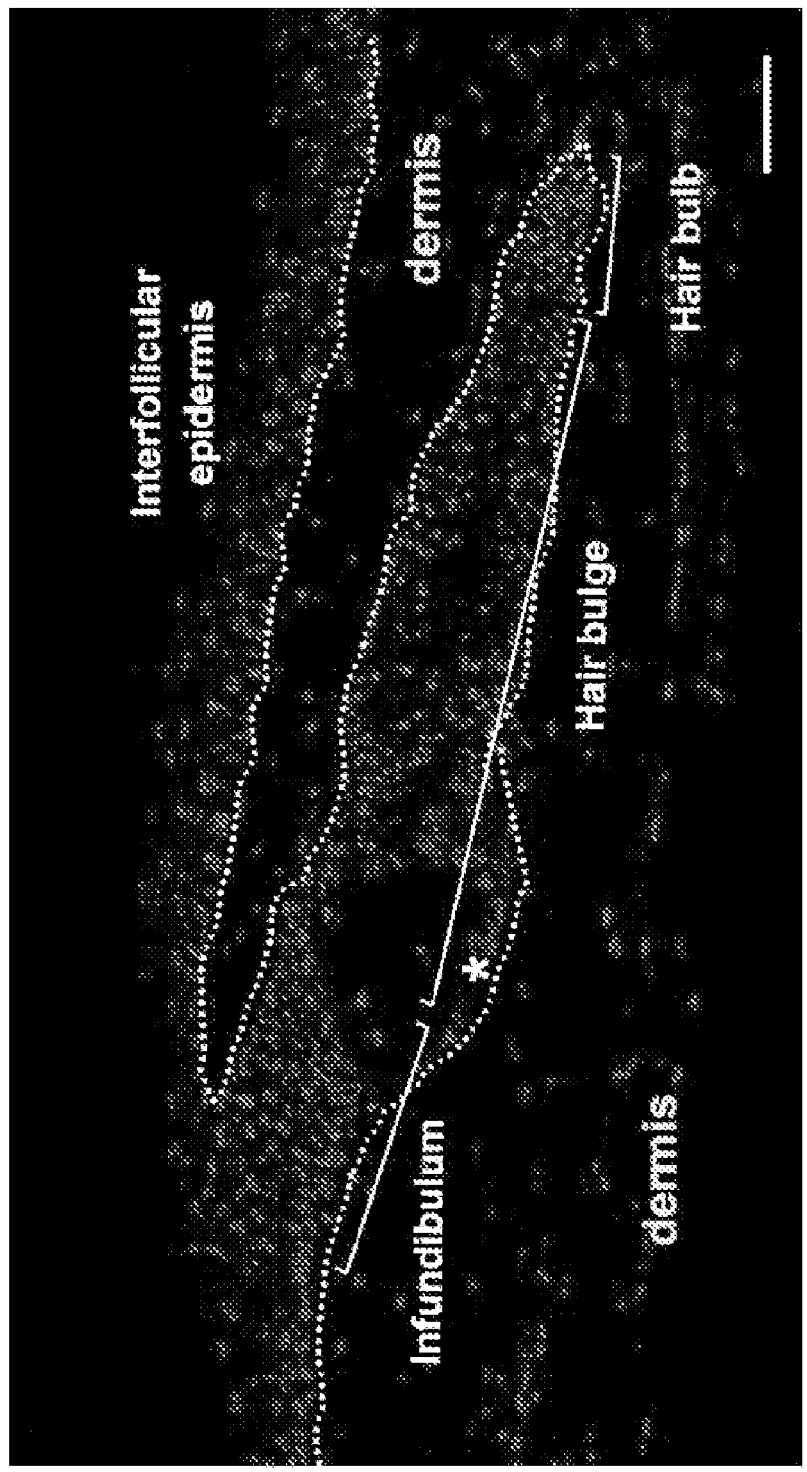
FIGS. 3A-3C. Controls for the telomapping technique.
Figure 3B:
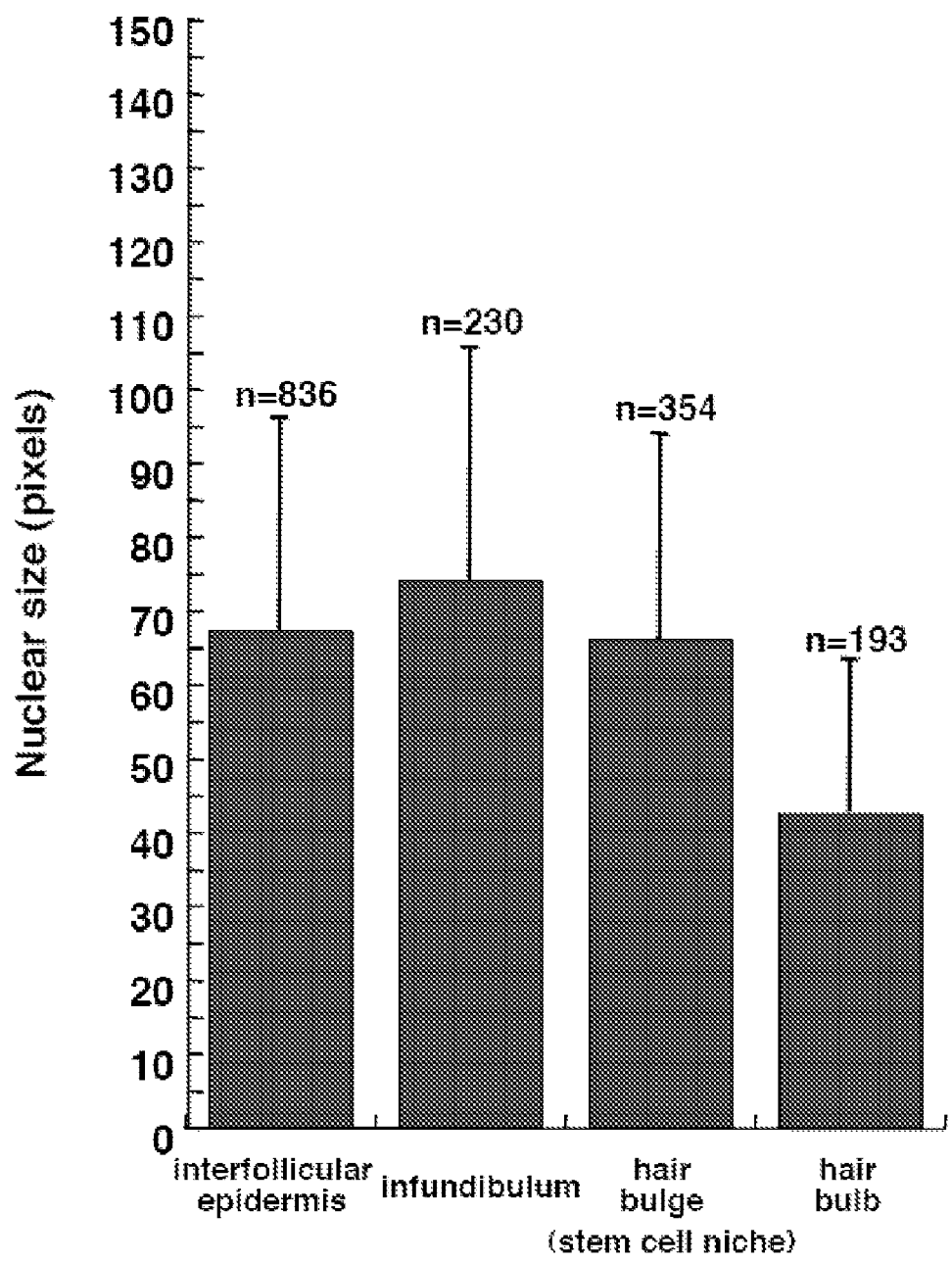
Figures 4A, 4B:
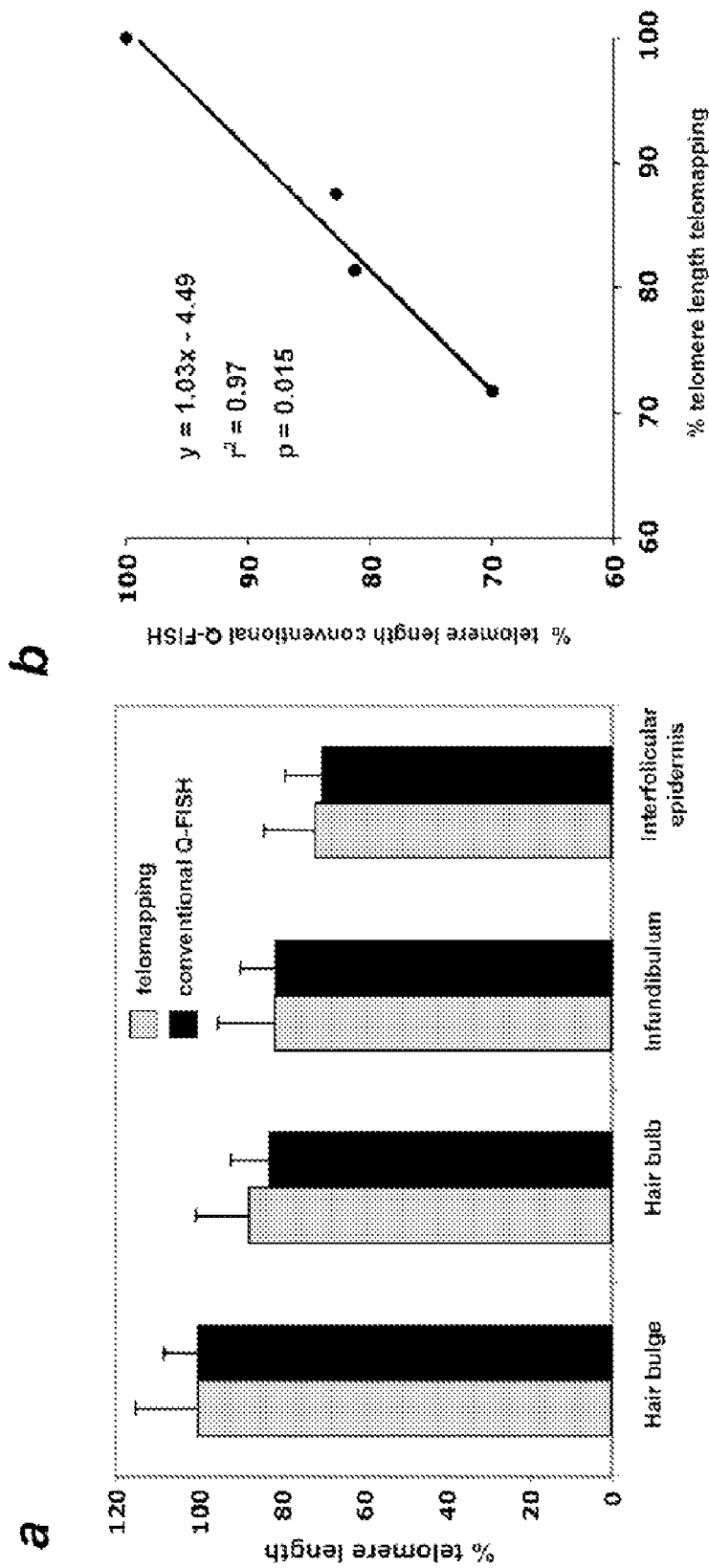
FIGS. 4A and 4B. Validation of telomapping results using conventional Q-FISH.
Figure 5A:
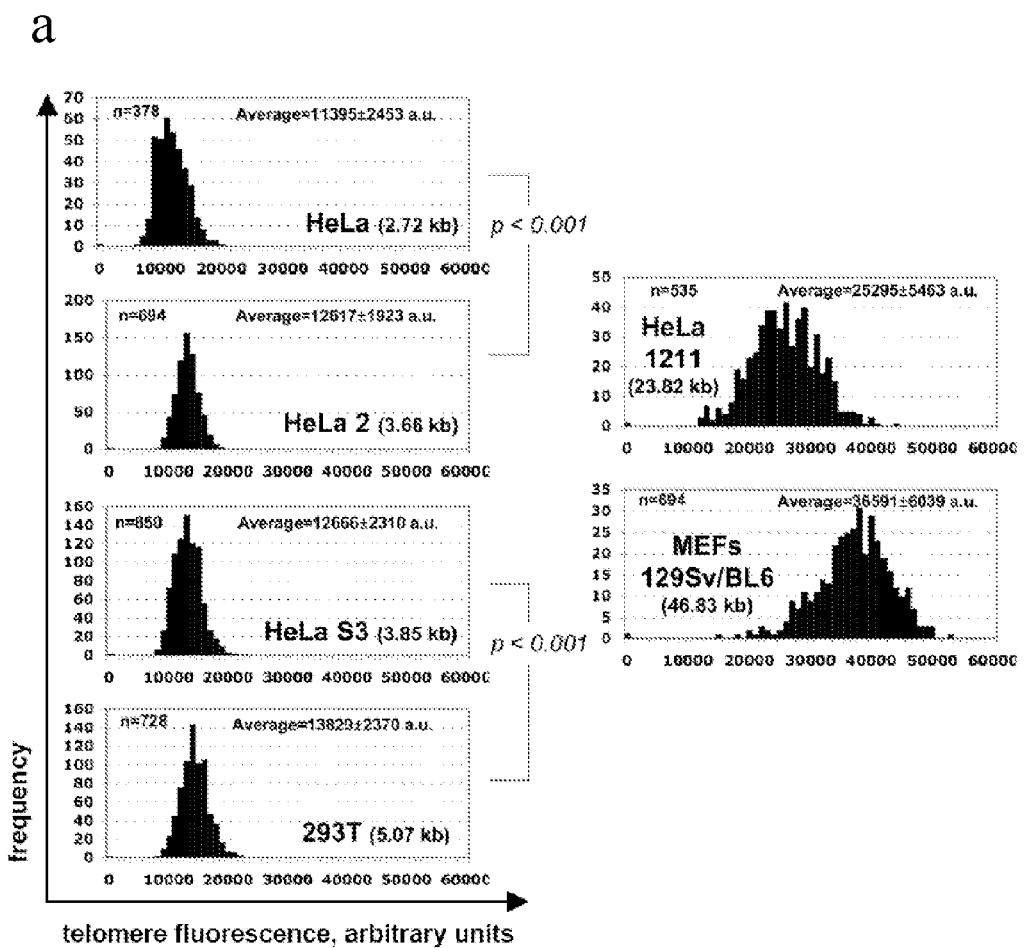
FIGS. 5A-5C. Calibration of telomapping technique using an array paraffin-embedded cell lines of known telomere length.
Figure 5B:
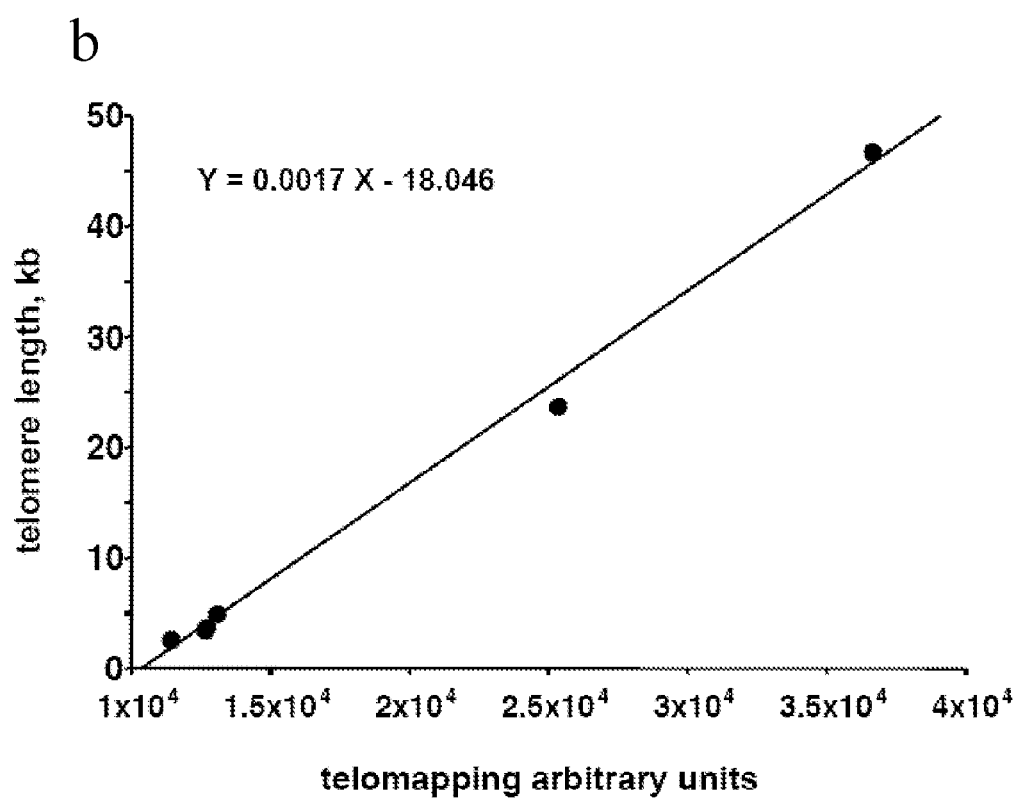
Figure 5C:
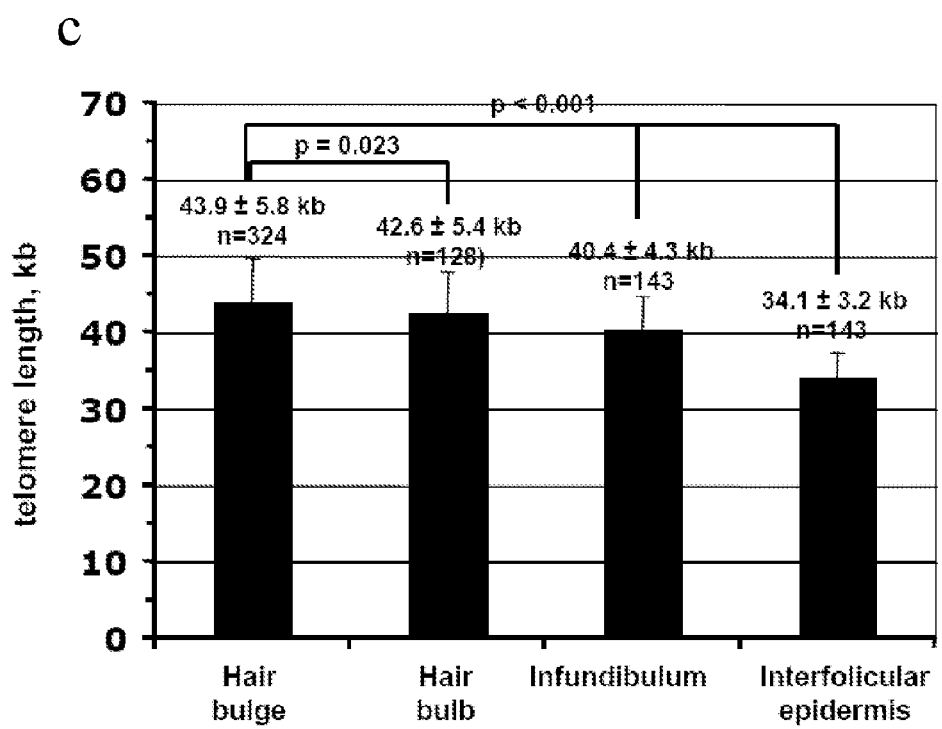

To evaluate whether telomere length could be used as a general marker to anatomically map stem cell compartments within adult tissues, confocal telomere fluorescence in situ hybridization (Confocal Q-FISH) was performed directly on tissue sections coupled to a single-cell highthroughput Metamorph image analysis platform (referred here as "telomapping") (see Experimental Procedures for detailed description of the technique and of different controls performed). First, single-cell topographic telomere length maps were generated for skin sections from 2 month-old wild-type mice of a C57BL6 genetic background (Experimental Procedures), which were subdivided in four different epidermal compartments: the hair follicle bulge where the hair follicle stem cell niche is located (Tumbar et al., 2004; Cotsarelis et al., 1990; Oshima et al., 2001; Morris et al., 2004), the hair follicle bulb and the infundibulum where the transit-amplifying (TA) cells reside, and the interfollicular epidermis (FIGS. 1a,b). In "resting" untreated wild-type mouse skin, it was observed that cells with the longest telomeres, 1800-3000 arbitrary units of telomere fluorescence (red color in FIG. 1a; see Experimental Procedures for criteria to establish telomere length ranges within a given tissue) were enriched at the hair bulge, coinciding with the known stem cell niche (Tumbar et al., 2004; Cotsarelis et al., 1990; Oshima et al., 2001; Morris et al., 2004). Immunostaining with the hair follicle stem cell markers CD34 and keratin 15 (K15) further confirmed that the longest telomeres localized to the hair bulge (not shown). These results were confirmed in age-matched mice of a different genetic background (FVB background; Experimental Procedures) (FIG. 2a,b). These findings indicate that telomeres are progressively shorter as cells move out from the stem cell compartment to the adjacent TA compartments (hair bulb and infundibulum), with the more differentiated layers of the interfollicular epidermis showing the shortest telomeres, in agreement with their longer proliferative and differentiation history. Of notice, these differences in telomere length are unlikely to be due to differences in "probe accessibility" or ploidy between different skin compartments as we did not find significant differences between compartments when performing Q-FISH with a centromeric major satellite probe (Experimental Procedures; FIG. 3a). Furthermore, telomere length differences are not likely to be due to differences in nuclei size between different skin compartments as telomere length is captured for the whole nucleus using the DAPI image (Experimental Procedures). Indeed, we did not find major differences in nuclear size between the stem cell compartment (hair bulge) and the interfollicular epidermis and infundibulum compartments that could account for the observed differences in telomere length (FIG. 3b). Next, the skin telomapping results were validated using the conventional quantitative telomere FISH technique (Q-FISH) on tissue sections (Experimental Procedures). Q-FISH on tissue sections has been extensively used to obtain quantitative and accurate telomere length determinations both in mouse (Gonzalez-Suarez et al., 2000; Muñoz et al., 2005) and human cells (Meker et al., 2002; 2004; Meeker and De Marzo, 2004). In particular, FIG. 4a shows a similar decrease in telomere length when comparing the hair bulge compartment to other skin compartments using telomapping or Q-FISH on tissue sections. Furthermore, there was a linear correlation in telomere length values obtained by these techniques (FIG. 4b). In order to calibrate the telomapping technique and to convert fluorescence values into kilobases, telomapping was performed on a paraffin-embedded array of human and mouse cell lines of previously known telomere lengths (Canela et al., 2007) (Experimental Procedures). As shown in FIG. 5a, telomapping was able to detect differences of telomere length of less than 1 Kb (see comparisons between HeLa and Hela2 cell lines, and between HeLaS3 and 293T cell lines; p<0.001 for both comparisons). Furthermore there was a linear correlation between telomapping results and Q-FISH telomere length results as determined by conventional Q-FISH on metaphases FIG. 5b). Finally, using this calibration, a decrease of telomere length was detected between the hair bulge (stem cell compartment) and the TA compartments of 1.3 Kb (hair bulb) and 3.5 Kb (infundibulum) and of 9.8 Kb when comparing the hair bulge to the interfollicular epidermis (FIG. 5c).

Figure 1B:
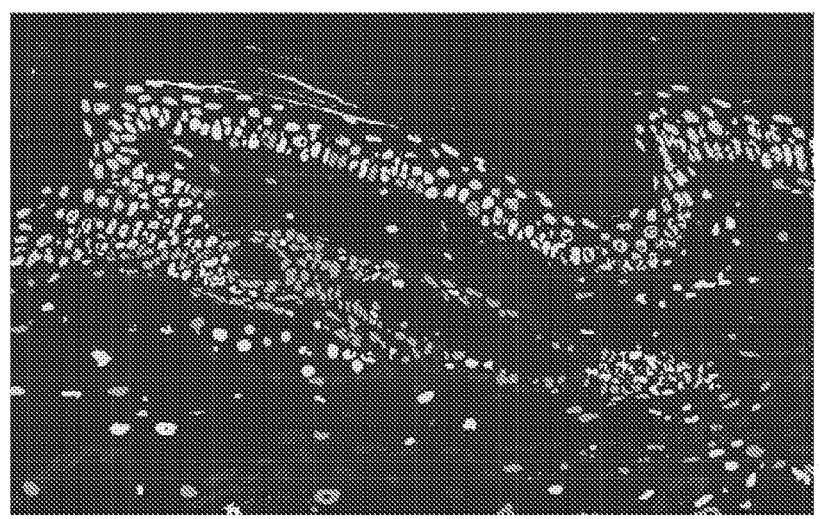
Figure 1B:
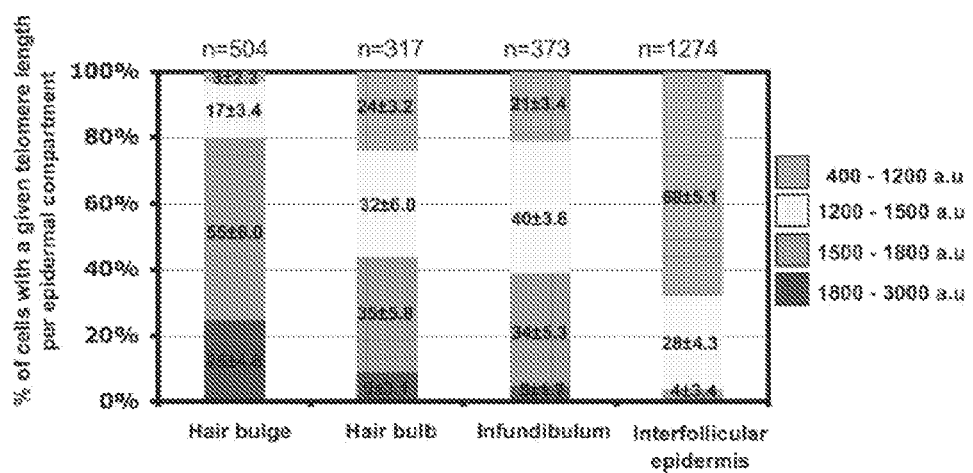
Figure 6:
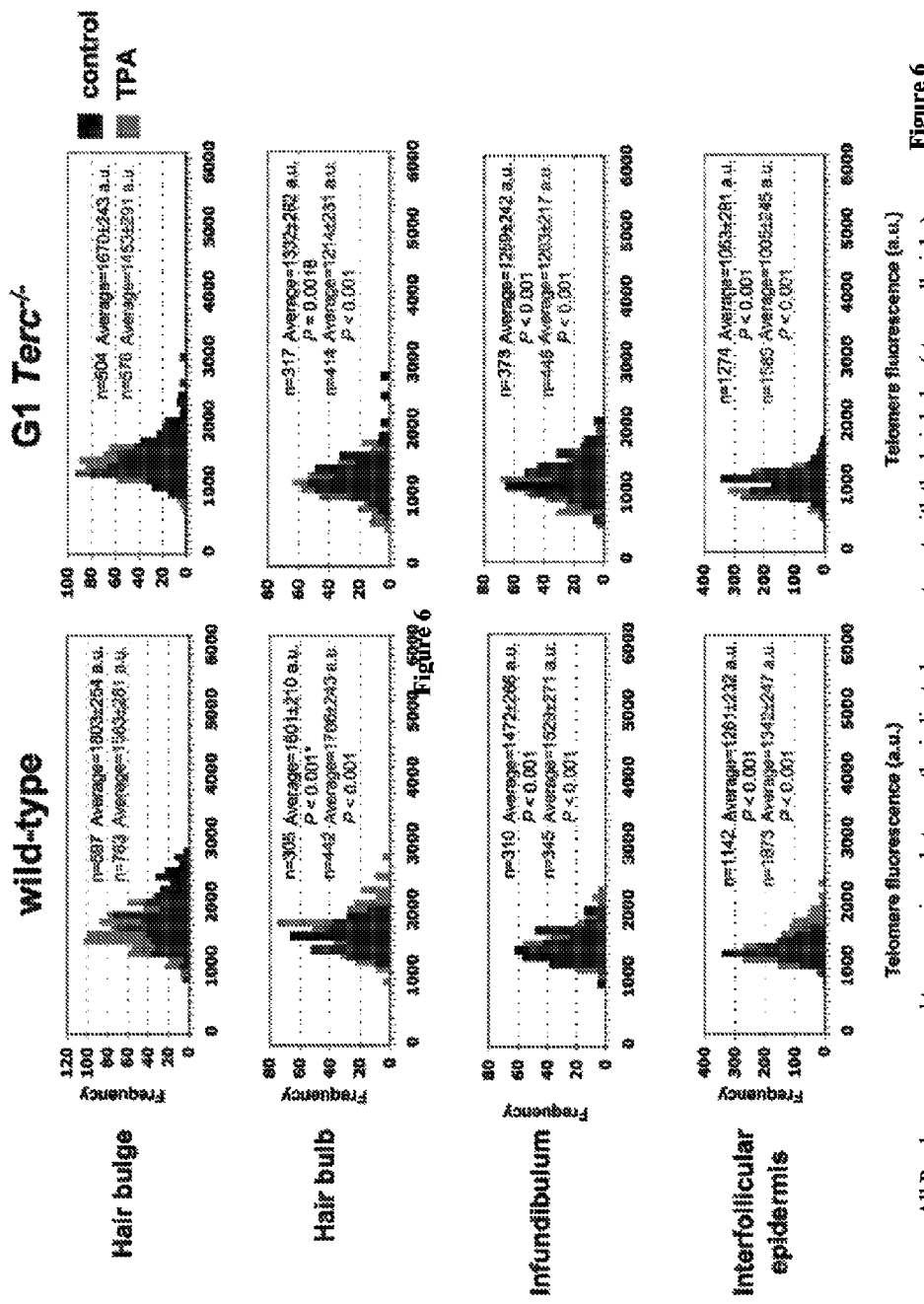
FIG. 6. Telomere distribution pattern of wild type and G1 Terc$^{-/-}$ epidermal cells before and after TPA treatment classified according to their location within the epidermis. Telomere fluorescence histograms for wild-type (left panels) and telomerase-deficient G1 Terc$^{-/-}$ mice (right panels) before (black columns) and after (red columns) TPA treatment. Epidermis has been subdivided in four different compartments: hair bulge, hair bulb, infundibulum and interfollicular epidermis. Total number of nuclei analyzed and average telomere length±SD are indicated for each compartment, genotype and condition. A total of 6 skin sections per genotype and condition were used for quantification purposes. Statistical significance comparisons between the hair bulge and the different compartments are indicated for both WT and G1 Terc$^{-/-}$ skin. In addition, all telomere fluorescence comparisons between untreated and TPA-treated cases are significant (P<0.05), except P>0.05 (not significant) for hair bulb, infundibulum and interfollicular epidermis of G1 Terc$^{-/-}$ mice.

To further test whether the longest telomeres map to stem cell compartments and to prevent the influence of possible telomerase activation on telomere length, topographic telomere length maps were generated from first generation telomerase-deficient G1 Terc$^{-/-}$ mice (FIG. 1b) (Blasco et al., 1997; Ramirez et al., 1997). Similarly to wild-type skin, G1 Terc$^{--}$ skin showed an enrichment of cells with the longest telomeres (1800-3000 a.u. of telomere fluorescence) in the bulge area of the hair follicle with the shortest telomeres at the interfollicular epidermis (FIG. 1b), thus confirming that the longest telomeres are enriched at the stem cell compartment. However, the percentage of cells with 1800-3000 arbitrary units of telomere fluorescence was lower in all skin compartments compared to control wild-type mice, in agreement with the fact that G1 Terc$^{-/-}$ mice lack telomerase activity (FIG. 1b). Similarly, average telomere fluorescence was lower in G1 Terc$^{-/-}$ mice compared to wild-type mice in all skin compartments (FIG. 6). These results demonstrate that the cells with the longest telomeres are enriched at the hair follicle stem cell compartment, while the cells with the shortest telomeres are located in the outer skin layers, indicating that telomeres are shorter as cells go from the more primitive to the more differentiated skin compartments. Furthermore, these results indicate that telomerase activity is important to maintain the overall telomere length of different skin compartments in the mouse, as first generation telomerase-deficient G1 Terc–/– showed a marked decrease in telomere length compared to age-matched wild-type controls in all skin compartments.

Figure 1C:
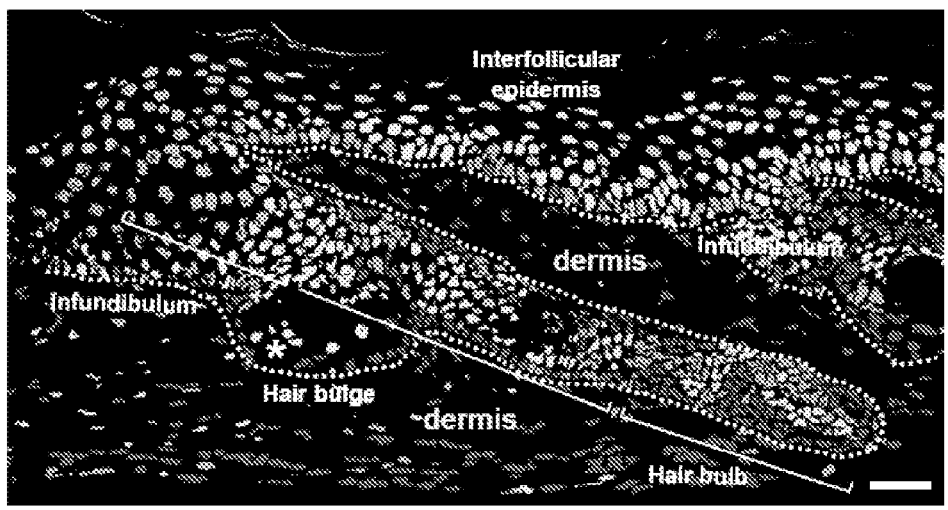
Figure 1C:
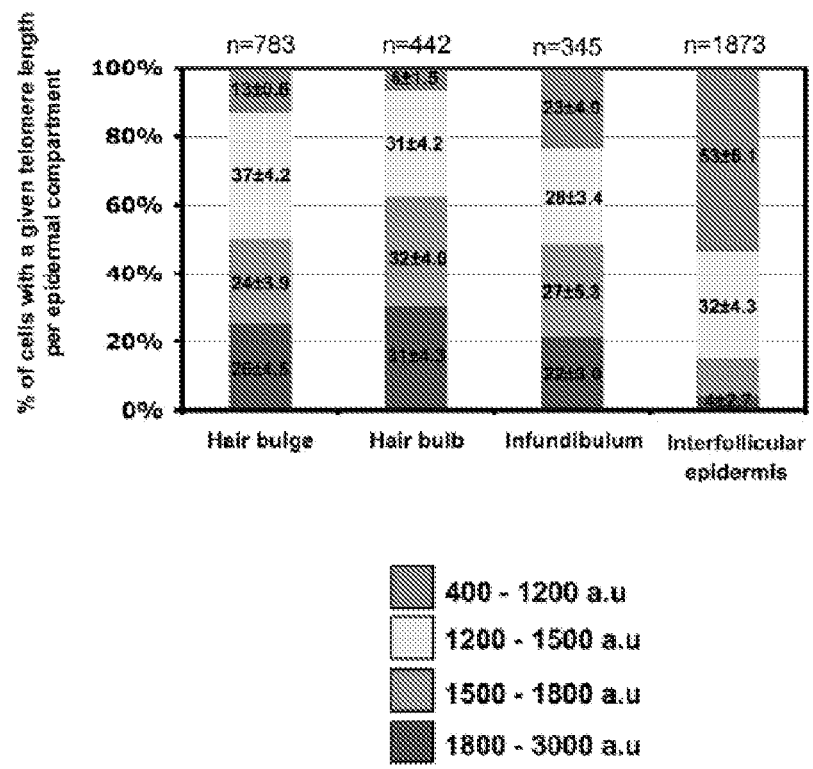
Figure 1D:
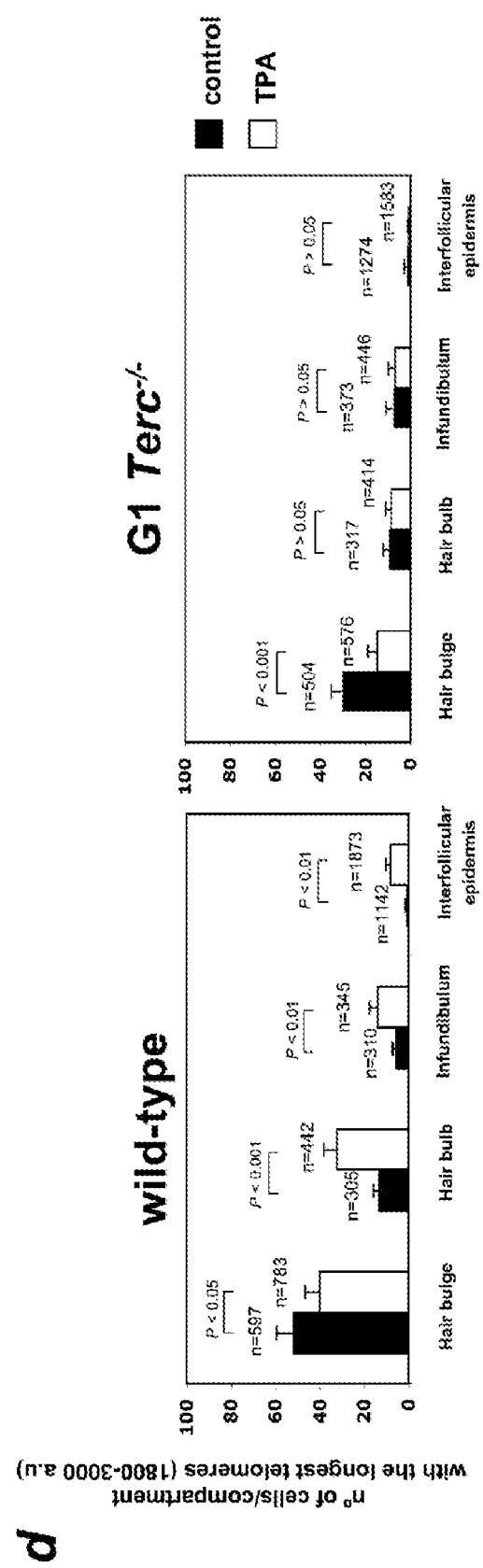
Figure 1E:
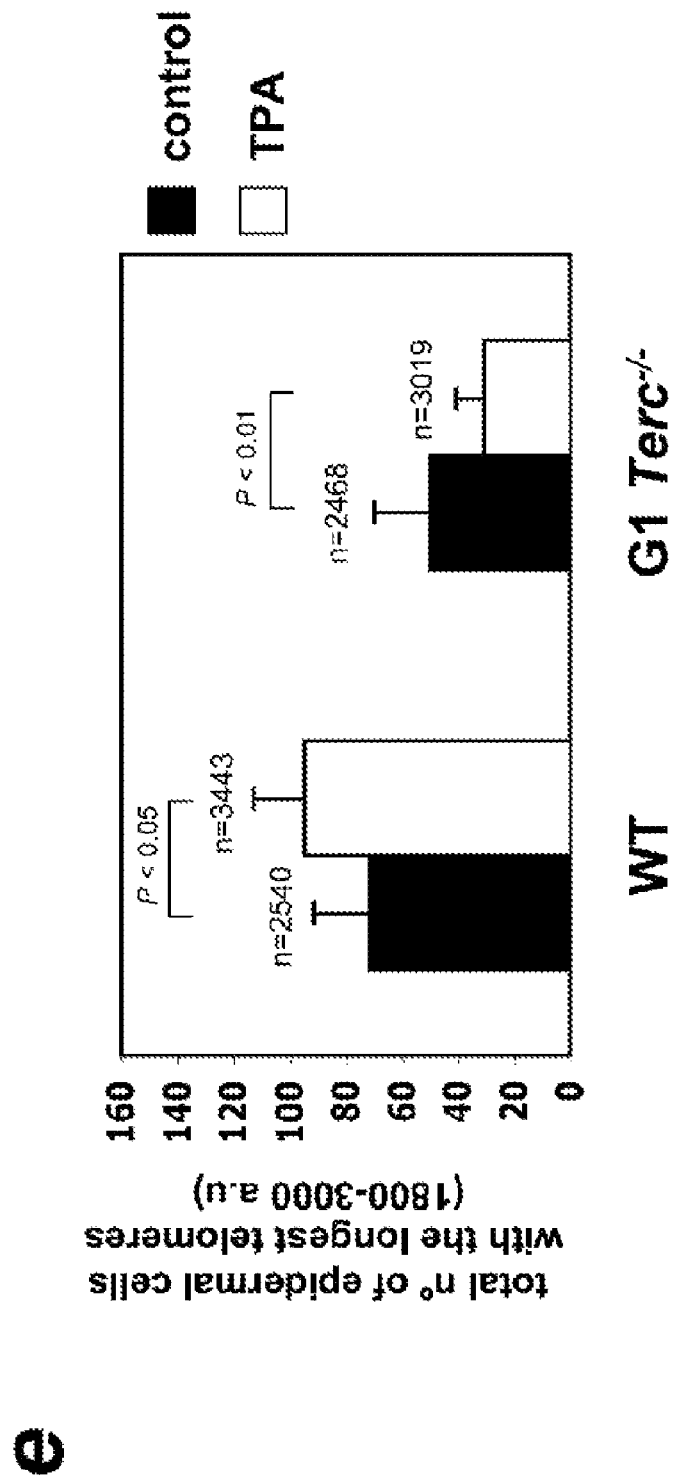

To address whether cells with the longest telomeres within the hair follicles also show characteristic stem cell behaviour, wild-type and G1 Terc–/– mice were treated with the mitogenic stimulus TPA, which triggers migration and proliferation ("mobilization") of stem cells out of the niches in the TA compartments. Wild-type TPA-treated skin showed a decreased in the percentage of the cells with the longest telomeres at the hair bulge with an accumulation of these cells to the TA compartments (hair bulb and infundibulum), coinciding with an enlargement of these compartments and thickening of the interfollicular epidermis (compare FIG. 1c to FIG. 1a). As a consequence, the absolute number of cells containing the longest telomeres decreased at the hair bulge and concomitantly increased in the other epidermal compartments (FIG. 1d; significant in all cases). Furthermore, the total number of epidermal cells showing 1800-3000 a.u. of telomere fluorescence significantly increased in TPA-treated skin compared to the untreated wild-type skin (significant, P<0.05; FIG. 1e), suggesting net telomere elongation associated to TPA-induced proliferation in TA compartments (FIG. 1e). Telomere length histograms also showed decreased frequency of long telomeres in hair bulge cells upon TPA treatment, which was concomitant with increased telomere length in cells located at the TA compartment and the interfollicular epidermis (FIG. 6).

To address whether these effects were dependent on telomerase activity, TPA-treated G1 Terc$^{-/-}$ skin was studied. Similarly to TPA-treated wild-type skin, G1 Terc$^{-/-}$ skin showed a reduction of the percentage of cells with the longest telomeres at the hair bulge (FIG. 1c) coincidental with an enlargement of the TA compartments (compare FIG. 1c to FIG. 1b), suggesting that these cells mobilized and proliferated in response to TPA. However, in contrast to TPA-treated wild-type skin, G1 Terc$^{-/-}$ TPA-treated skin did not show increased percentage of cells with the longest telomeres at the TA compartments and the interfollicular epidermis (FIG. 1c,d). Indeed, the total number of epidermal cells showing the longest telomeres was decreased in G1 Terc$^{-/-}$ TPA-treated skin compared to untreated skin (very significant P<0.01; FIG. 1e), suggesting telomere shortening as the result of TPA-induced proliferation in the absence of telomerase activity. In agreement with this, telomere length histograms of TPA-treated G1 Terc$^{-/-}$ mice showed a decreased frequency of long telomeres in all hair follicle compartments (FIG. 6). These results indicate that telomerase actively participates in telomere maintenance upon migration and proliferation (mobilization) of stem cells in response to TPA treatment, in contrast, mobilization of stem cells in the absence of telomerase results in telomere shortening in all skin compartments in G1 Terc$^{-/-}$ mice.

Example 3

Isolated Hair Bulge Cells from K15-EGFP Mice show the Longest Telomeres

Figures 7A, 7B:
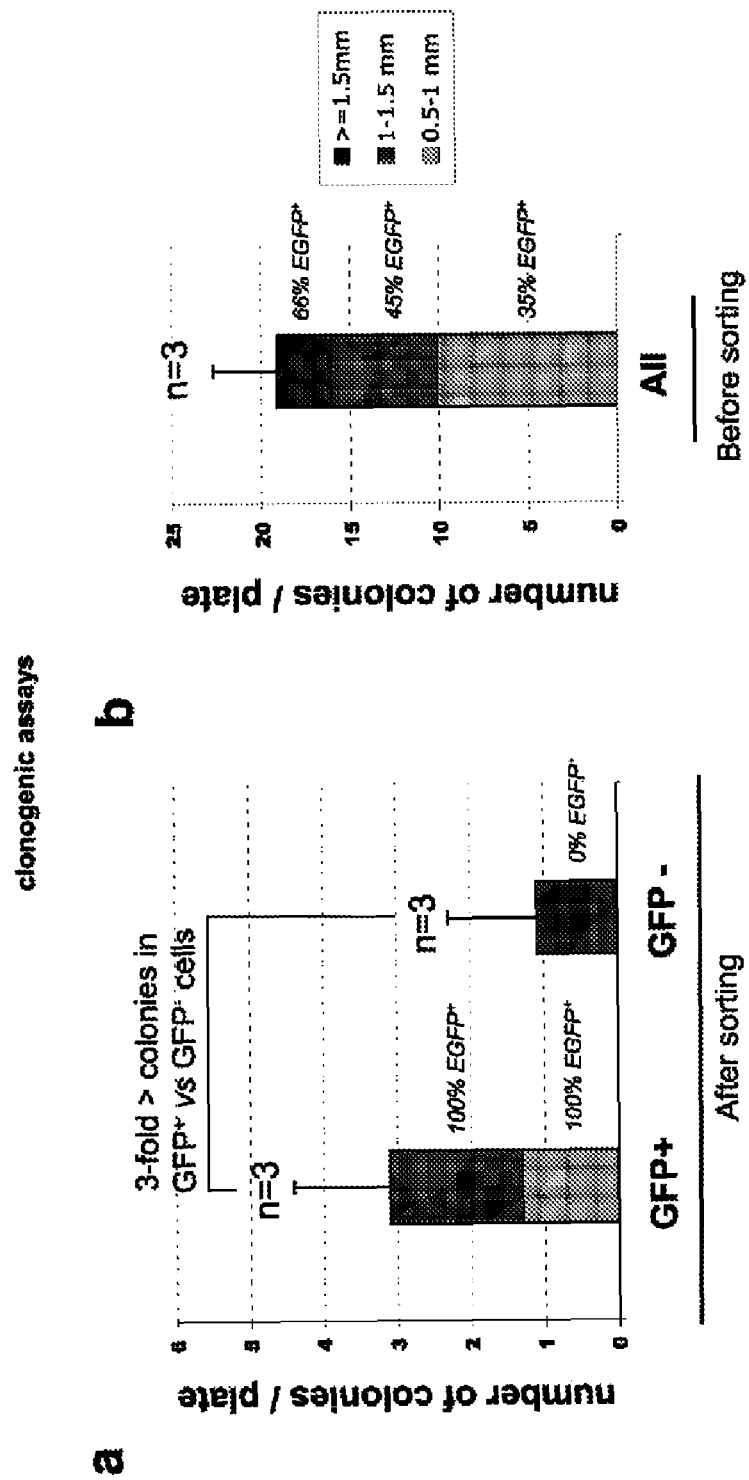
FIGS. 7A and 7B. Clonogenic potential of GFP+ and GFP− K15-EGFP sorted cells.
Figures 8A, 8B, 8C:
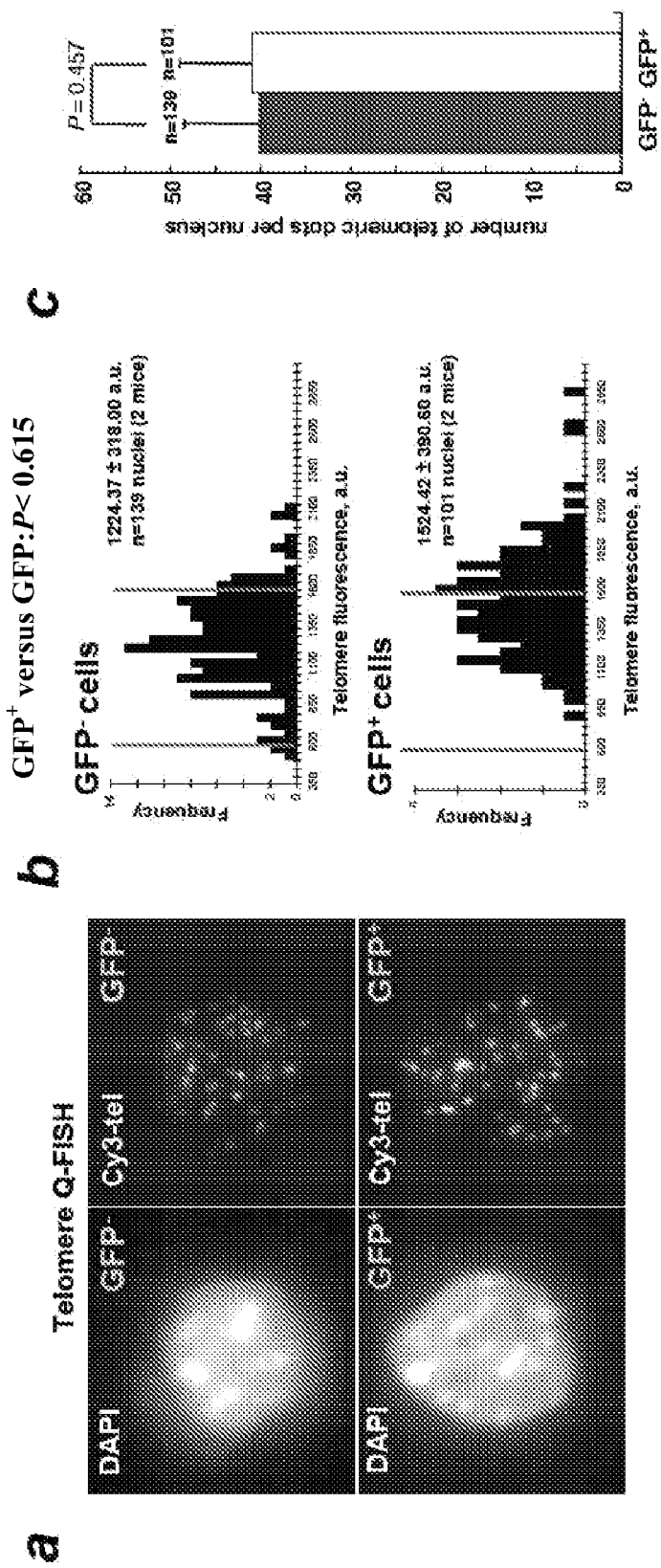
FIGS. 8A-8H. Isolated hair bulge stem cells from K15-EGFP mice show the longest telomeres and telomerase activity.
Figures 8D, 8E:
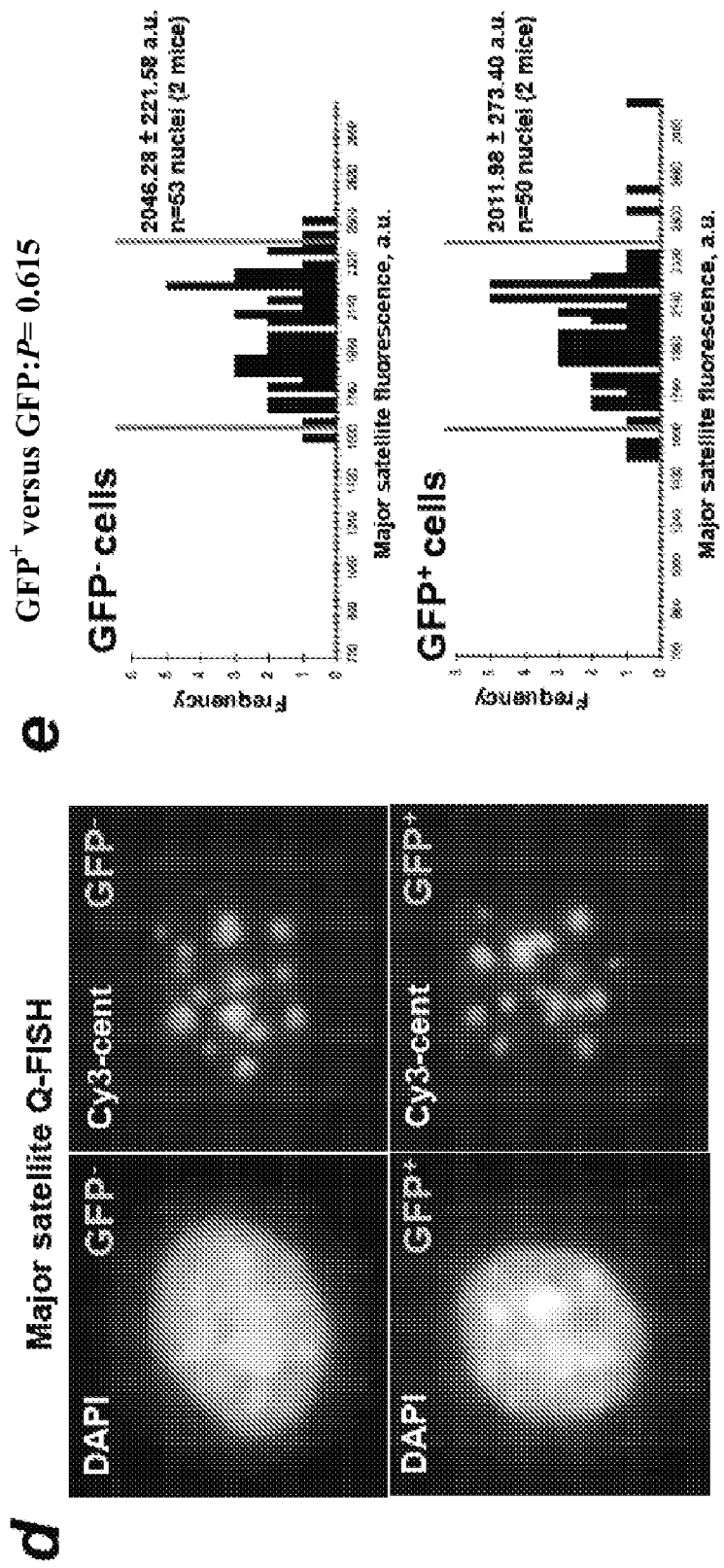
Figures 8F, 8G, 8H:
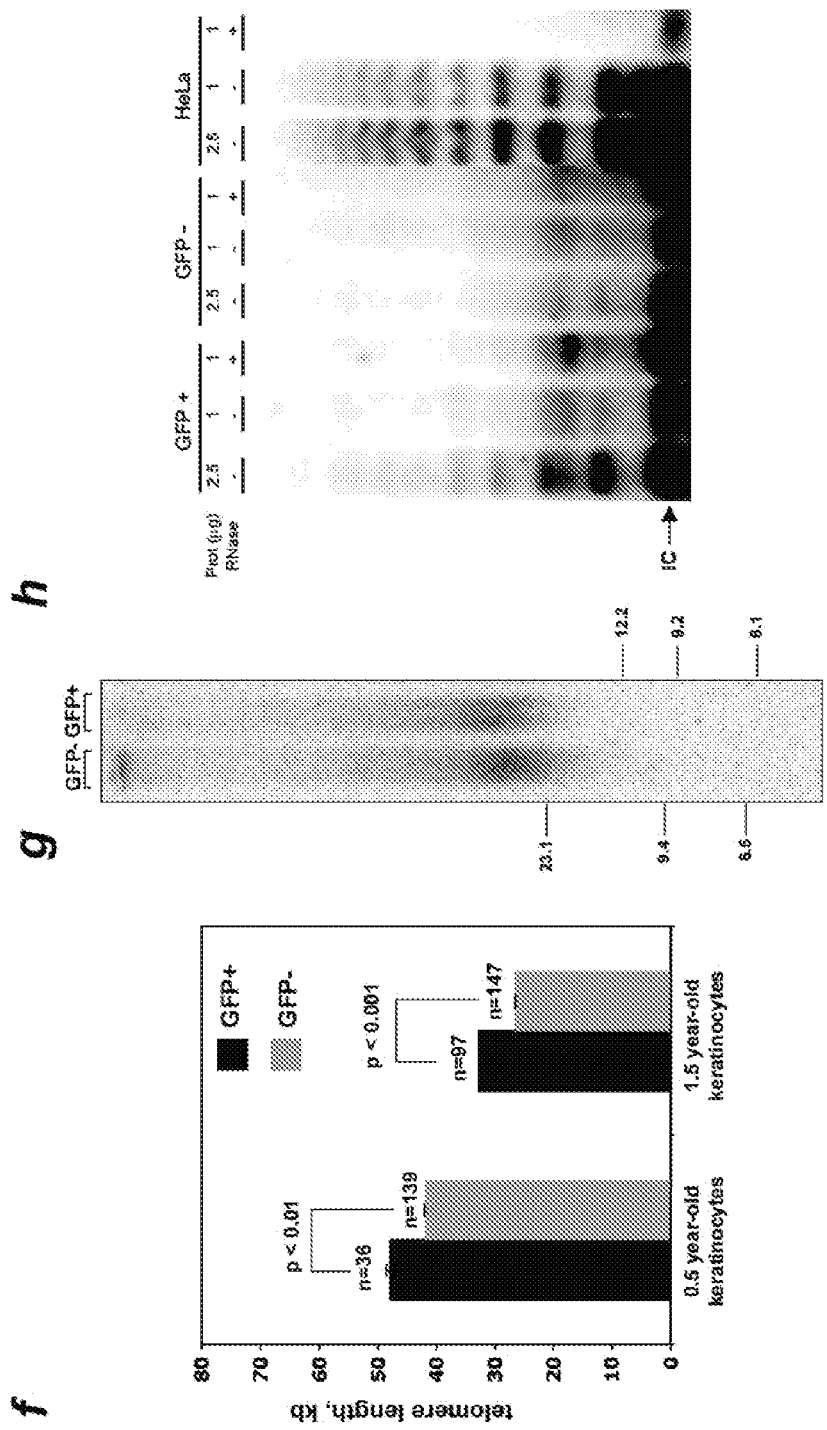

The results described above indicate that cells with the longest telomeres are enriched at stem cell compartments. To further address this issue, purified skin hair bulge cells (hair follicle stem cell compartment) was studied in order to determine whether these cells also showed the longest telomeres. For this, K15-EGFP transgenic mice were used, in which the K15-expressing hair bulge cells are identified by a positive GPF expression (Morris et al., 2004) (Experimental Procedures). GFP-positive cells from these mice have been previously shown to have stem cell properties and to contribute to some aspects of skin regeneration (i.e., wound healing) as well as to have a higher in vitro clonogenic potential than GFP-negative cells (Morris et al., 2004; Ito et al., 2005). To this end, we sorted K15-EGFP skin keratinocytes into GFP-negative (GFP–) and GFP-positive (GPF+) cell populations (Experimental Procedures). In agreement with previously published data, approximately 4% GFP+ cells were recovered from total K15-EGFP tail epidermis reflecting on the relatively low abundance of hair bulge Cells with stem cell properties (Morris et al., 2004; Ito et al., 2005). As control for enrichment in stem cells, in vitro clonogenic assays were performed, where individual colonies are proposed to derive from single stem cells (Flores et al., 2005). Purified GFP+ cells formed 3 times more colonies than GFP− cells in clonogenic assays, in agreement with the notion that they are enriched in hair bulge stem cells (Morris et al., 2004; Ito et al., 2005) (FIG. 7a). More over, GFP+ cells were more abundant in the big-size colonies when using total unsorted K15-EGFP keratinocytes, also supporting the notion that K15-GFP+ cells are enriched in stem cells (FIG. 7b). Importantly, using conventional Q-FISH on cytospin-plated interphasic cells (Experimental Procedures), it was found that the GFP+ keratinocytes showed longer telomeres than the GFP− keratinocytes (highly significant, $P<0.001$; FIG. 8a,b). To rule out possible differences in ploidy, the number of telomere signals per nuclei were quantified and found no significant differences between sorted GFP+ and GFP− cells ($P=0.457$; FIG. 8c). In addition, differences in telomere length due to differential "probe accessibility" could be ruled out by performing Q-FISH with a centromeric major satellite probe as control (Experimental Procedures; FIGS. 8d,e). The decline in telomere length between GFP+ and GFP− cells was validated using an independent quantitative telomere FISH technique based on flow cytometry known as Flow-FISH (Experimental Procedures). Two mouse cell lines of known telomere length were also included in the Flow-FISH analysis in order to convert telomere fluorescence values into kilobases (Example 1). Again, purified K15-EGFP+ cells showed significantly longer telomeres than K15-EGFP− cells both in young (0.5 year-old) and old mice (1.5 year-old) ($P<0.01$; FIG. 8f). We estimated a telomere shortening of 6 Kb between K15-EGFP+ hair bulge keratinocytes (a population enriched in stem cells) and K15-EGFP− keratinocytes (a population enriched in differentiated cells) (FIG. 8f), which corresponds to an approximately 16% decline in telomere length. Finally, longer telomeres in K15-EGFP+ hair bulge cells were also confirmed when using a Southern blot-based technique known as "telomere restriction analysis" or TRF, which is not based on fluorescence (Example 1) (FIG. 8g). Of interest, concomitantly with the decreased telomere length in the differentiated skin compartments, it was also observed a reduction in telomerase activity when comparing K15-EGFP+ hair bulge keratinocytes and K15-EGFP− keratinocytes (FIG. 2h), which may contribute to the observed telomere attrition associated to differentiation (see also FIGS. 1, 4 and 5).

Figure 9A:
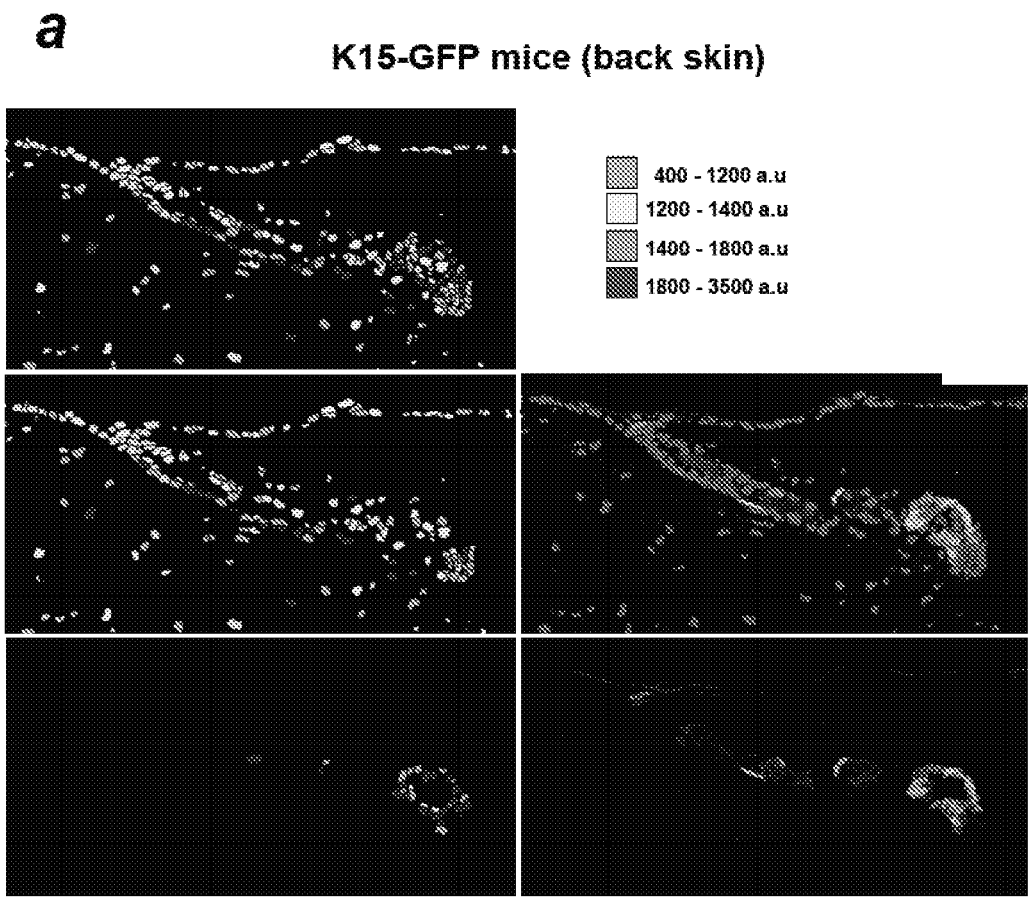
FIGS. 9A-9C. Telomapping maps the longest telomeres to the EGFP$^+$ cells in K15-EGFP skin sections.
Figure 9B:
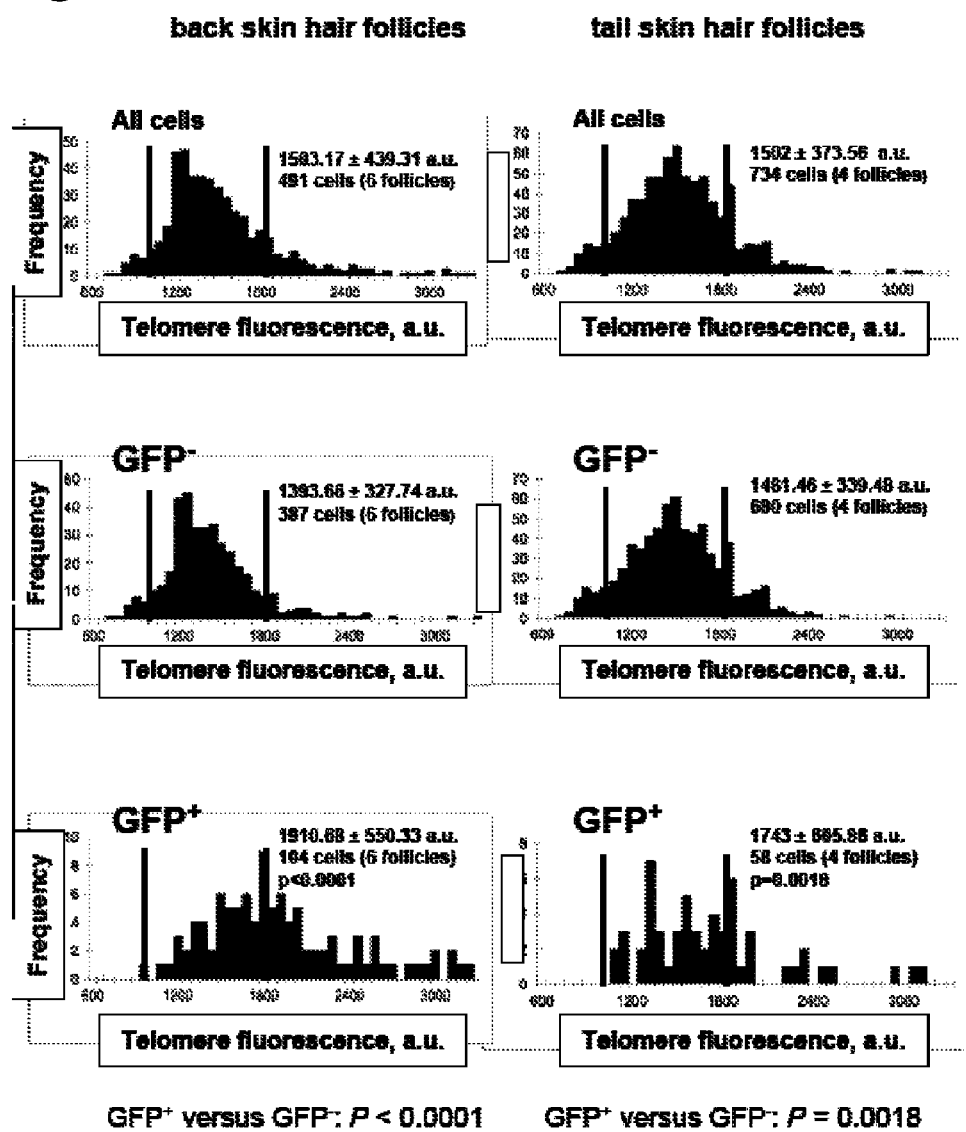
Figure 9C:
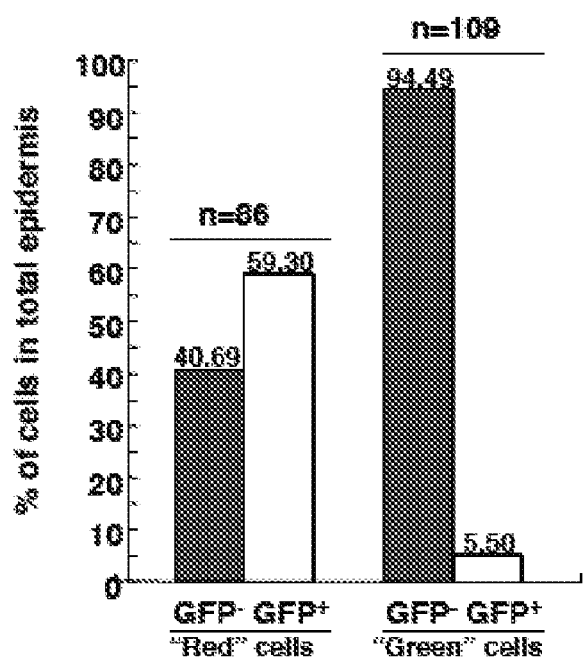

Next, GFP fluorescence was combined with confocal telomere QFISH directly on skin sections from K15-EGFP mice to address whether the GFP+ cells within the hair follicle co-localized with the longest telomeres on skin histological sections (Experimental Procedures). As shown in FIG. 3a, GFP+ cells precisely localized to the hair follicle bulge, in agreement with the fact that K15 labels stem cell niches (Morris et al., 2004). Interestingly, these GFP+ cells also showed the longest telomeres compared to the GFP− cells (highly significant, $P<0.001$; FIG. 9a,b). Telomapping of GFP+ and GFP− skin cells also indicated a 17% decrease in telomere length between both compartments, similarly to the decrease obtained by Flow-FISH (see above). In addition, it was calculated that 59.3% of the cells with the longest telomeres (red color after telomapping) were GFP+, while this percentage dropped to 5.5% in cells with the shortest telomeres (green after telomapping) (FIG. 9c). All together, these results suggest that more than 50% of epidermal cells with the longest telomeres are K15-expressing hair bulge cells (GFP+ cells), which in turn have been shown to be enriched in stem cells (Morris et al., 2004; Ito et al., 2005) (see also FIG. 7).

Example 4

The Longest Telomeres are a General Feature of Different Mouse Stem Cell Compartments (Small Intestine, Cornea, Testis, Brain)

Figure 10A:
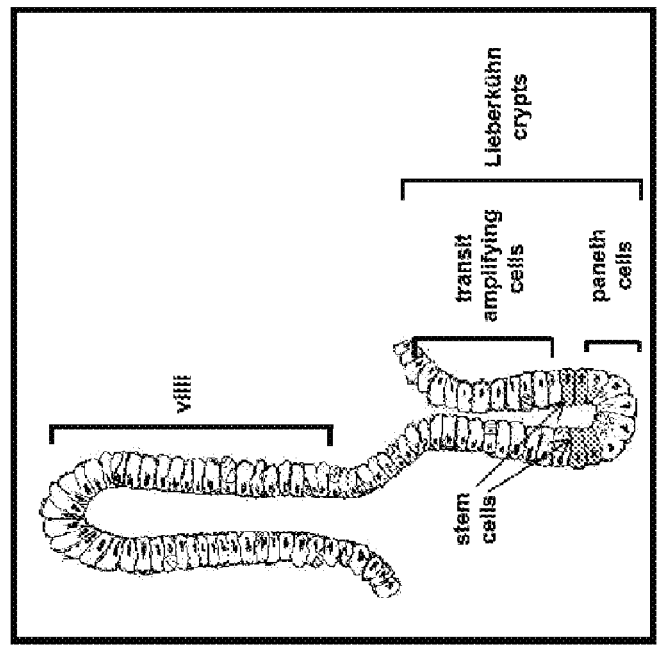
FIGS. 10A-10G. Cells with the longest telomeres locate to stem cell compartments in different origin mouse tissues.
Figure 10B:
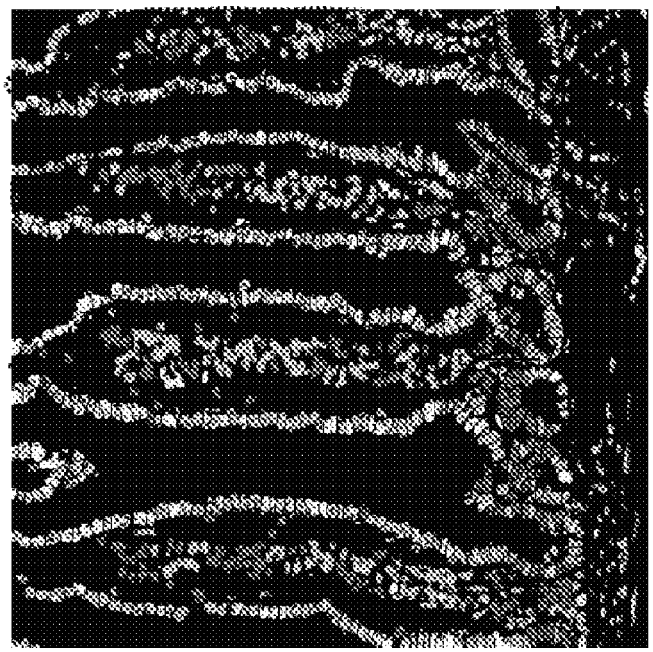
Figure 10C:
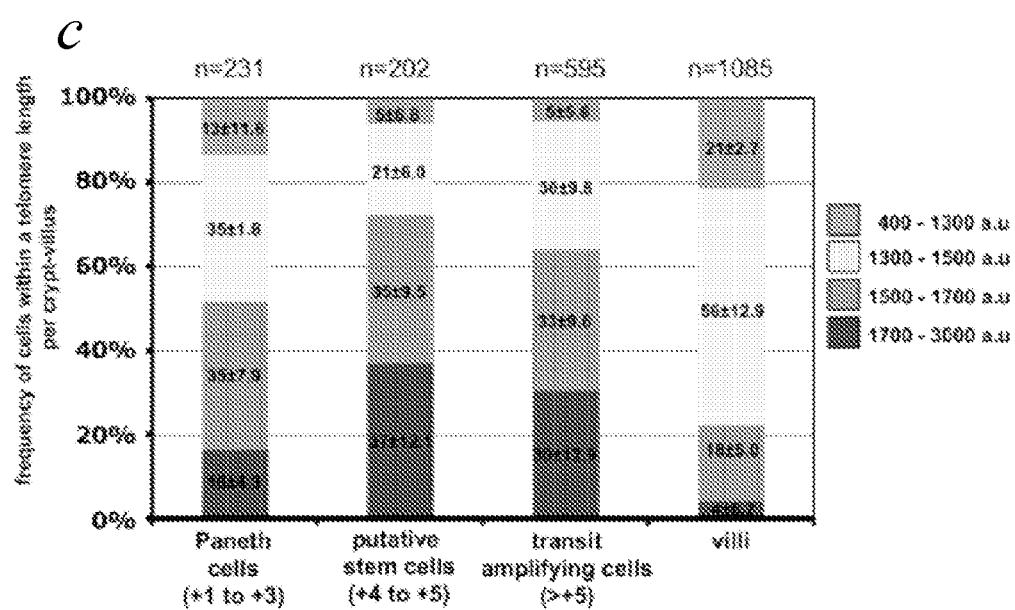
Figure 10D:
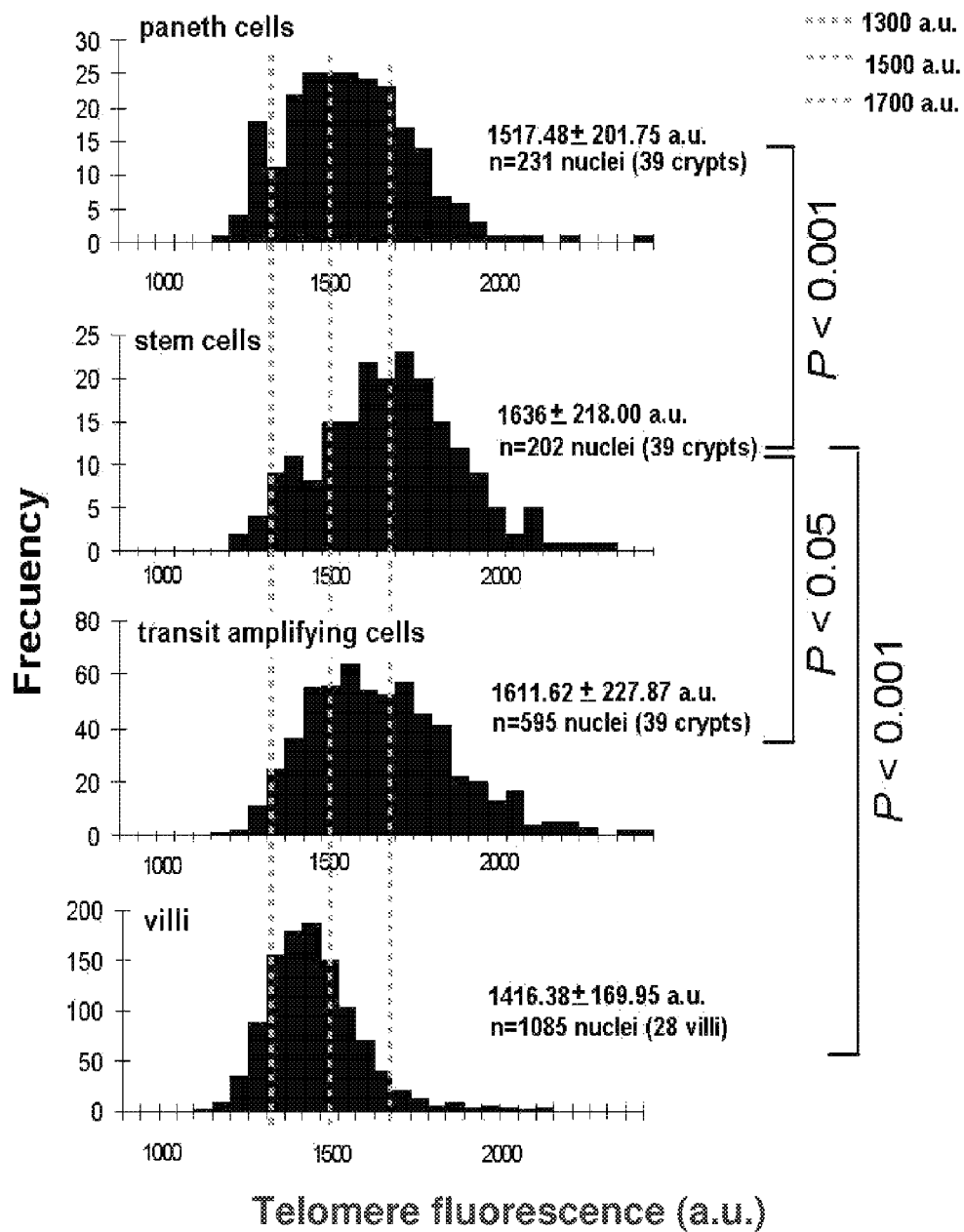

All together, the above-described findings suggest that the most primitive compartments within the skin are characterized by having cells with the longest telomeres compared to the more differentiated compartments. To generalize and test this hypothesis to other tissues besides the skin, telomapping was performed in histological sections from small intestine, cornea, testis and brain, where the corresponding stem cell compartments have been well characterized in the mouse. In mice, the small intestine stem cell niche is localized to the bottom of the intestinal crypts at approximately the +4 position, right above the Paneth cells (positions +1 to +3) and below the TA compartment (position >+5), whereas the most differentiated cells are located at the intestinal villi (see scheme in FIG. 10b) (Gregorieff et al., 2005; Marshman et al., 2002). Topographic telomere length maps of small intestine histological sections localized the cells with the longest telomeres (1700-3000 a.u. of telomere fluorescence; see Experimental Procedures for criteria on telomere length ranges) above the Paneth cells and in the TA compartment (FIG. 10a,c), in agreement with the known location of stem cell niches in the small intestine (Gregorieff et al., 2005; Marshman et al., 2002). In particular, between positions +1 to +3 (Paneth cells) only 16% of the cells showed the highest telomere fluorescence, while this increased to 37% between +4 and +5 positions (putative stem cells) (FIG. 10a,c). This percentage slightly decreased to 30% in the TA compartment (cells above the +5 position), further dropping to 4% in the differentiated villi area (FIG. 10a,c). The differences in telomere fluorescence between the stem cell compartment and the other compartments were significant for all comparisons (Wilcoxon's sum test, $P>0.05$; FIG. 4d). Again, this telomere length distribution supports the notion that the longest telomeres are enriched at the most primitive compartments in the small intestine.

Figure 10E:
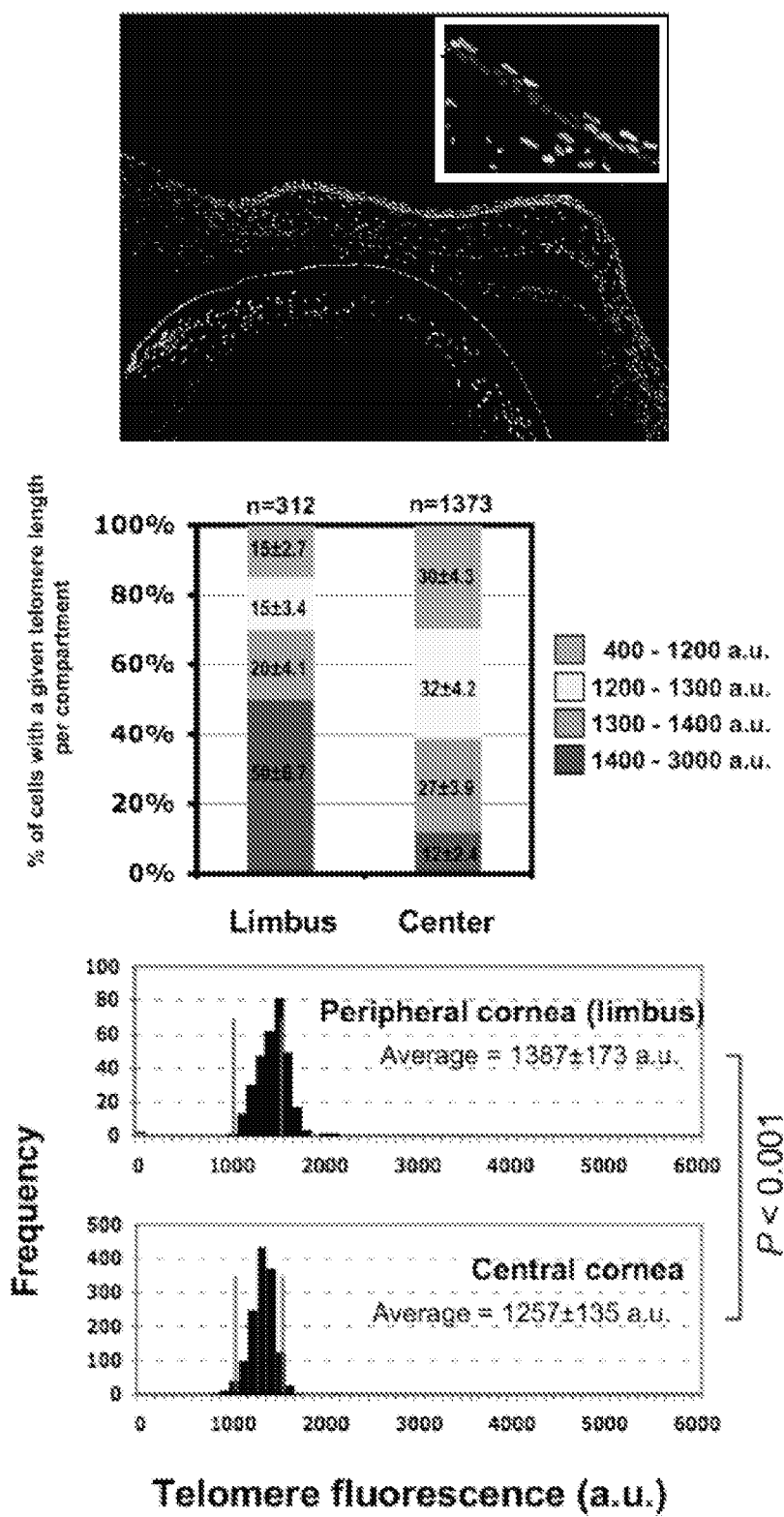

Next, histological telomere length maps were generated for mouse cornea and testis, two other epithelial tissues where the SC compartment has been spatially defined. Corneal stem cells reside at the limbus, the peripheral zone of the cornea lying above the ciliary body (FIG. 10e) (Lavker et al., 2004; Lehrer et al., 1998). From this location, corneal stem cells migrate towards the central corneal epithelium as their differentiation program proceeds (FIG. 4e) (Lehrer et al., 1998). Telomapping of eye sections revealed that an average of 50% of the limbal cells possess the longest telomeres (1400-3000 a.u. of telomere fluorescence; see Experimental Procedures for criteria on telomere fluorescence ranges), a percentage that gradually diminishes as cells move centripetally towards the centre of the cornea (FIG. 10e). The percentage of cells with the longest telomeres further increased to 68% within the limbal basal layer (see insert in FIG. 10e), a compartment where corneal SC are particularly enriched (Lehrer et al., 1998). Comparison of average telomere fluorescence between the limbus and the central cornea further indicated that the corneal stem cell compartment harbours the cells with the longest telomeres (FIG. 4e; highly significant $P<0.001$).

Figure 3C:
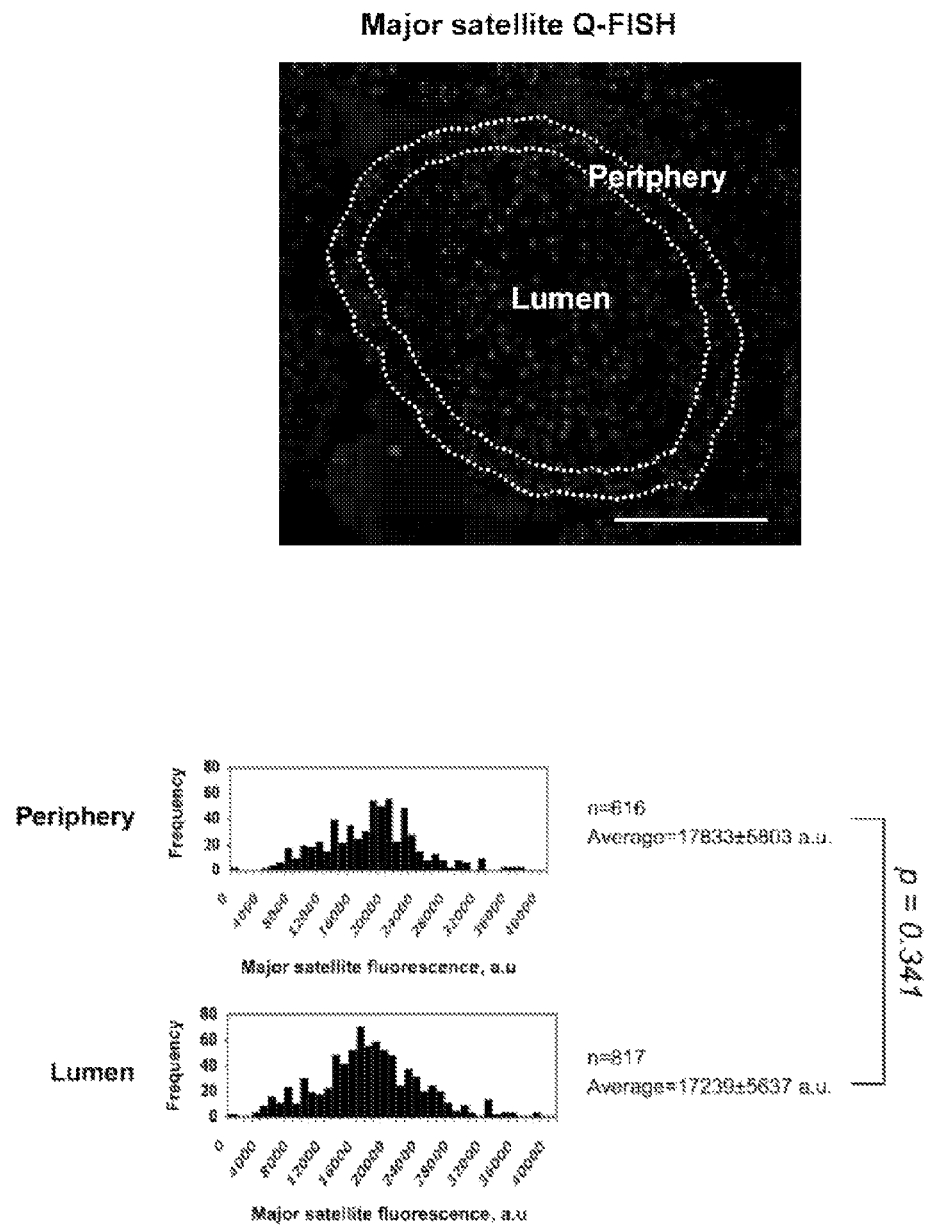
Figure 10F:
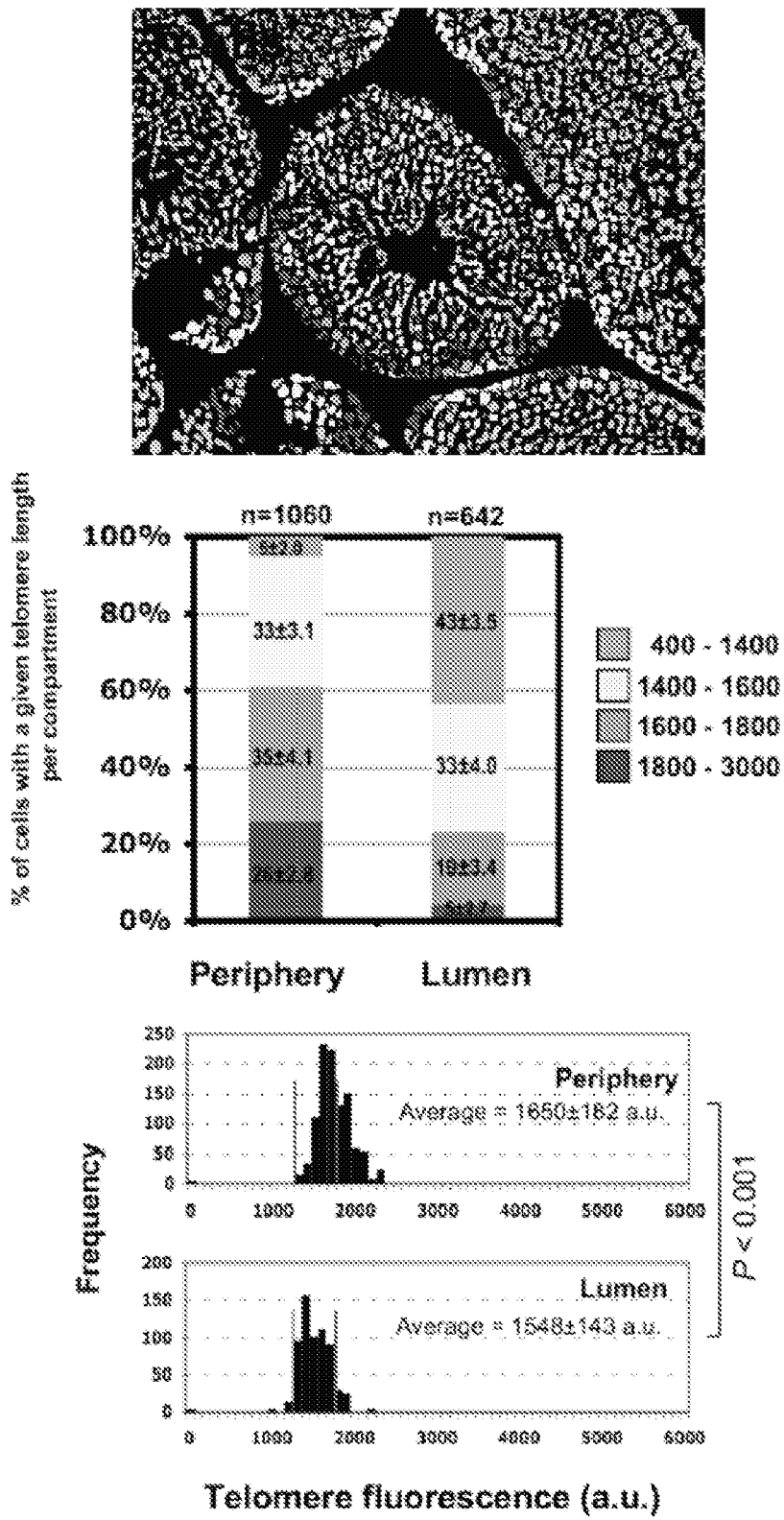

In mouse testis, spermatogenesis starts at the periphery of the seminiferous tubules, where the germ stem cells reside (Guan et al., 2006). By a series of mitotic divisions followed by meiosis, male germ stem cells give rise sequentially to spermatogonia, spermatocyte, spermatid and spermatozoa as they move to a more luminal position (Brinster et al., 2002). Telomapping of testis sections showed that the periphery (1st and 2nd layers) of the seminipherous tubules presented the highest percentage of cells with long telomeres (1800-3000 a.u. of telomere fluorescence; see Experimental Procedures for criteria on telomere fluorescence ranges) (FIG. 10f). In contrast, the lumen zone is highly enriched with cells showing the shortest telomeres. Comparison of telomere fluorescence frequency histograms of the periphery and the lumen areas also indicate a decreased telomere length in the lumen compared to the periphery (highly significant P<0.001; FIG. 10f), reflecting on their differentiation program. Again, these differences in telomere length are unlikely to be due to differences in "probe accessibility" or ploidy between different testis compartments as we did not find significant differences when performing Q-FISH with a centromeric major satellite probe (Example 1; FIG. 3c).

Figure 10G:
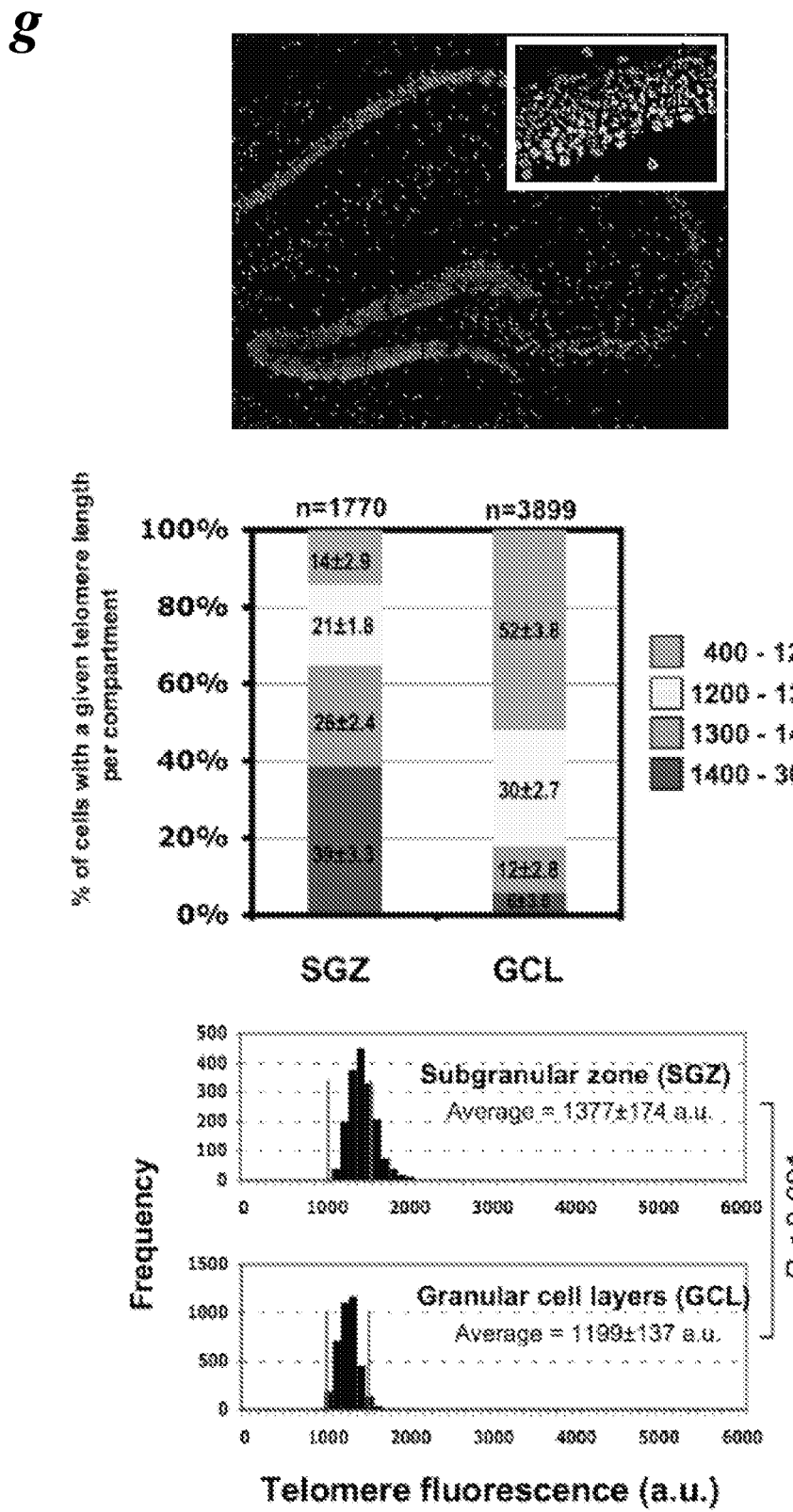

Finally, coronal sections of the adult mouse brain containing areas of neurogenesis were analyzed by telomapping. To date two different spatial stem cell niches have been characterized in the adult mouse brain: the subventricular zone (SVZ) of the lateral ventricule and the subgranular zone (SGZ) at the hippocampus (Alvarez-Buylla & Lim, 2004; Gage, 2000). At the hippocampus, neural stem cells lie in the SGZ, an area located between the granular cell layer (GCL) and the hilus (H) (FIG. 10g). From their basal position, neural stem cells proliferate, migrate and differentiate into the more apical GCL (FIG. 10g) (Gage, 2000). Topographic telomere length mapping revealed that cells with the longest telomeres (1400-3000 a.u. of telomere fluorescence) are enriched at the SGZ, showing progressively shorter telomeres as they enter the abutting GCL (FIG. 10g). Average telomere fluorescence and telomere length distributions also indicated longer telomeres at SGZ compared to GCL (highly significant P<0.001; FIG. 10g), further reflecting that the hippocampus stem cell compartment (SGZ) is enriched in cells having the longest telomeres.

Example 5

Telomere Shortening with Age in Mouse Stem Cell Compartments

Figure 11A:
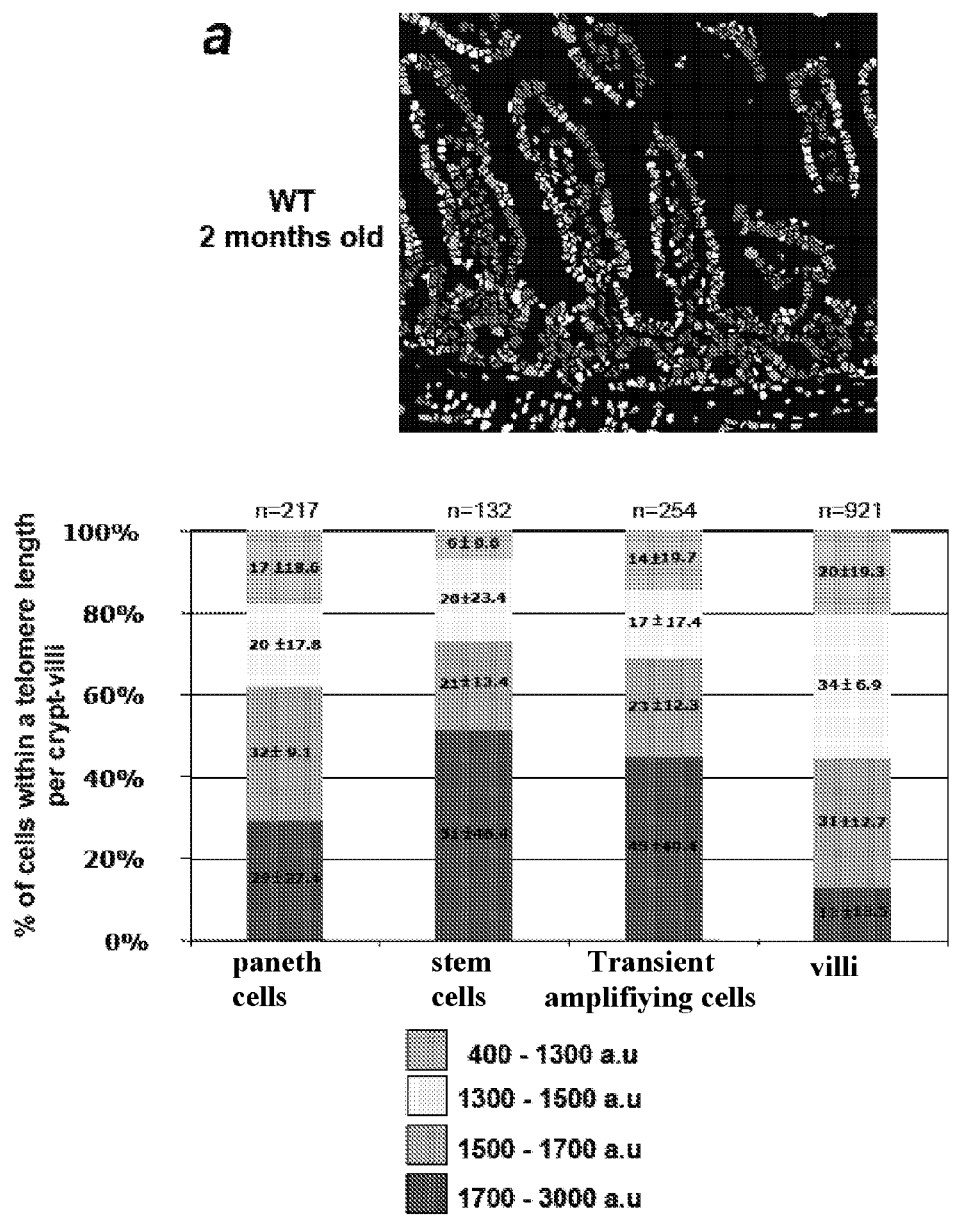
FIGS. 11A-11E. Telomere shortening with age in mouse stem cell compartments.
Figure 11B:
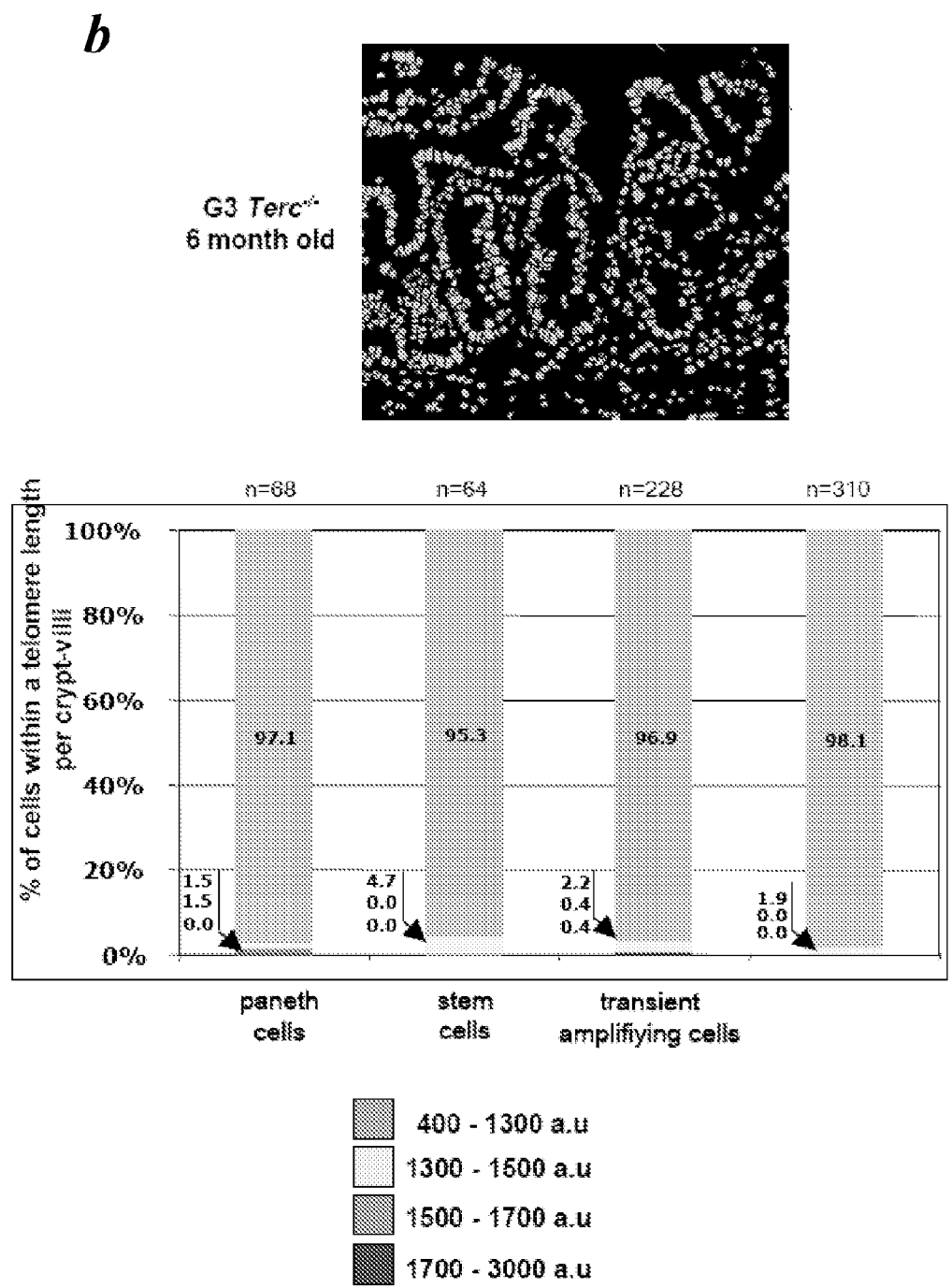
Figure 11C:
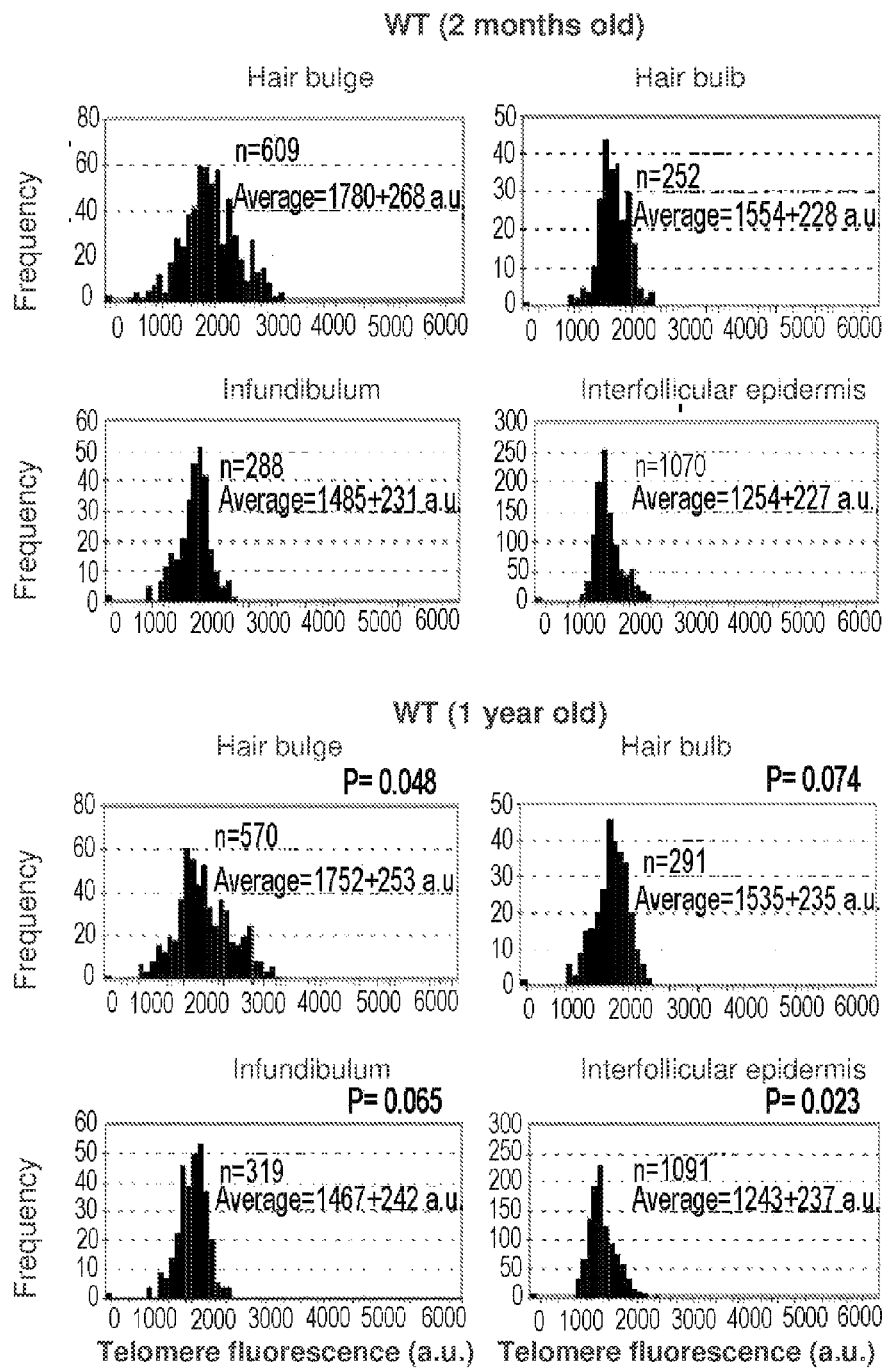

Next, telomapping was used to address whether telomeres shorten in different mouse stem cell compartments with increasing age, which in turn could contribute to stem cell dysfunction with age. A role for telomere shortening in mouse aging and stem cell aging was previously suggested by the reduction in both median and maximum life-span (Garcia-Cao et al., 2005) as well as in stem cell functionality (Flores et al., 2005) found in early generation Terc$^{-/-}$ mice which is progressively aggravated with increasing mouse generations concomitant with gradual reduction in telomere length (Garcia-Cao et al., 2005; Flores et al., 2005). Telomapping revealed that both the percentage of cells with the longest telomeres (FIG. 11a), as well as the average telomere length (FIG. 11c), decreased in all skin compartments at 2 years of age in wild-type C57B16 mice. Similarly, average telomere length at the hair bulge cells decreased significantly from 1780±268 a.u. to 1485±219 a.u. (p<0.001; FIG. 11c), demonstrating telomere shortening in hair follicle stem cells at old ages. In parallel, we performed telomapping in the skin of 6-month-old third generation (G3) Terc-deficient C57B16 mice. As expected, G3 Terc-deficient mice showed a dramatic reduction of the percentage of cells with the longest telomeres, as well as of average telomere length in all skin compartments (FIG. 11b), in agreement with their severe epidermal stem cell dysfunction (Flores et al., 2005). The decreased telomere length with aging in both the stem cell compartment and the more differentiated skin compartments was also confirmed by Flow-FISH analysis using the K15-EGFP reported mouse. In particular, Flow-FISH showed that both sorted GFP+ keratinocytes (enriched in stem cells) and GFP-keratinocytes (enriched in differentiated cells) present a reduction of telomere length when comparing 0.5-year old mice to 1.5 year-old mice (see FIG. 11f). Similarly to skin, we detected telomere shortening in other mouse stem cell compartments including the small intestine, cornea, testis and brain when comparing 2 month-old mice to 2 year-old mice (FIGS. 12-15), further supporting the notion that telomeres shorten at old ages in different stem cell compartments of the mouse, which in turn may result in age-related stem cell disfunction.

Figure 11D:
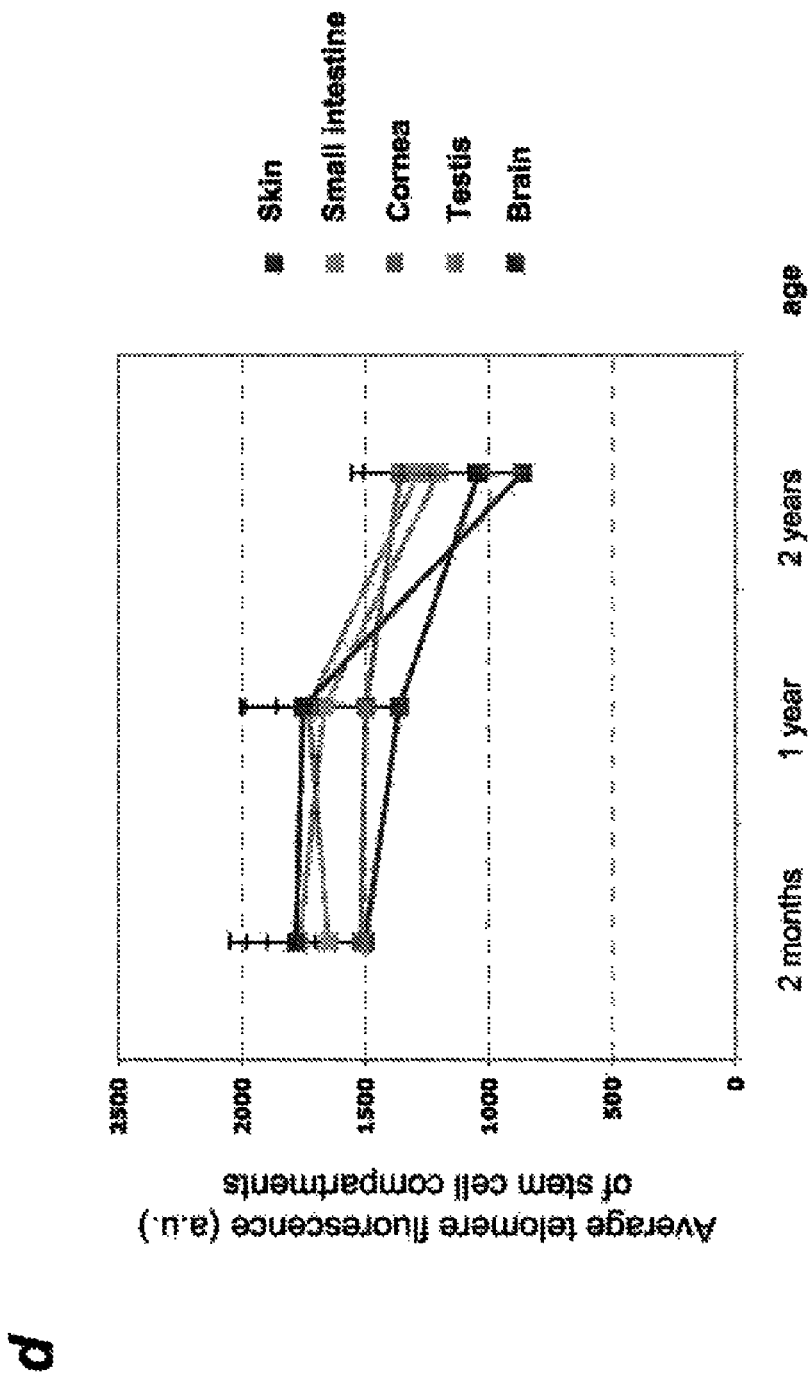
Figure 11E:
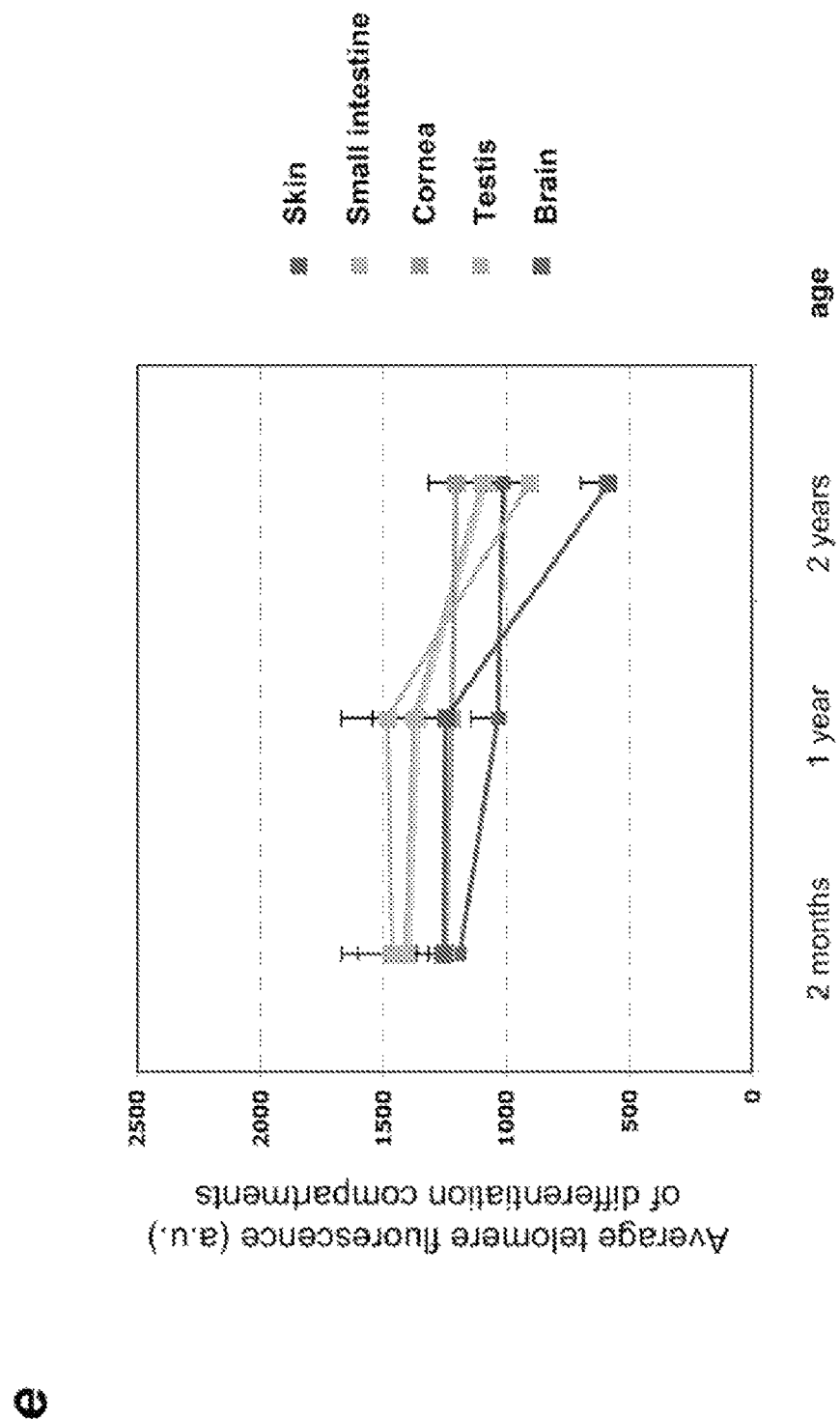
Figure 12A:
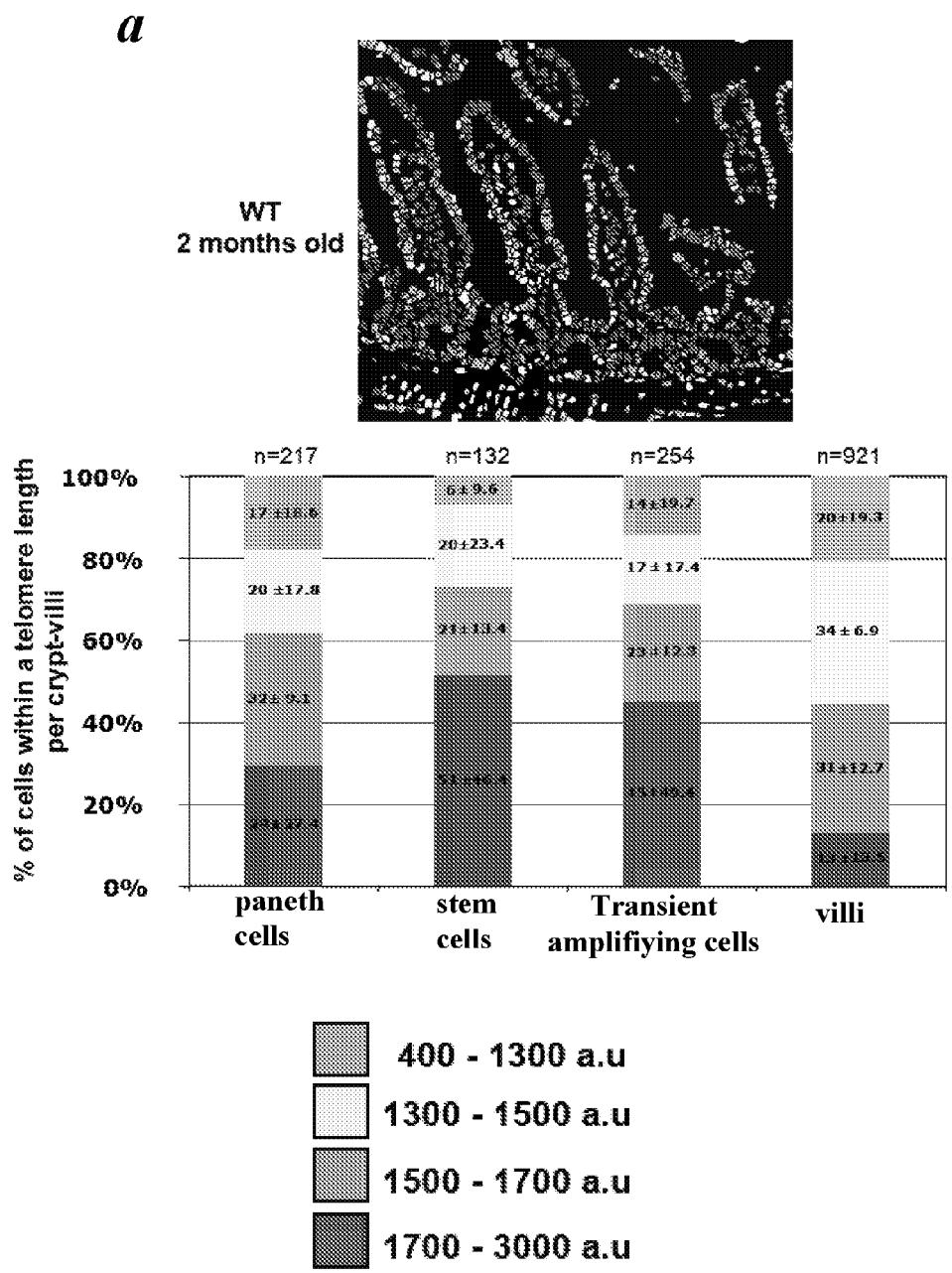
FIGS. 12A-12C. Telomere shortening with age in mouse small intestine stem cells FIGS. 12A and 12B. Representative topographic telomere length maps of small intestine histological sections from wild-type (a) or G3 Terc-deficient (b) mice of the indicated age with confocal telomere Q-FISH images. The different small intestine compartments are indicated. The dashed line separates the epithelial cells (ep) from other cell types from a different origin not studied here: lamina propia (LP), muscularis mucosa (mm) and submucosa (subm). Scale bar corresponds to 70 μm. Nuclei are coloured according to their average telomere fluorescence in arbitrary units (a.u.). Note that the percentage of cells with the longest telomeres decreases in the stem cell compartment when comparing 2 month-old mice with 2 year old-mice. Telomapping of the small intestine of a 6-month old G3 Terc-deficient mouse is shown for comparison FIG. 12C. Telomere length frequency histograms for cells located in the indicated compartments. A statistically significant decrease (P<0.001) in telomere length is observed in all different compartments, including the stem cells, when comparing 2 month-old mice with 2 year-old mice. Average and standard deviation are indicated. More than 20 crypts from at least 2 independent mice per age group and genotype were quantified. n=number of nuclei per compartment analyzed for telomere FISH. Statistical significance values are also indicated.
Figure 12B:
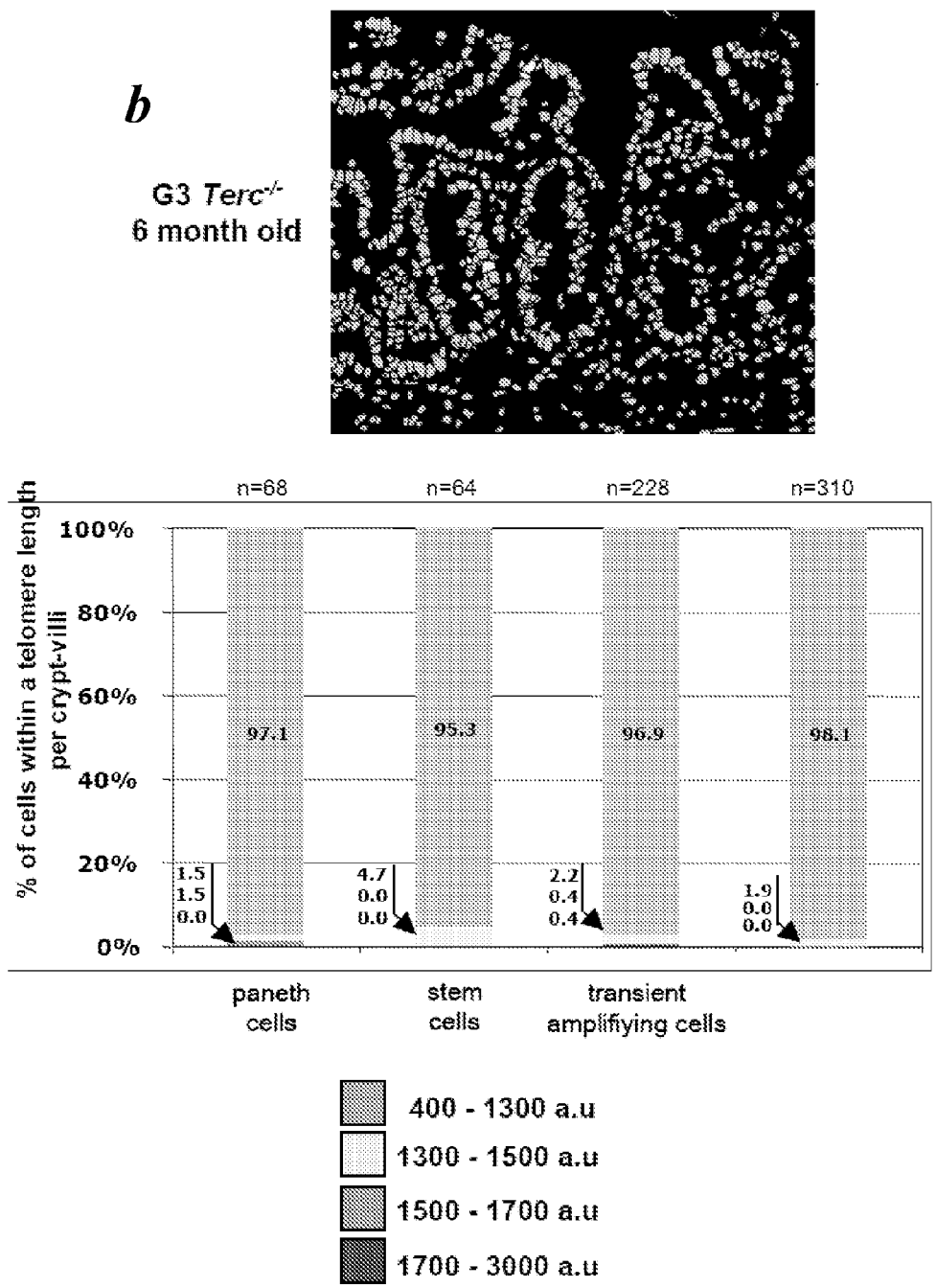
Figure 12C:
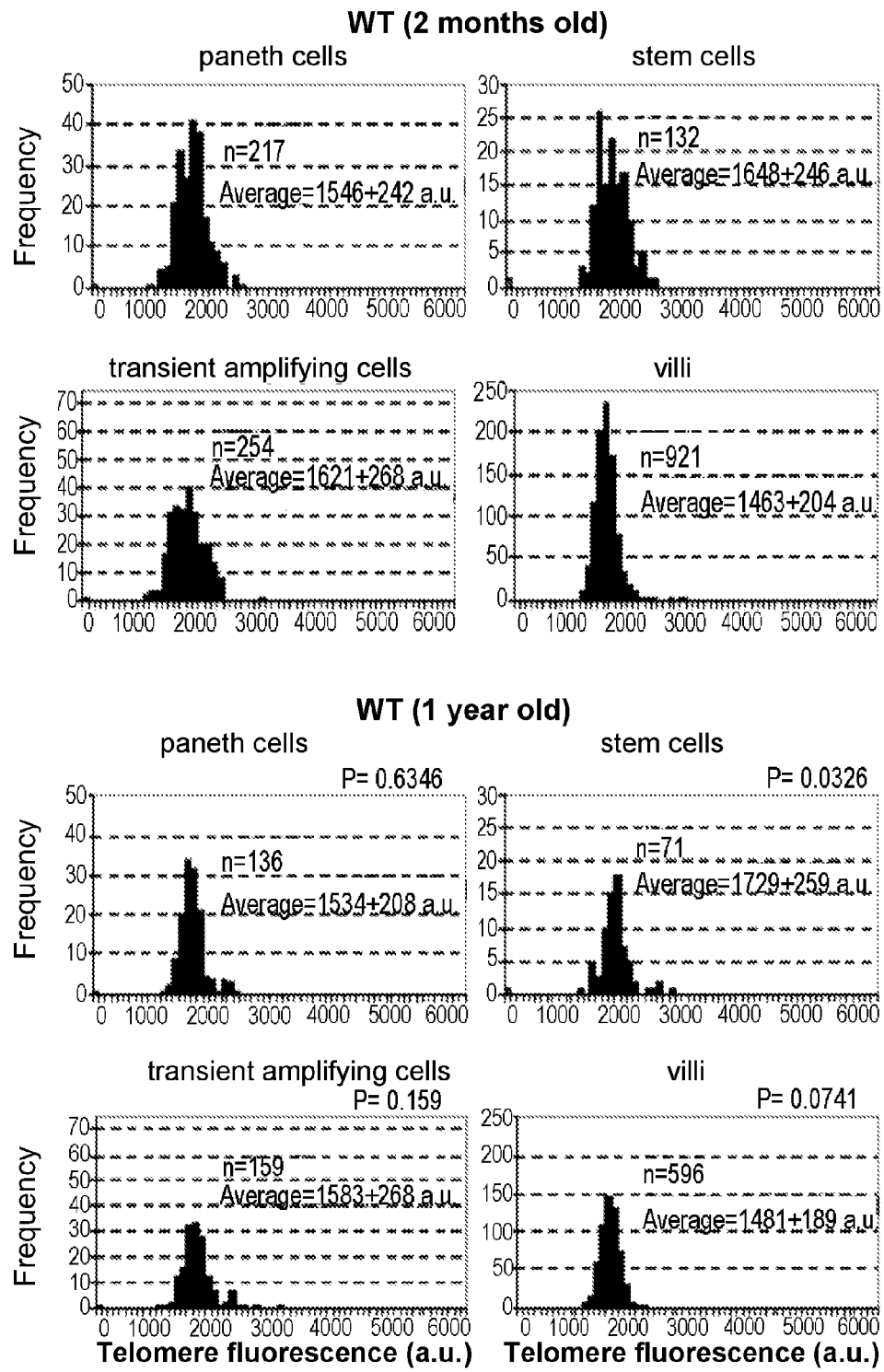
Figure 13:
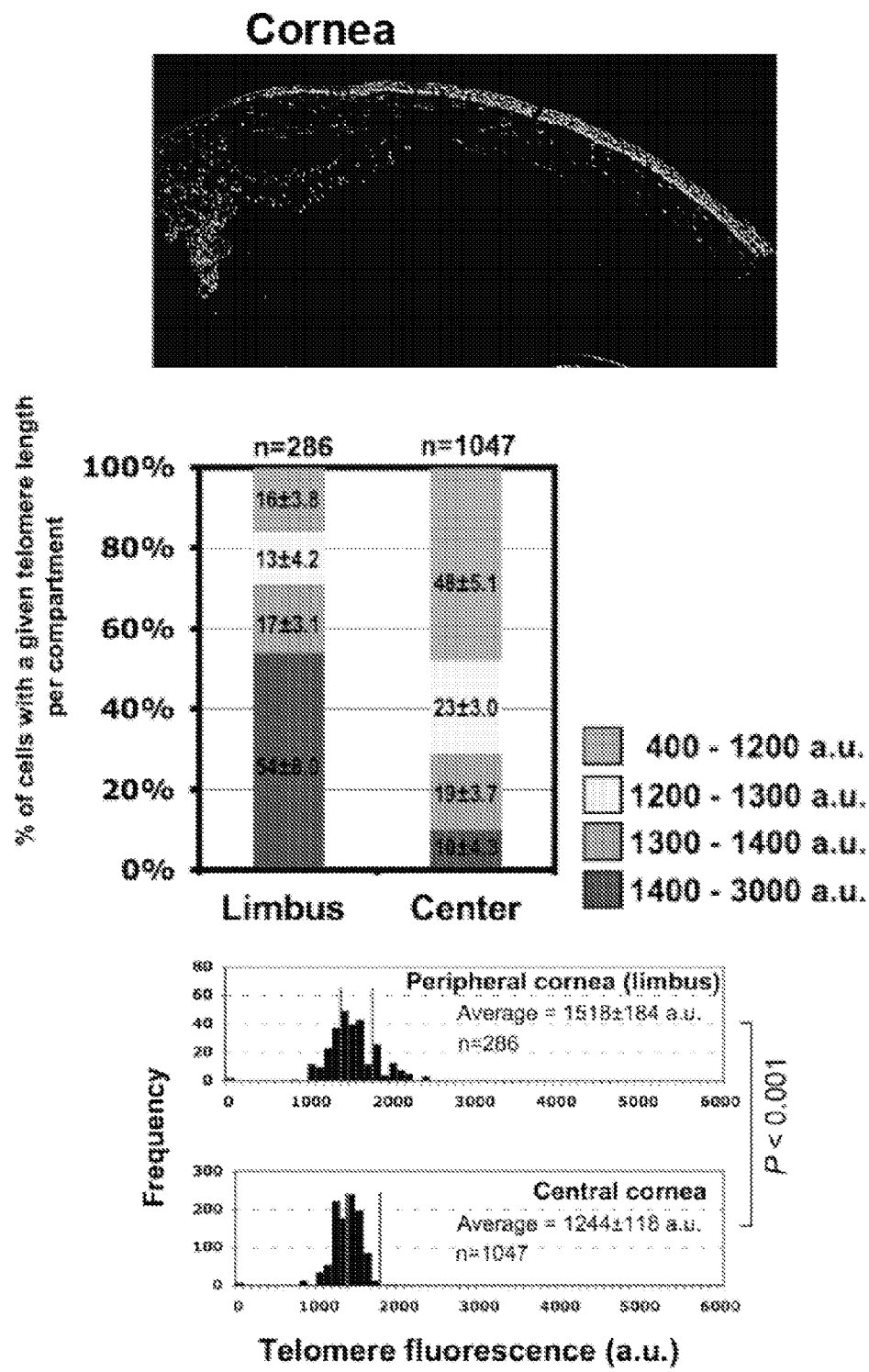
FIG. 13. Telomere shortening with age in cornea epithelium stem cells. Representative topographic telomere length maps of cornea epithelium sections from wild-type mice of the indicated age with confocal telomere Q-FISH images. The different cornea compartments are indicated. CB, ciliary body. The dashed line separates the epithelial cells from other cell types from a different origin not studied here. Nuclei are colored according to their average telomere fluorescence in arbitrary units (a.u.). Middle panels show the percentage of cells containing a given telomere fluorescence within each epidermal compartment. Right panels show telomere fluorescence histograms of nuclei in each compartment. Note that the percentage of cells with the longest telomeres decreases in the stem cell compartment when comparing 2 month-old mice with 2 year old-mice. A total of 6 different cornea images from 3 independent mice were used for quantification. For telomere length frequency histograms, average telomere length and standard deviation are indicated. Number of nuclei analyzed is also indicated. Statistical significance values are also indicated.
Figure 14:
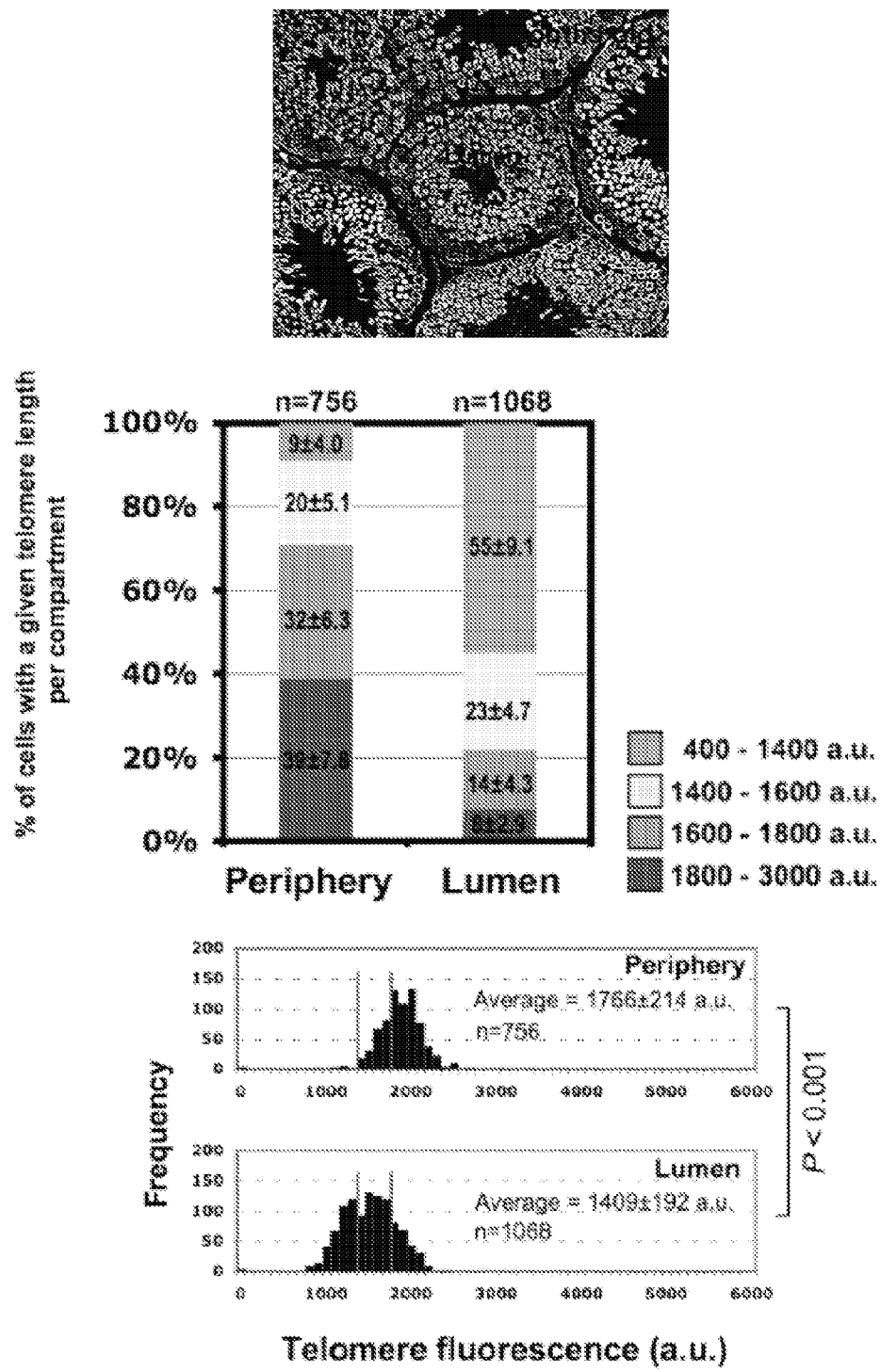
FIG. 14. Telomere shortening with age in male germ line stem cells. Representative topographic telomere length maps of testis epithelium sections from wild-type mice of the indicated age with confocal telomere Q-FISH images. The different cornea compartments are indicated. The dashed line separates the highlights the first cell layer of the seminiferous tubules, where the stem cells have been located (periphery). Nuclei are colored according to their average telomere fluorescence in arbitrary units (a.u.). Scale bars correspond to 200 µm. Middle panels show the percentage of cells containing a given telomere fluorescence within each epidermal compartment. Right panels show telomere fluorescence histograms of nuclei in each compartment. Note that the percentage of cells with the longest telomeres decreases in the stem cell compartment when comparing 2 month-old mice with 2 year old-mice. A total of 6 different testis images from 3 independent mice were used for quantification. For telomere length frequency histograms, average telomere length and standard deviation are indicated. Number of nuclei analyzed is also indicated. Statistical significance values are also indicated.
Figure 15:
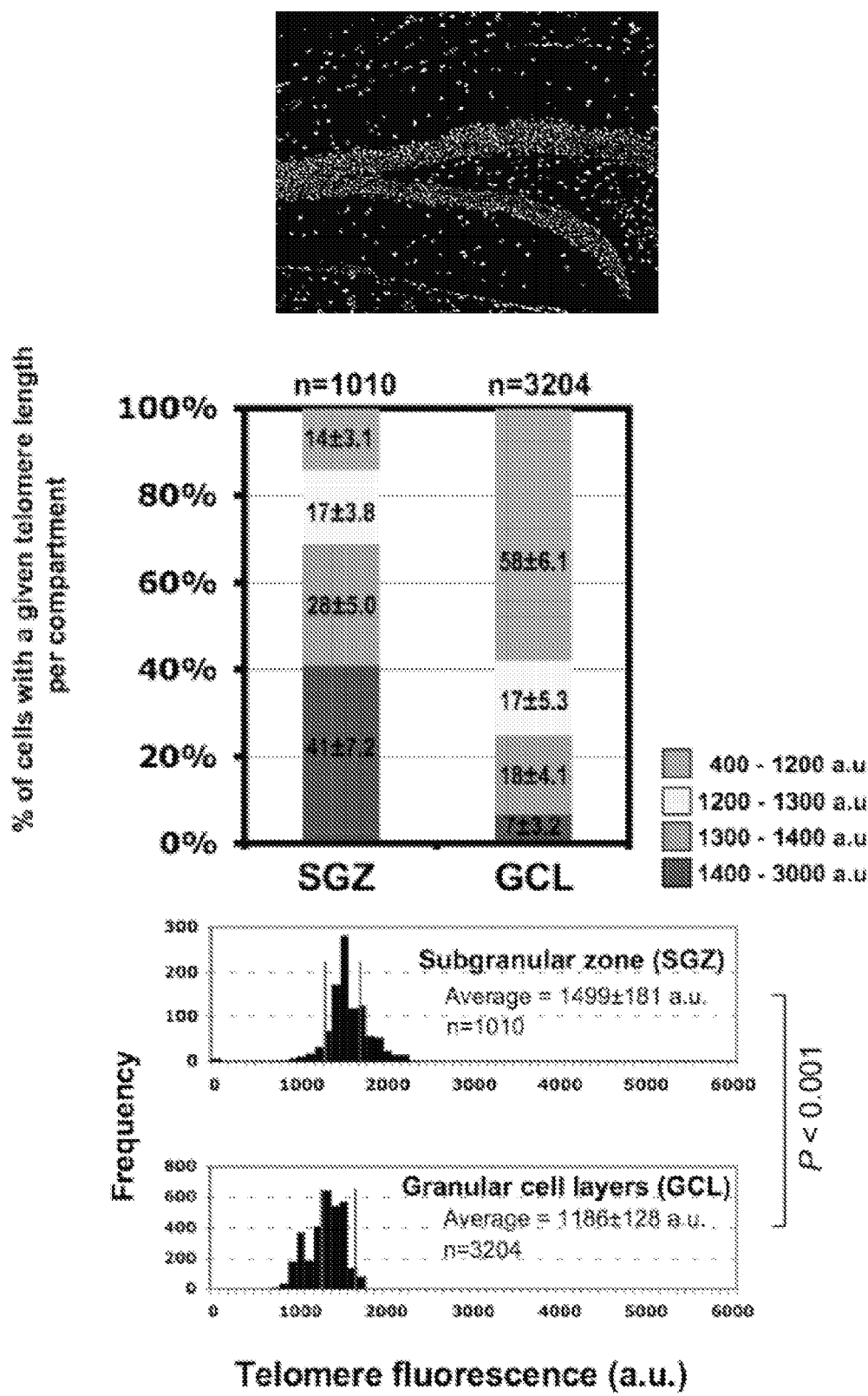
FIG. 15. Telomere shortening with age in brain stem cells. Representative topographic telomere length maps of brain sections from wildtype mice of the indicated age with confocal telomere Q-FISH images. The different cornea compartments are indicated. SGZ: subgranular zone, GCL: granular cell layer, H: hilus. The dashed line highlights the basal layer of the epithelium. Nuclei are coloured according to their average telomere fluorescence in arbitrary units (a.u.). Scale bars correspond to 200 µm. Middle panels show the percentage of cells containing a given telomere fluorescence within each epidermal compartment. Right panels show telomere fluorescence histograms of nuclei in each compartment. Note that the percentage of cells with the longest telomeres decreases in the stem cell compartment when comparing 2 month-old mice with 2 year old-mice. A total of 6 different brain images from 3 independent mice were used for quantification. For telomere length frequency histograms, average telomere length and standard deviation are indicated. Number of nuclei analyzed is also indicated. Statistical significance values are also indicated.

Of notice, telomere shortening with age in Mus musculus male germ cells is in agreement with previously reported telomere shortening with age in Mus spretus testis when comparing young (0-11 month-old) to old animals ($\geq$12 month-old) (Coviello-McLaughlin & Prowse, 1997). These findings suggest that, at least in the mouse, telomeres shorten with age in the male germ line. Finally, comparison of telomere shortening with age in all tissues studied here (FIG. 11d, e), indicates that telomere erosion rates vary at different ages, ranging from a slight reduction in length from 2 month-old to 1 year-old animals to a rapid telomere loss when comparing 2 month-old to 1 year-old mice, both in the stem cell and differentiated compartments. These results indicate that the mechanisms of telomere length maintenance decline more rapidly at advances ages, which in turn may contribute to stem cell aging and therefore to aging phenotypes.

Example 6

Reduced Clonogenic Potential of Mouse Skin Cells with Age

Figure 16:
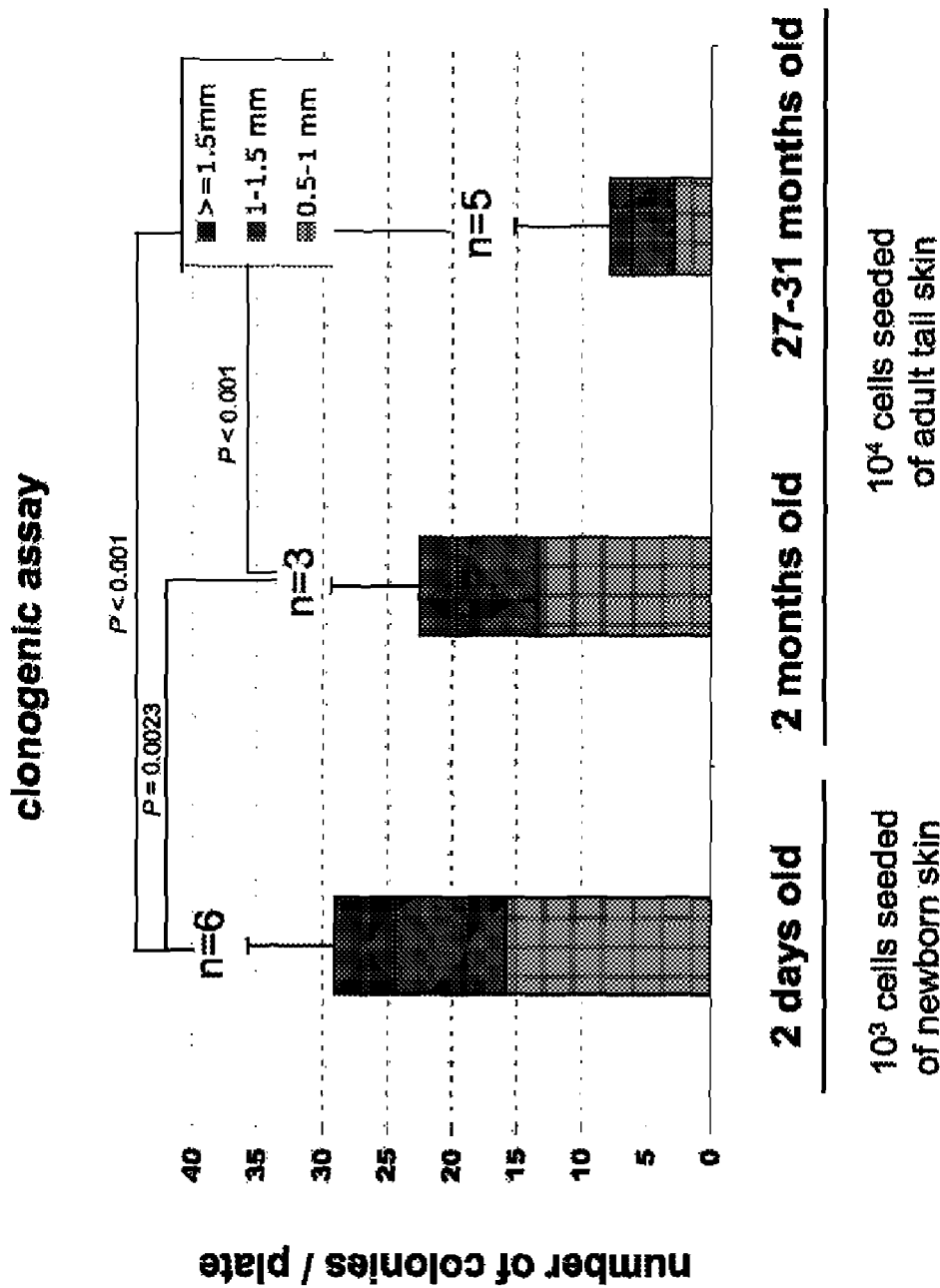
FIG. 16. Decreased clonogenic potential of epidermal stem cells with mouse aging. Aging affects the proliferative potential of mouse keratinocytes stem cells. Quantification of size and number of macroscopic colonies obtained from isolated keratinocytes from 2-days-old, 2-months-old and 27-31-months old mice and cultured for 10 days on J2-3T3 mitomycin-C-treated feeder fibroblast. Note that colony number decreases with aging. In the case of keratinocytes obtained from adult tail skin 10 times more cells were seeded onto the feeder layer to better assess their low colony formation efficiency. Statistical significance values are indicated.

The fact that telomeres shorten with age at different stem cell compartments in the mouse, may suggest that the mechanisms for telomere length maintenance decline more rapidly at advances ages, and that this telomere shortening may contribute to stem cell aging and therefore to aging phenotypes. To address this, the functionality of mouse epidermal stem cells at different ages was compared using clonogenic assays (Example 1), which reflect on the proliferative potential of epidermal stem cells (Flores et al., 2005). In agreement with their shorter telomeres, keratinocytes directly isolated from 27-31 month-old mice formed significantly fewer colonies than those derived from 2month-old mice (P<0.001; FIG. 16), indicating a decreased clonogenic potential of epidermal cells with aging. These results are in agreement with previous findings in human skin keratinocytes that showed decreased clonogenic potential with increasing age (Barrandon & Green, 1987).

BIBLIOGRAPHY

Alvarez-Buylla, A., and Lim, D. A. (2004). For the long run: maintaining germinal niches in the adult brain. Neuron 41, 683-686.

Baird, D. M., Rowson, J., Wynford-Thomas, D., and Kipling, D. (2003). Extensive allelic variation and ultrashort telomeres in senescent human cells. Nature genetics 33, 203-207.

Barrandon, Y., Green, H. (1987). Three clonal types of keratinocyte with different capacities for multiplication. Proc Natl Acad Sci USA. 84, 2302-2306.

Blasco, M. A., Lee, H-W., Hande, P., Samper, E., Lansdorp, P., DePinho, R., Greider, C. W. (1997). Telomere shortening and tumor formation by mouse cells lacking telomerase RNA. Cell 91, 25-34

Blasco, M. A. (2005). Telomeres and human disease: cancer, ageing and beyond. Nature Reviews Genetics 6, 611-622

Braun, K. M., Niemann, C., Jensen, U. B., Sundberg, J. P., Silva-Vargas, V., Watt, F. M. (2003). Manipulation of stem cell proliferation and lineage commitment: visualisation of label-retaining cells in wholemounts of mouse epidermis. Development 130, 5241-5255

Brinster, R. L. (2002). Germline stem cell transplantation and transgenesis. Science 296, 2174-2176.

Bryan, T. M. et al., (1997) Evidence for an alternative mechanism for maintaining telomere length in human tumors and tumor-derived cell lines. Nature Medicine 3:1271-1274.

Cawthon et al., (2003) Association between telomere length in blood and mortality in people aged 60 years or older, Lancet 361, 393-395.

Cawthon, R. M. (2002). Telomere measurement by quantitative PCR. Nucleic acids Research 30, e47.

Chan, S. W., and Blackburn, E. H. (2002). New ways not to make ends meet: telomerase, DNA damage proteins and heterochromatin. Oncogene 21, 553-563.

Collins, K., Mitchell, J. R. (2002). Telomerase in the human organism. Oncogene, 21, 564-579.

Canela A, Vera E, Klatt P, Blasco M A. (2007). High-throughput telomere length quantification by FISH and its application to human population studies. PNAS, 104, 5300-5305.

Cotsarelis, G., Sun, T. T., Lavker, R. M. (1990). Label-retaining cells reside in the bulge area of pilosebaceous unit: implications for follicular stem cells, hair cycle, and skin carcinogenesis. Cell 61, 1329-1337.

Coviello-McLaughlin, G. M., and Prowse, K. R. (1997). Telomere length regulation during postnatal development and ageing in *Mus spretus*. Nucleic Acids Res 25, 3051-3058.

de Lange, T. (2005). Shelterin: the protein complex that shapes and safeguards human telomeres. Genes and Dev 19, 2100-2110.

Epel, E. S. et al., (2004) Accelerated telomere shortening in response to life stress. Proc. Natl. Acad. Sci USA, 101: 17312-17315.

Flores, I., Benetti, R., and Blasco, M. A. (2006). Telomerase regulation and stem cell behaviour. Current Opinion Cell Biology 18, 254-260.

Flores, I., Cayuela, M. L., Blasco, M. A. (2005). Effects of telomerase and telomere length on epidermal stem cell behavior. Science 309, 1253-1256.

Freulet-Marriere, M. A., Potocki-Veronese, G., Deverre, J. R., and Sabatier, L. (2004). Rapid method for mean telomere length measurement directly from cell lysates. Biochemical and biophysical research communications 314, 950-956.

Fuchs, E., Tumbar, T, and Guasch, G. (2004). Socializing with the neighbours: stem cells and their niche. Cell 116, 769-778.

Gage, F. H. (2000). Mammalian neural stem cells. Science 287, 1433-1438.

García-Cao., I., García-Cao., M., Tomás-Loba, A., Martín-Caballero, J., Flores, J. M., Klatt, P., Blasco, M. A, and Serrano, M. (2006). Increased p53 activity does not accelerate telomere-driven aging. EMBO Reports 7, 546-552.

Gonzalez-Suarez, E., Samper, E., Flores, J. M. & Blasco, M. A. (2000). Telomerase-deficient mice with short telomeres are resistant to skin tumorigenesis. Nat Genet 26, 114-117.

Gregorieff, A., Pinto, D., Begthel, H., Destree, O., Kielman, M., Clevers, H., (2005). Expression pattern of Wnt signaling components in the adult intestine. Gastroenterology 129, 626-638.

Guan, K. et al. (2006) Pluripotency of spermatogonial stem cells from adult, mouse testis. Nature 440, 1199-1203.

Harley, C. B. et al., (1990) Telomeres shorten during ageing of human fibroblasts. Nature 345:458-460.

Harrington, L. (2004). Does the reservoir for self-renewal stem from the ends? Oncogene 23, 7283-7289.

Ito, M., Liu, Y., Yang, Z., Nguyen, J., Liang, F., Morris, R. J., Cotsarelis, G. (2005). Stem cells in the hair follicle bulge contribute to wound repair but not to homeostasis of the epidermis. Nat Med 11, 1351-1354.

Kim, N. W. et al., (1994) Specific association of human telomerase activity with immortal cells and cancer, Science, 266:2011-2015.

Lansdorp, P. M. (2005). Role of telomerase in hematopoietic stem cells. Ann N Y Acad Sci 1044, 220-227.

Lavker, R. M., Tseng, S. C., and Sun, T. T. (2004). Corneal epithelial stem cells at the limbus: looking at some old problems from a new angle. Exp Eye Res 78, 433-446.

Lehrer, M. S., Sun, T. T., and Lavker, R. M. (1998). Strategies of epithelial repair: modulation of stem cell and transit amplifying cell proliferation. J Cell Sci 111 (Pt 19), 2867-2875.

Marshman, E., Booth, C., and Potten, C. S. (2002). The intestinal epithelial stem cell. Bioessays 24, 91-98.

Mason, P. J., Wilson, D. B., Bessler, M. (2005). Dyskeratosis congenita—a disease of dysfunctional telomere maintenance. Curr Mol Med 5, 159-170.

McIlrath et al. (2001) Telomere length abnormalities in mammalian radiosensitive cells. Cancer Res 61, 912-915.

Meeker et al. (2002). Telomere length assessment in human archival tissues: combined telomere fluorescence in situ hybridization and immunostaining. Am J Pathol 160, 1259-1268.

Meeker, A. K., Hicks, J. L., Gabrielson, E., Strauss, W. M., De Marzo, A. M., and Argani, P. (2004). Telomere shortening occurs in subsets of normal breast epithelium as well as in situ and invasive carcinoma. Am J Pathol 164, 925-935.

Meeker, A. K. and De Marzo, A. M. (2004). Recent advances in telomere biology: implications for human cancer. Curr Opin Oncol 16, 32-38.

Moore, K. A. and Lemischka, I. R. (2006). Stem cells and their niches. Science 311, 1880-1885.

Morris, R. J., Liu, Y., Marles, L., Yang, Z., Trempus, C., Li, S., Lin, J. S., Sawicki, J. A., Cotsarelis, G. (2004). Capturing and profiling adult hair follicle stem cells. Nat Biotechnol 22, 411-417.

Moyzis, R. K., Buckingham, J. M., Cram, L. S., Dani, M., Deaven, L. L., Jones, M. D., Meyne, J., Ratliff, R. L., and Wu, J. R. (1988). A highly conserved repetitive DNA sequence, (TTAGGG)n, present at the telomeres of human chromosomes. Proc. Natl. Acad. Sci. USA 85, 6622-6626.

Muñoz, P., Blanco, R., Flores, J. M., and Blasco, M. A. (2005). XPF nuclease-dependent telomere loss and increased DNA damage in mice overexpressing TRF2 result in premature aging and cancer. Nature Genetics 10, 1063-1071.

Oshima, H., Rochat, A., Kedzia, C., Kobayashi, K., Barrandon, Y. (2001). Morphogenesis and renewal of hair follicles from adult multipotent item cells. Cell 104, 233-245.

Prowse, K. R., Greider, C. W. (1995). Developmental and tissue-specific regulation of mouse telomerase and telomere length. Proc Natl Acad Sci USA. 92, 4818-4822.

Ramirez, R. D., Wright, W. E., Shay, J. W., and Taylor, R. S. (1997). Telomerase activity concentrates in the mitotically active segments of human hair follicles. J. Invest Dermatol 108, 113-117.

Rufer, N., Dragowska, W., Thornbury, G., Roosnek, E., Lansdorp, P. M. (1998). Telomere length dynamics in human lymphocyte subpopulations measured by flow cytometry. Nat Biotechnol. 16, 743-747.

Samper, E., Goytisolo, F. A., Slijepcevic, P., van Buul, P. P., and Blasco, M. A. (2000). Mammalian Ku86 protein prevents telomeric fusions independently of the length of TTAGGG repeats and the G-strand overhang. EMBO rep 1, 244-252.

Sarin, K. Y., Cheung, P., Gilison, D., Lee, E., Tennen, R. I., Wang, E., Artandi, M. K., Oro, A. E., Artandi, S. E. (2005). Conditional telomerase induction causes proliferation of hair follicle stem cells. Nature 436, 1048-1052.

Therkelsen, A. J., Nielsen, A., Koch, J., Hindkjaer, J., and Kolvraa, S. (1995). Staining of human telomeres with primed in situ labeling (PRINS). Cytogenetics and cell genetics 68, 115-118.

Tumbar, T., Guasch, G., Greco, V., Blanpain, C., Lowry, W. E., Rendl, M., Fuchs, E. (2004). Defining the epithelial stem cell niche in skin. Science 303, 359-363.

Valdes et al., (2005) Obesity, cigarette smoking, and telomere length in women. Lancet, 366, 662-664.

Zijlmans, J. M., Martens, U. M., Poon, S. S., Raap, A. K., Tanke, H. J., Ward, R. K., Lansdorp, P. M. (1997). Telomeres in the mouse have large inter-chromosomal variations in the number of T2AG3 repeats. Proc. Natl. Acad. Sci. USA. 94, 7423-7428.

While the invention has been described in detail, and with reference to specific embodiments thereof, it will be apparent to one of ordinary skill in the art that various changes and modifications can be made therein without departing from the spirit and scope thereof. Various references are cited throughout this specification; the entire disclosure of each such reference is incorporated herein by reference in its entirety for all purposes.

sequence within telomeres, wherein the control cell populations have known, stable, and different average telomere lengths;

(ii) obtaining at least two fluorescence microscopy images of the test cell population and each one of the control cell populations by acquiring a fluorescence intensity emitted by the first fluorescent dye at a position in the fluorescence microscopy images in response to radiation, wherein each one of the fluorescence microscopy images of the test cell population and the control cell populations corresponds to a different focal plane of each population;

(iii) converting the at least two fluorescence microscopy images for each population into single images for each population by adding up the fluorescence intensity at each position within each focal plane for each population;

(iv) determining an average fluorescence intensity value in a cell of said test cell population and an average fluorescence intensity value of cells within each control cell population based on the single images obtained in step (iii); and (v) assigning to the cell of the test cell population an average telomere length value, wherein said average telomere length value is interpolated from the average fluorescence intensity value of each control cell population and the known average telomere lengths of the corresponding control cell populations.

2. The method according to claim 1, wherein the fluorescence microscopy images are confocal microscopy images.

3. The method according to claim 2, wherein more than one confocal image is collected in step (ii) of the method, wherein the confocal images span the entire depth of the test cell population.

4. The method according to claim 3, wherein a confocal microscope is programmed so as to obtain different confocal images at focal lengths of about 1 μm.

5. The method according to claim 1, wherein the test cell population is a tissue sample selected from the group consisting of skin, small intestine, testis, cornea, brain and tumor tissues.

The invention claimed is:

1. A method for the determination of an average telomere length of a cell in an immobilized tridimensional test cell population, the method comprising:

(i) contacting said test cell population and at least two control cell populations with a probe, wherein the probe is labeled with a first fluorescent dye and hybridizes in situ specifically to a complementary repeat DNA 6. The method according to claim 1, wherein the determination of the average fluorescence intensity value in the cells of said test cell population and said control cell populations is carried out in regions of the single images corresponding to cell nuclei.

7. The method according to claim 6, wherein the regions of the single images are defined using a fluorescent DNA dye.

8. The method according to claim 1, wherein each of the control cell populations comprise cells derived from a different cell line selected from the group consisting of Hela 2, HeLa, MCF7, HeLa S3, 293T, L5178Y-S, MEFs BL6 G3 Terc$^{-/-}$, MEFs BL6 wild type, HeLa 1211, MEFs 129Sv/BL6 wild-type and L5178Y-R.

9. The method according to claim 1, wherein the control cell populations are contained in a tissue microarray which comprises at least two cell populations in a single receiver block, wherein the receiver block can be sectioned by conventional means and processed in parallel to the test cell population, wherein each control cell population is physically separated from the other cell populations(s) of the microarray and wherein each control cell population has a stable, known, and different average telomere length from the other cell populations(s) of the microarray.

10. The method according to claim 9, wherein the test cell population and the tissue microarray are co-processed to carry out steps (i) to (v).

11. The method of claim 1, wherein the average fluorescence intensity value for the cell of the test cell population is the sum of the fluorescence intensity at each pixel within a region of interest divided by the total number of pixels for the region of interest, wherein the region of interest corresponds to the nucleus of the cell.

12. The method of claim 1, wherein each control cell population is a homogenous immobilized control cell population.

* * * * *